US010053703B2

(12) United States Patent
Simonsen et al.

(10) Patent No.: US 10,053,703 B2
(45) Date of Patent: Aug. 21, 2018

(54) HETEROLOGOUS PRODUCTION OF PATCHOULOL, β-SANTALENE, AND SCLAREOL IN MOSS CELLS

(71) Applicants: UNIVERSITY OF COPENHAGEN, Copenhagen K (DK); FIRMENICH SA, Meyrin (CH)

(72) Inventors: Henrik Simonsen, Horsholm (DK); Dong-Fang Chen, Leicester (GB); Xin Zhan, Valby (DK); Xiwu Pan, Shanghai (CN); Brian Christopher King, Copenhagen N (DK)

(73) Assignees: UNIVERSITY OF COPENHAGEN, Copenhagen (DK); FIRMENICH SA, Geneva (CH)

( * ) Notice: Subject to any disclaimer, the term of this patent is extended or adjusted under 35 U.S.C. 154(b) by 84 days.

(21) Appl. No.: 14/901,320

(22) PCT Filed: May 7, 2014

(86) PCT No.: PCT/DK2014/050130

§ 371 (c)(1),
(2) Date: Dec. 28, 2015

(87) PCT Pub. No.: WO2014/206412

PCT Pub. Date: Dec. 31, 2014

(65) Prior Publication Data

US 2016/0222401 A1 Aug. 4, 2016

(30) Foreign Application Priority Data

Jun. 28, 2013 (DK) ................................ 2013 70367

(51) Int. Cl.

| | |
|---|---|
| ***C12N 5/14*** | (2006.01) |
| ***C12P 7/02*** | (2006.01) |
| ***C12N 5/00*** | (2006.01) |
| ***C12N 15/82*** | (2006.01) |
| ***C12P 15/00*** | (2006.01) |
| ***C12P 5/00*** | (2006.01) |

(52) U.S. Cl.
CPC ..... *C12N 15/8257* (2013.01); *C12N 15/8243* (2013.01); *C12P 5/002* (2013.01); *C12P 5/007* (2013.01); *C12P 7/02* (2013.01); *C12P 15/00* (2013.01); *C12Y 402/03* (2013.01); *C12Y 402/0307* (2013.01); *C12Y 402/03083* (2013.01)

(58) Field of Classification Search
CPC . C12N 15/8257; C12N 15/8243; C12P 5/002; C12P 15/00; C12Y 402/0307
See application file for complete search history.

(56) References Cited

U.S. PATENT DOCUMENTS

2010/0297722 A1* 11/2010 Anterola ................ C07K 16/40 435/167
2011/0262986 A1* 10/2011 Burbaum ............... C12M 21/02 435/167

FOREIGN PATENT DOCUMENTS

WO WO 2005/052163 * 6/2005

OTHER PUBLICATIONS

Branden et al., Introduction to Protein Structure, Garland Publishing Inc., New York, p. 247.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*

* cited by examiner

*Primary Examiner* — Delia Ramirez

(57) ABSTRACT

The present invention relates to methods for preparing patchoulol, β-santalene, and sclareol in transgenic moss cells that include heterologous nucleic acid molecules encoding a polypeptide or synthase capable of using FPP or GGPP as a substrate. Methods for producing the transgenic moss cell, as well as the transgenic moss cell itself are also disclosed.

8 Claims, 16 Drawing Sheets

I - patchoulol

II - β-santalene

III - sclareol

HETEROLOGOUS PRODUCTION OF PATCHOULOL, β-SANTALENE, AND SCLAREOL IN MOSS CELLS

Figure 1:
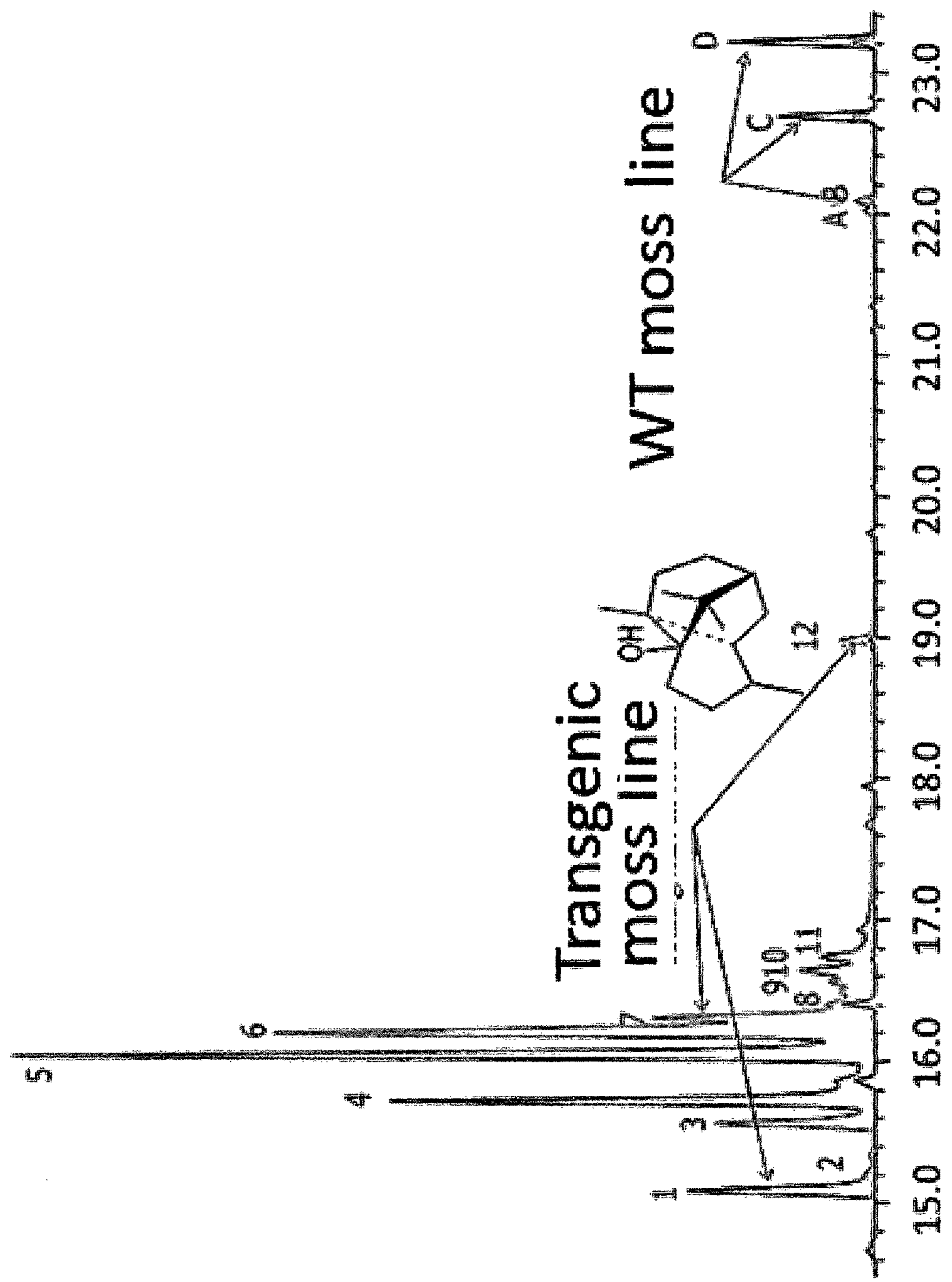

This application is a 371 filing of International Patent Application PCT/DK2014/050130 filed May 7, 2014, which claims the benefit of Danish patent application no. PA 2013 70367 filed Jun. 28, 2013.

SEQUENCE LISTING SUBMISSION

The Sequence Listing associated with this application is filed in electronic format via EFS-Web and hereby incorporated by reference into the specification in its entirety. The name of the text file containing the Sequence Listing is 9430US_revisedSequenceListing. The size of the text file is 111 KB, and the text file was created on Mar. 29, 2018.

FIELD OF THE INVENTION

The present invention relates to methods for production of patchoulol, β-santalene, and sclareol in transgenic moss (*Physcomitrella patens*) cells comprising heterologous nucleic acid molecules encoding a synthase capable of using FPP or GGPP as substrate, methods for producing the transgenic moss cells, as well as the transgenic moss cells itself.

BACKGROUND

Terpenoids or terpenes represent a family of natural products found in all organisms (bacteria, fungi, animals, plants) and these compounds are made up of five carbon units called isoprene units, which are classified by the number of units present in their structure. Thus, monoterpenes, sesquiterpenes and diterpenes are terpenes containing 10, 15 and 20 carbon atoms respectively. The common five-carbon precursor to all terpenes is isopentenyl pyrophosphate (IPP). IPP forms the acyclic prenyl pyrophosphate terpene precursors for each class of terpenes, e.g. farnesyl-pyrophosphate (FPP) for the sesquiterpenes, and geranylgeranyl-pyrophosphate (GGPP) for the diterpenes. These precursors serve as substrate for the terpene synthatases or cyclases, which are specific for each subclass of terpene, e.g. monoterpene, sesquiterpene or diterpene synthases. Some terpene synthases produce a single product, but most of them produce multiple products. The synthases are responsible for the extremely large number of terpene skeletons. Finally, in the last stage of terpenoid biosynthesis, the terpene molecules may undergo several steps of secondary enzymatic transformations such as hydroxylations, isomerisations, oxido-reductions or acylations, leading to the tens of thousand of different terpene molecules.

Patchoulol and β-santalene are classified as sesquiterpenes whereas sclareol is classified as a diterpene.

The biosynthesis of terpenes in plants has been extensively studied and heterologous expression, in vivo, and in vitro testing are important tools when characterizing genes involved in terpenes biosynthesis. Until now, most plant genes encoding isoprenoid biosynthetic synthases have been characterized using bacterial, yeast, or insect cell-based expression systems [1,2]. However, synthase activity is highly dependent on the assay conditions and choice of heterologous expression hosts. For example, it has been demonstrated that acidification of the yeast growth media led to rearrangement of enzymatic products [2]. Similarly, a diterpene synthase from Norway spruce was shown to be a multi-product synthase when purified and characterized in vitro, but when expressed in yeast and characterized in vivo only a single product accumulated [3, 4]. It was also recently shown that a monoterpene synthase from sweet basil generated different product profiles when characterized using microbial systems compared to in planta characterization [5]. Hence, the biochemical function of a plant synthatase expressed in bacterial or fungal hosts may differ from the endogenous in planta function.

U.S. Pat. No. 8,058,046 relates to sesquiterpene synthases derived from patchouli plants, and methods of their production in suitable host cells such prokaryotes, yeast or higher eukaryotic cells. U.S. Pat. No. 8,058,046 provides nucleic acid molecules identified in *Pogostemon cablin* comprising a nucleotide sequence that encodes for at least one sesquiterpene synthase, which may be used to convert e.g. farnesyl-pyrophosphate (FPP) to various sesquiterpenes, including patchoulol. U.S. Pat. No. 8,058,046 exemplifies the expression of sesquiterpene synthases from patchouli plants in bacteria, *E. coli*.

US20110281257 relates to sesquiterpene synthases derived from *Santalum* species, and methods of their production in suitable host cells such prokaryotes, yeast or higher eukaryotic cells. US20110281257 exemplifies expression of sesquiterpene synthases from *Santalum* species in at least *S. cerevisiae*. US20110281257 provides nucleic acid molecules and variants thereof comprising a nucleotide sequence that encodes for at least one sesquiterpene synthase, which may be used to convert e.g. farnesyl-pyrophosphate (FPP) to various sesquiterpenes including β-santalene.

Genes encoding diterpene synthases have been identified and cloned and the corresponding recombinant enzymes characterized. Amongst other, US2011041218 relates to sclareol synthases, a diterpeniod, from *Salvia sclarea* species, and methods of their production in suitable host cells such as prokaryotes, yeast or higher eukaryotic cells. US2011041218 exemplifies expression of the diterpene synthases from *Salvia sclarea* in at least *S. cerevisiae*. US2011041218 provides nucleic acid molecules and variants thereof comprising a nucleotide sequence that encodes for various diterpene synthases, which may be used to convert e.g. geranylgeranyl-pyrophosphate (GGPP) to prepare sclareol. US2011041218 describes amongst other two synthases wherein GGPP is first converted to labdenediol diphosphate (LPP) and then converted to sclareol.

US20100297722 relates to the provision of compositions and processes for production of terpenoids from transgenic moss cells. US 20100297722 specifically relates to overexpression of various taxadiene synthases having activities towards geranylgeranyl-pyrophosphate and the derivatives thereof to produce different intermediates and end-products of diterpeniod compounds. In particular, expression or overexpression of specific polypeptides in *Physcomitrella patens* resulting in the production of terpenoid compounds such as various substituted taxadienes, 10-deacetylbaccatin III, abietadiene, abietic acid, steviol, steviolmonoside; stevioside; rebaudioside A, kaurenoic acid, a cembranoid, momilactone A-B, oryzalexins A-F, oryzalexin S and phytocassanes A-E, are exemplified.

Sesquiterpenes and diterpenes, including patchoulol, β-santalene, and sclareol, accumulates in plants and can be extracted by different means such as steam distillation or solvent extraction that produces the so-called essential oil containing the concentrated terpenes. Such natural plant extracts are important components for the flavor and perfumery industry due to their flavour and fragrance properties, and some sesquiterpenes and diterpenes may even possess cosmetic, medicinal and antimicrobial effects. Extracted terpene molecules are often used as such, but in some cases chemical reactions are used to transform the terpenes into even higher valued molecules Because of the complexity of the terpene structure, production of individual terpene molecules by chemical synthesis is often limited by the cost of the process and may not always be chemically or financially feasible. The price and availability of the plant natural extracts is dependent on the abundance, the oil yield and the geographical origin of the plants. The recent progress in understanding terpene biosynthesis in plants and the use of modern biotechnology techniques opens new opportunities for the production of terpene molecules. Thus, there exist a continuously need to provide improved biological production of terpenes and products derived therefrom, such as patchoulol, sclareol, and β-santalene, at more environmental friendly conditions and/or higher efficiency.

SUMMARY OF THE INVENTION

The present invention provides means and methods to biosynthetically prepare patchoulol, β-santalene, and sclareol from transgenic moss cells.

Thus, it is an object of the present invention in a first aspect to provide a method for producing a transgenic moss cell comprising introducing into a moss cell capable of producing farnesyl-pyrophosphate (FPP) or geranylgeranyl-pyrophosphate (GGPP) a heterologous nucleic acid molecule encoding a polypeptide, the polypeptide having a patchoulol synthase activity or β-santalene synthase activity to catalyze the conversion of FPP to pathoulol or β-santalene, or a sclareol synthase activity to catalyse the conversion of GGPP to sclareol, wherein the heterologous nucleic acid molecule is at least 70% identical to SEQ ID NO 1, SEQ ID NO 2, or SEQ ID NO 3. In an aspect of the invention the method above comprise a polypeptide, which is at least 70% identical to the polypeptide encoded by SEQ ID NO 1, SEQ ID NO 2, or SEQ ID NO 3.

In another aspect of the invention, a method for preparing pathoulol, β-santalene, or sclareol in a transgenic moss cell comprising;

a) introducing into a moss cell capable of producing farnesyl-pyrophosphate (FPP) or geranylgeranyl-pyrophosphate (GGPP) a heterologous nucleic acid molecule encoding a polypeptide, the polypeptide having a patchoulol synthase activity or β-santalene synthase activity to catalyze the conversion of FPP to pathoulol or β-santalene, or a sclareol synthase activity to catalyse the conversion of GGPP to sclareol, wherein the heterologous nucleic acid molecule is at least 70% identical to SEQ ID NO 1, SEQ ID NO 2, or SEQ ID NO 3.

b) culturing the transgenic moss cell to express or over-express the polypeptide encoded by the heterologous nucleic acid molecule, and c) isolating pathoulol, β-santalene, and/or sclareol produced in step b), is provided.

In one embodiment, isolation of pathoulol, β-santalene, and/or sclareol in the step c), may be performed by steam distillation and/or vacuum distillation.

In an aspect of the invention the method for producing pathoulol, β-santalene, or sclareol comprises a polypeptide which is at least 70% identical to the polypeptide encoded by SEQ ID NO 1, SEQ ID NO 2, or SEQ ID NO 3.

In yet another aspect of the invention, a transgenic moss cell capable of producing FPP or GGPP, the transgenic moss cell comprises a heterologous nucleic acid molecule encoding one or more polypeptides, the polypeptide having a patchoulol synthase activity or β-santalene synthase activity to catalyze the conversion of FPP to pathoulol or β-santalene, or a sclareol synthase activity to catalyse the conversion of GGPP to sclareol, wherein the heterologous nucleic acid molecule is at least 70% identical to SEQ ID NO 1, SEQ ID NO 2, or SEQ ID NO 3, or the polypeptide is at least 70% identical to the polypeptide encoded by SEQ ID NO 1, SEQ ID NO 2, or SEQ ID NO 3, is provided.

Further, in one embodiment, the moss cell or transgenic moss cell is selected from the group comprising of Takakiopsida, Sphagnopsida, Andreaeopsida, Andreaeobryopsida, Oedipodiopsida, Polytrichopsida, Tetraphidopsidaan and Bryopsida. Preferably, the moss cell or transgenic moss cell is *Physcomitrella patens*.

In yet another embodiment, the heterologous nucleic acid molecule is at least 70%, 75%, 80%, 85%, 90%, 92%, 94%, 96%, 97%, 98%, or 99% identical to SEQ ID NO 1, SEQ ID NO 2, or SEQ ID NO 3, or the polypeptide is at least 70%, 75%, 80%, 85%, 90%, 92%, 94%, 96%, 97%, 98%, or 99% identical to the polypeptide encoded by SEQ ID NO 1, SEQ ID NO 2, or SEQ ID NO 3.

It has been found be the present invention that moss cells can be transformed to produce terpenes such as patchoulol, β-santalene or sclareol. This is beneficial as these terpenes can be produced more environmental friendly and/or more efficiently due to e.g. higher expression yields and/or more convinient purification steps.

FIGURES

FIG. 1. Volatile metabolite profile of the transgenic moss lines producing patchoulol obtained by HS-SPME GC-MS analysis (X-axis is in min.). 1 denotes β-patchoulene; 2 denotes β-elemene; 3 denotes (E)-β-caryophyllene; 4 denotes α-guaiene; 5 denotes seychellene; 6 denotes α-patchoulene; 7 denotes γ-patchoulene; 8 denotes guai-4,11-diene; 9 denotes an unidentified sesquiterpene; 10 denotes α-bulnesene; 11 denotes an unidentified sesquiterpene; 12 denotes (−)-patchoulol; A denotes an unidentified diterpene; B denotes an unidentified diterpene; C denotes ent-15-kaurene; and D denotes ent-16-kaurene. The WT moss line produces primarily the following products; A, B, C and D, whereas the transgenic line primarily produces the following products; 1, 2, 3, 4, 5, 6, 7, 8, 9, 10, 11 and 12 [(−)-patchoulol].

Figure 2:
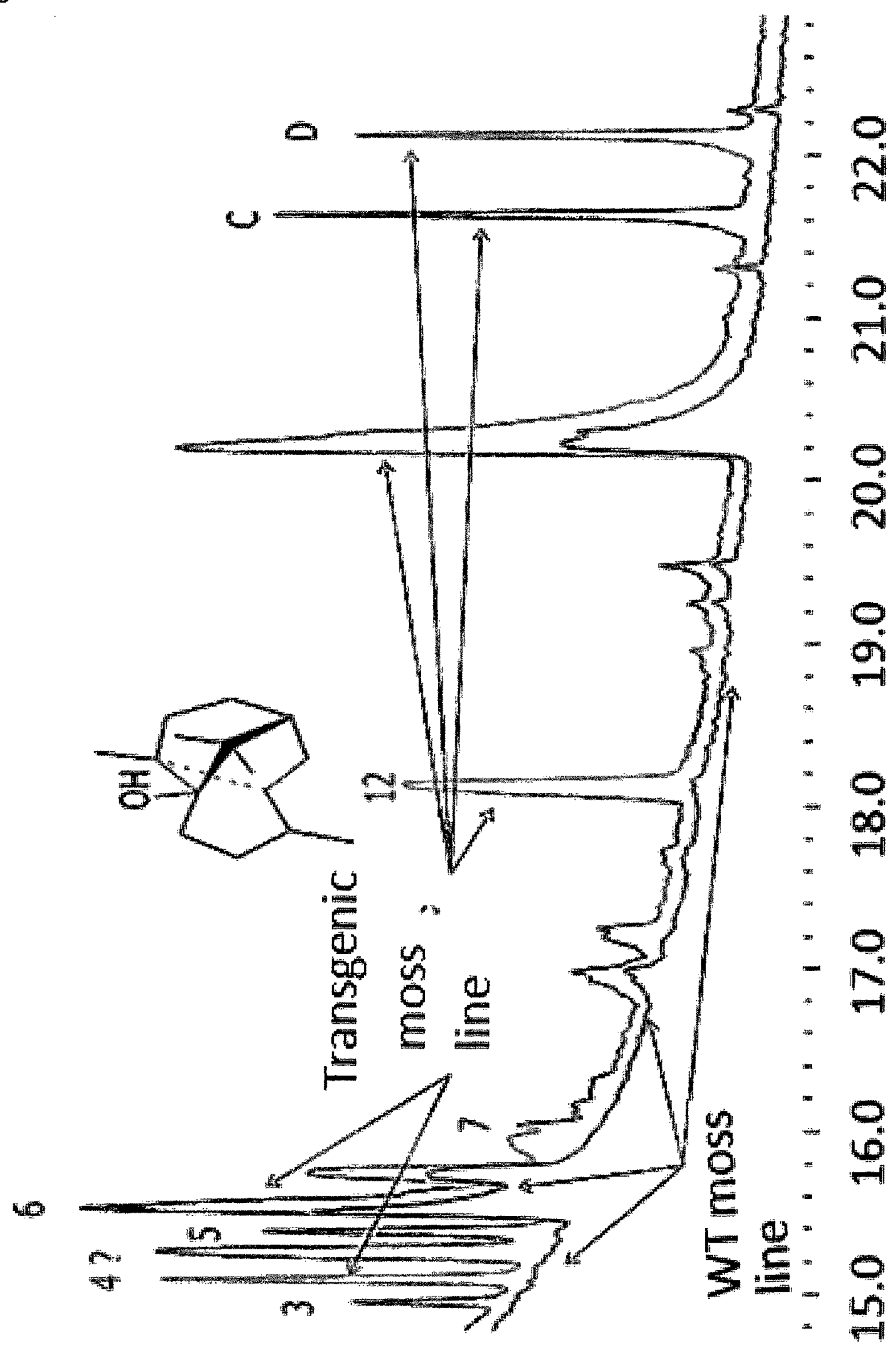

FIG. 2. Volatile metabolite profile of the transgenic moss lines using dodecane overlays (X-axis is in min.). 3 denotes (E)-β-caryophyllene; 4 denotes α-guaiene; 5 denotes seychellene; 6 denotes α-patchoulene; 7 denotes γ-patchoulene; C denotes ent-15-kaurene; and D denotes ent-16-kaurene. The PpCPS/KS knock-out patchoulol producing moss line produces the lowest amount of the different measured terpen products, whereas the patchoulol producing transgenic line primarily produces the following products; 3, 4, 5, 6, 7, 12 [(−)-patchoulol], C and D.

Figure 3:
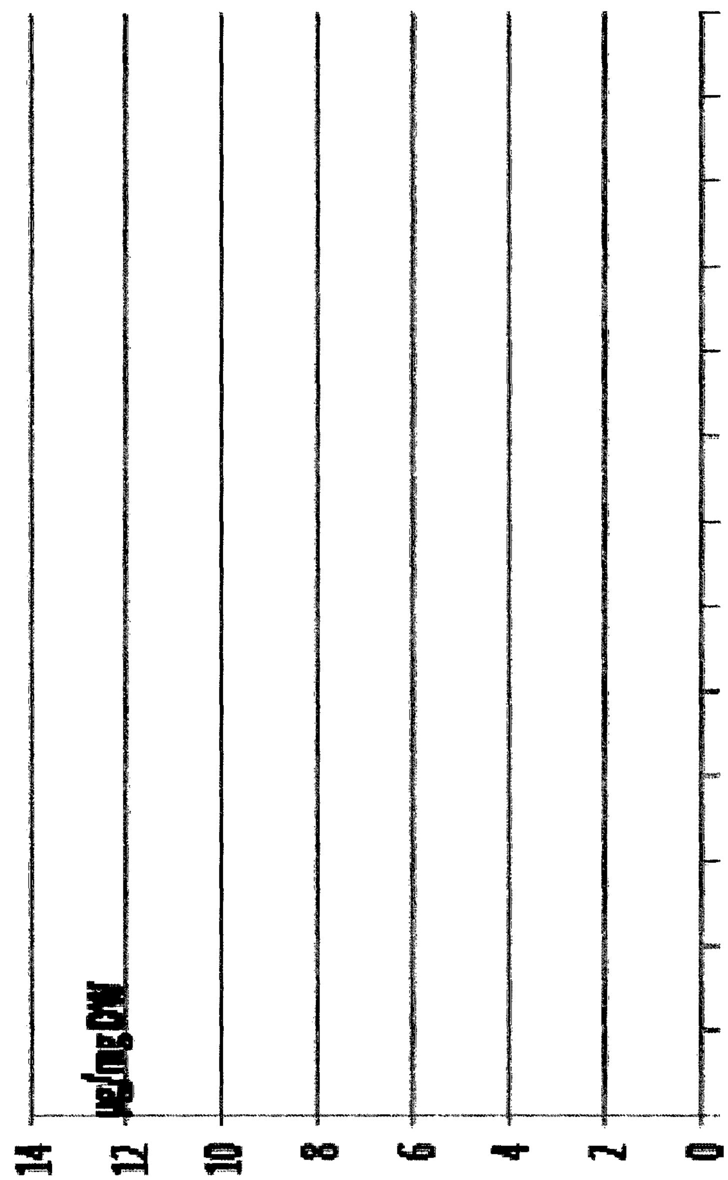

FIG. 3. The yields of patchoulol (μg/mg DW).

Figure 4:
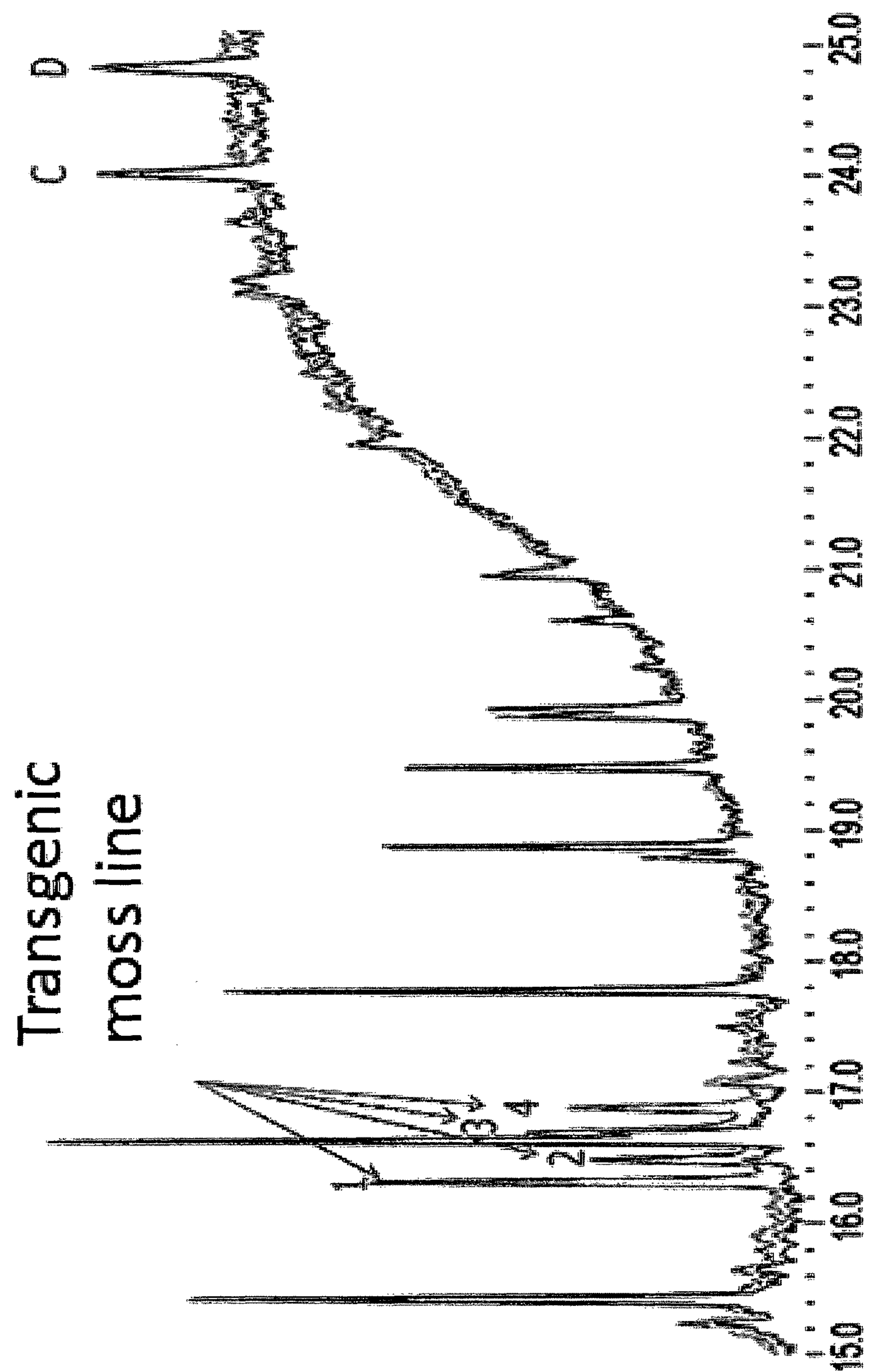

FIG. 4. Volatile metabolites profile of the transgenic line producing β-santalene by HS-SPME analysis (X-axis is in min.). 1 denotes α-santalene; 2 denotes (E)-α-bergamotene; 3 denotes epi-β-santalene; 4 denotes β-santalene; C denotes ent-15-kaurene; and D denotes ent-16-kaurene. The transgenic line produces amongst other the following products; 1, 2, 3, and 4 [β-santalene], whereas the WT moss line does not produces any significant amounts of these when compared to the transgenic line.

Figure 5:
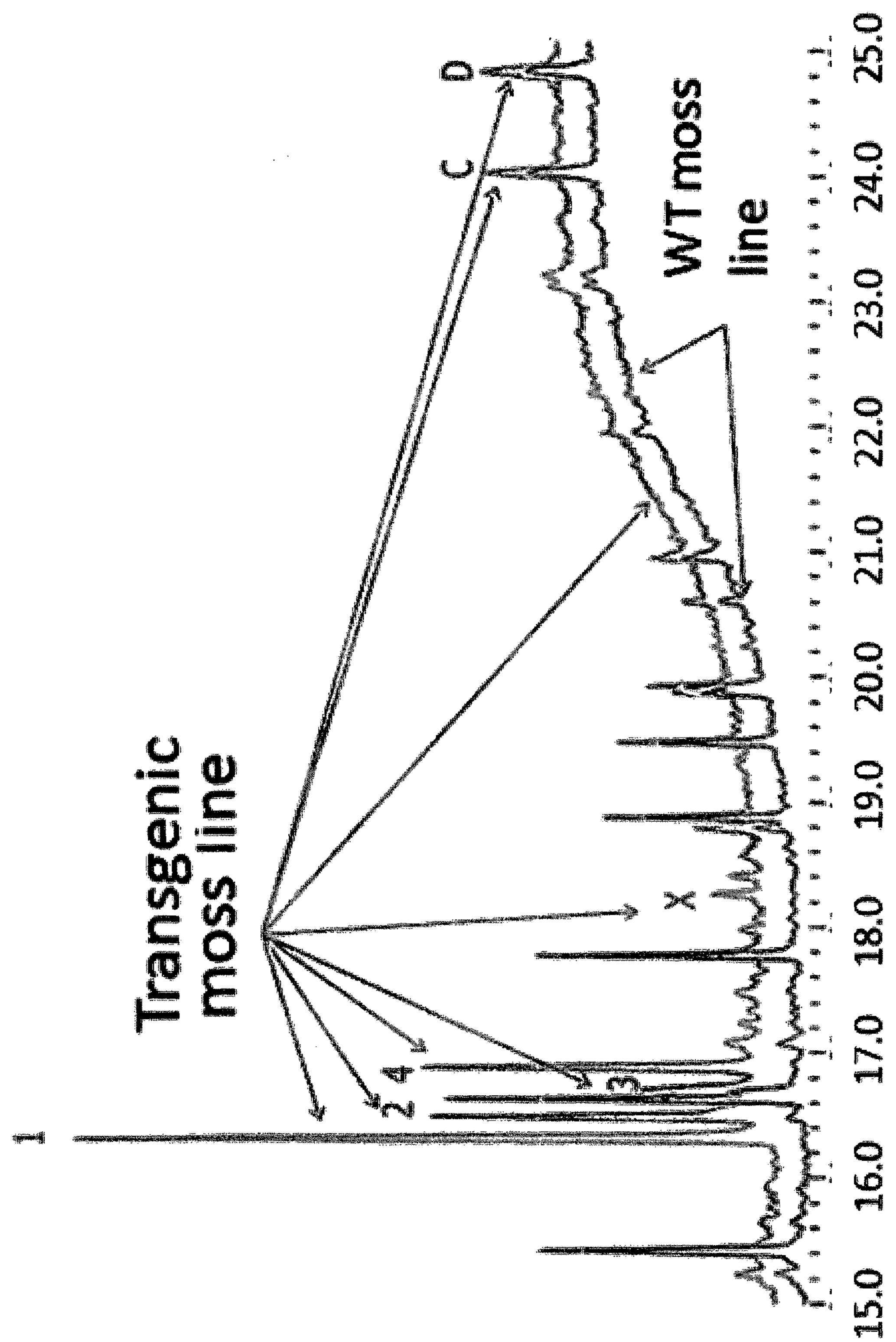

FIG. 5. Volatile metabolite profile of the transgenic line producing β-santalene with plastidic STS enzyme (X-axis is in min.). 1 denotes α-santalene; 2 denotes (E)-α-bergamotene; 3 denotes epi-β-santalene; 4 denotes β-santalene; C denotes ent-15-kaurene; and D denotes ent-16-kaurene. The transgenic line produces amongst other the following products; 1, 2, 3, and 4 [β-santalene], whereas the WT moss line does not produces any significant amounts of these when compared to the transgenic line.

Figure 6:
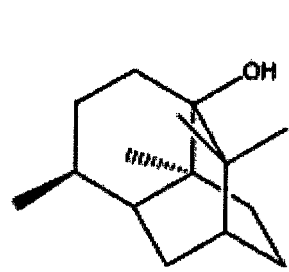
Figure 6:
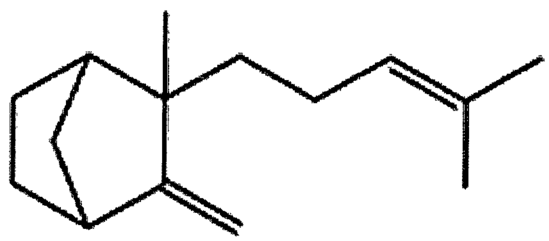
Figure 6:
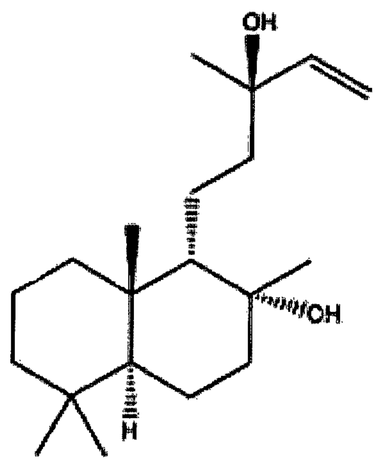

FIG. 6. Formula I represents patchoulol, formula II represents β-sanatalene and formula III represents sclareol.

Figure 7:
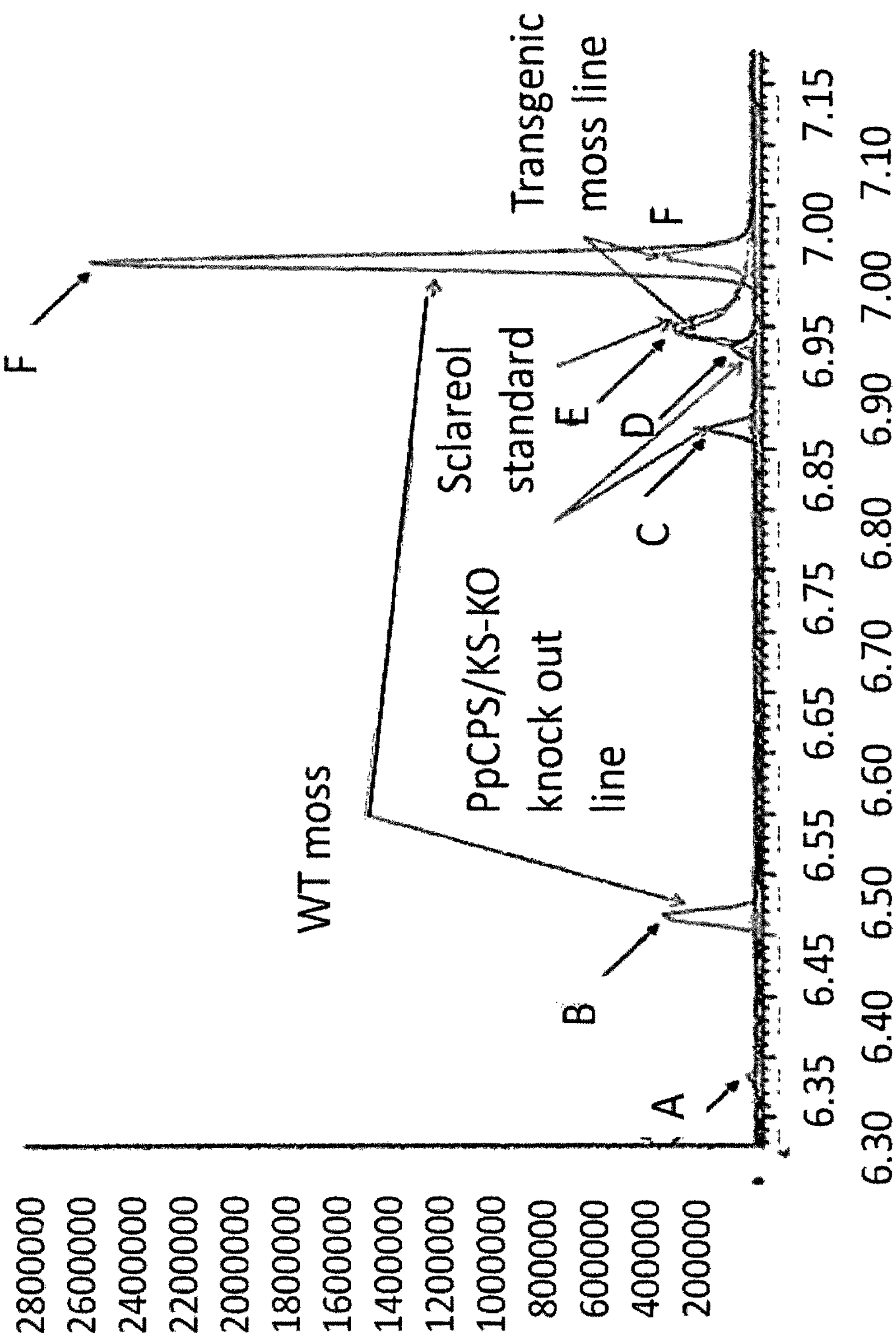

FIG. 7. Volatile metabolite profile of the transgenic line producing sclareol (X-axis is in min.). A denotes ent-15-kaurene, B denotes ent-16-kaurene, C+D are unknown compounds, E denotes sclareol, F denotes 16-OH-ent-kaurene. WT moss line produces amongst other product A, B and F. PpCPS/KS-KO produces amongst other product C and D. The transgenic sclareol producing line produces amongst other product E [Sclareol] and F.

Figure 8:
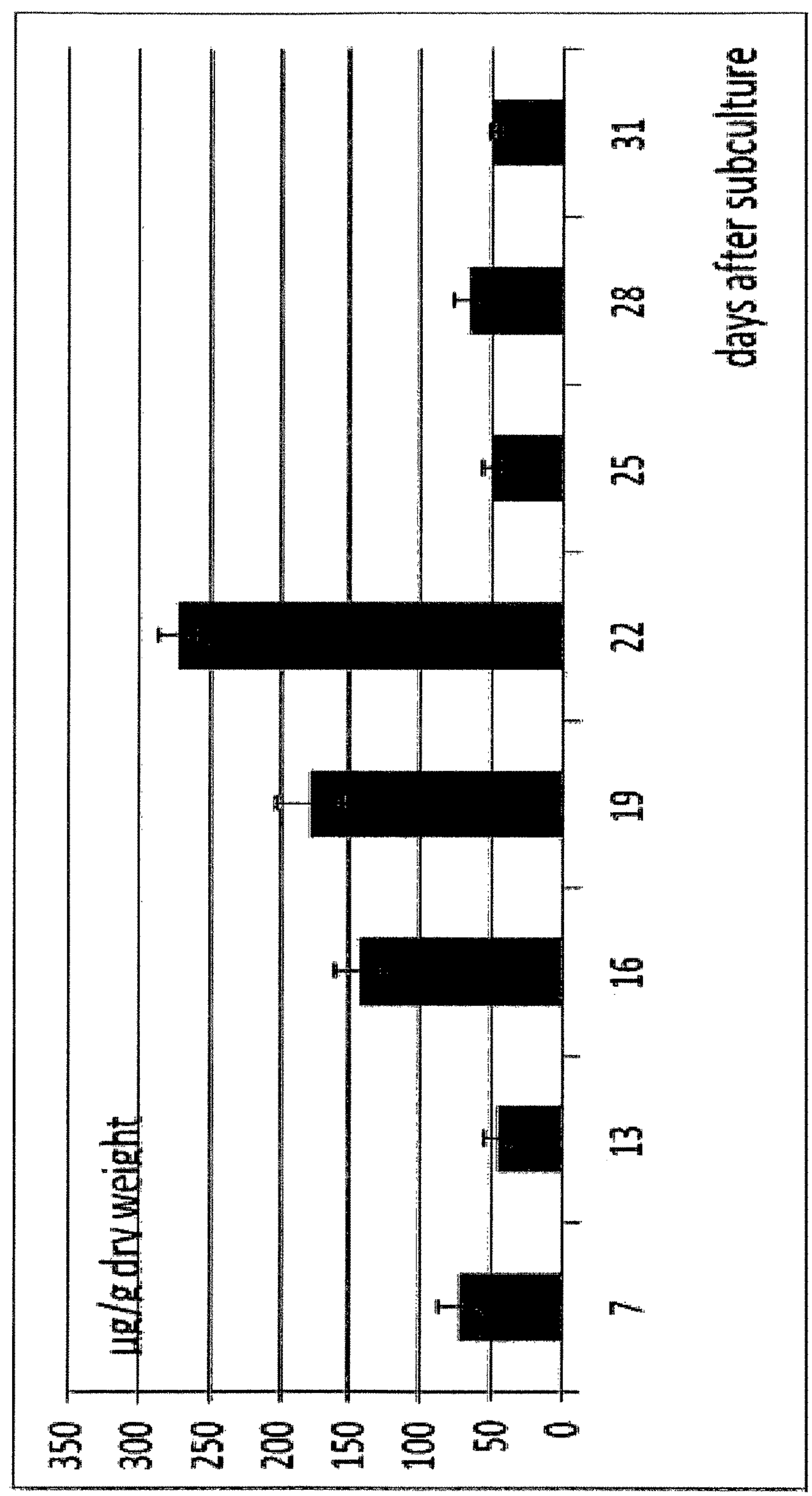

FIG. 8. Time course measurement of sclareol production im KO-pUNI33-TPSsa3-"A-TPS1132, leading to 280 μg/g dry weight of Sclareol.

Figure 9:
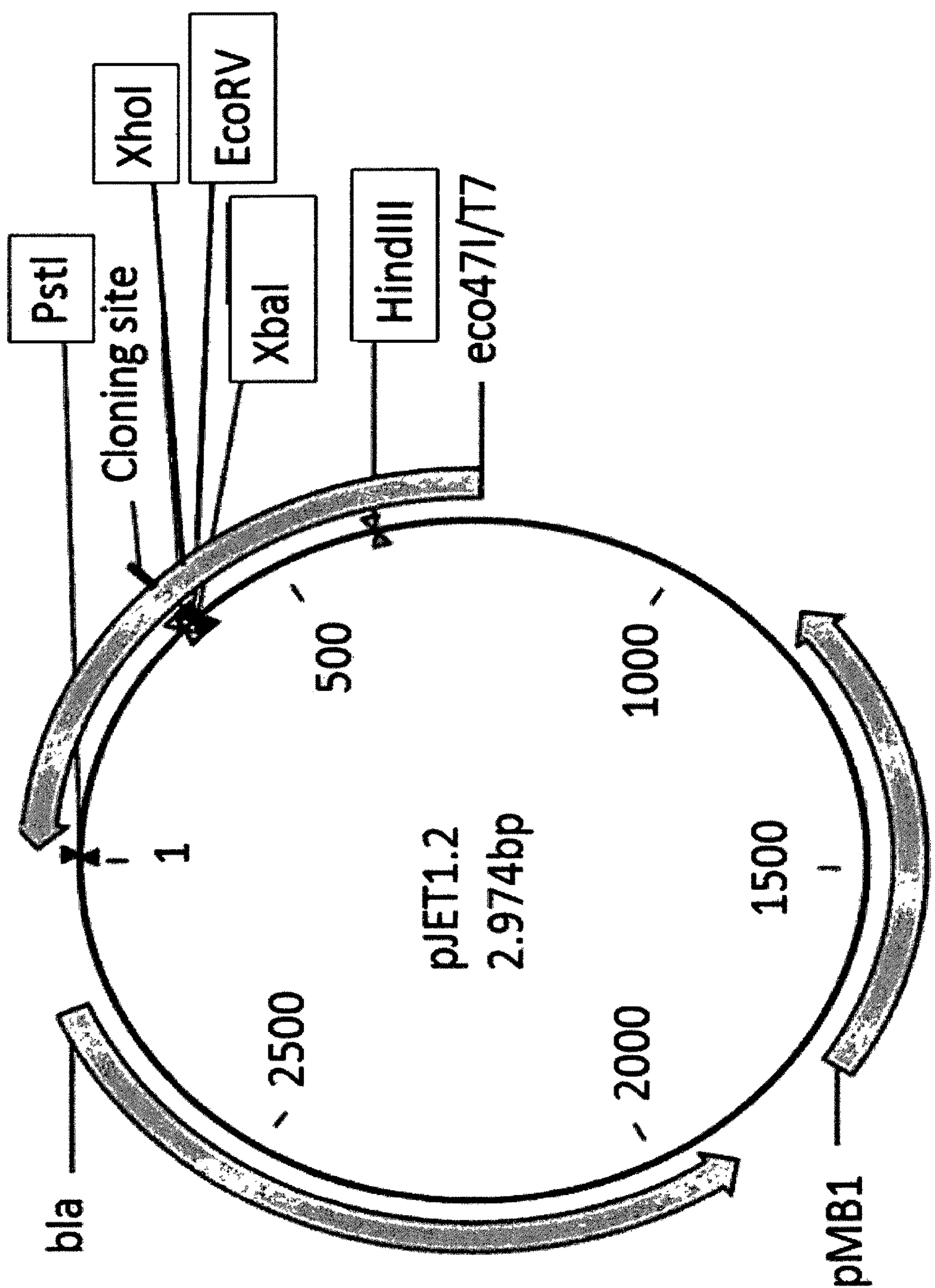

FIG. 9. Map of pJET1.2. See also SEQ ID NO 6. pJET1.2 is an artificial DNA sequence from Thermo Scientific designed for biological research.

Figure 10:
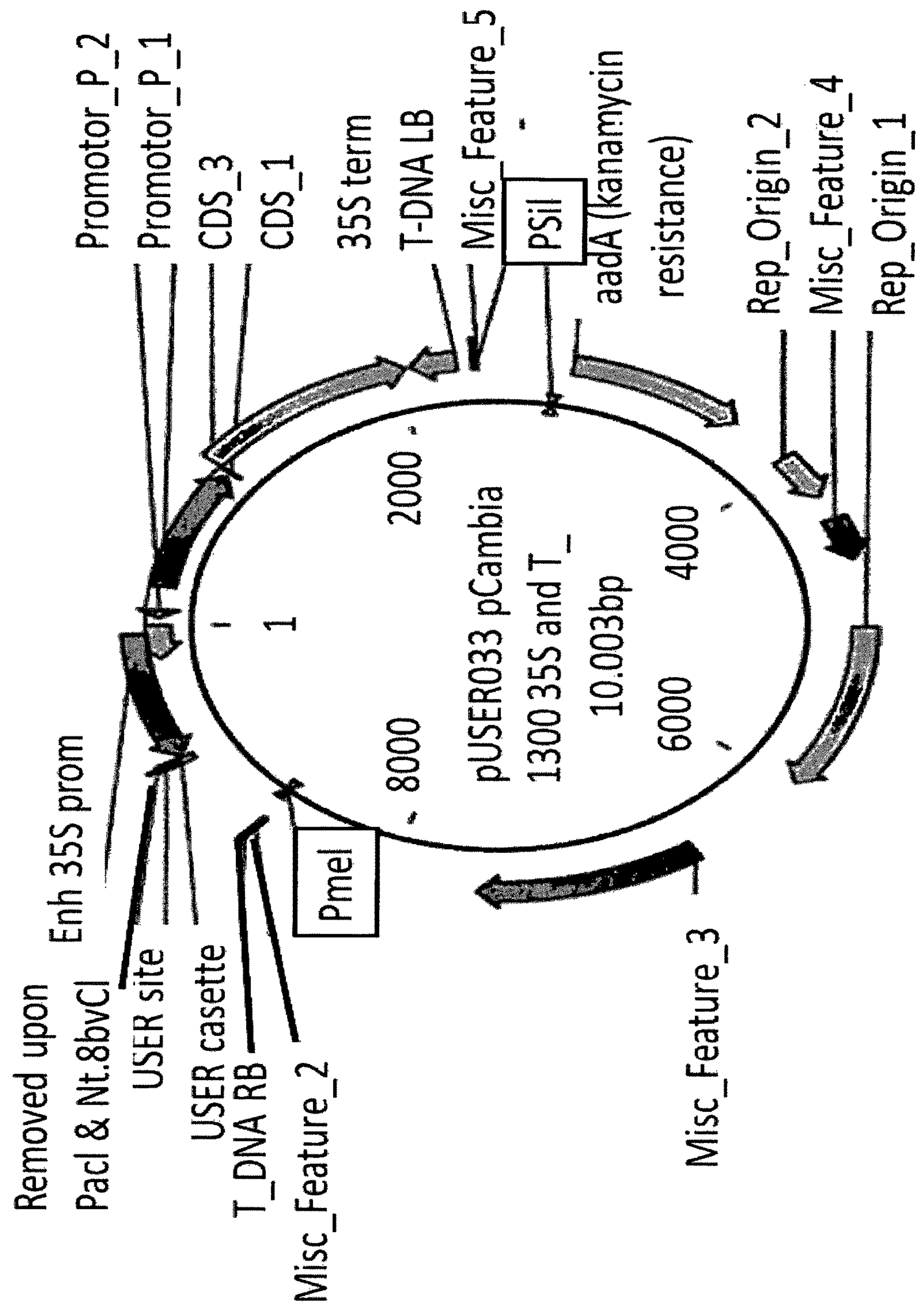

FIG. 10. Map of pLIFE33: See also SEQ ID NO 7. pLIFE33 is an artificial DNA sequence designed for biological research. The sequence was created on the basis of pCAMBIA 1300U, which is designed by CAMBIA, a non-profit scientific organization.

Figure 11:
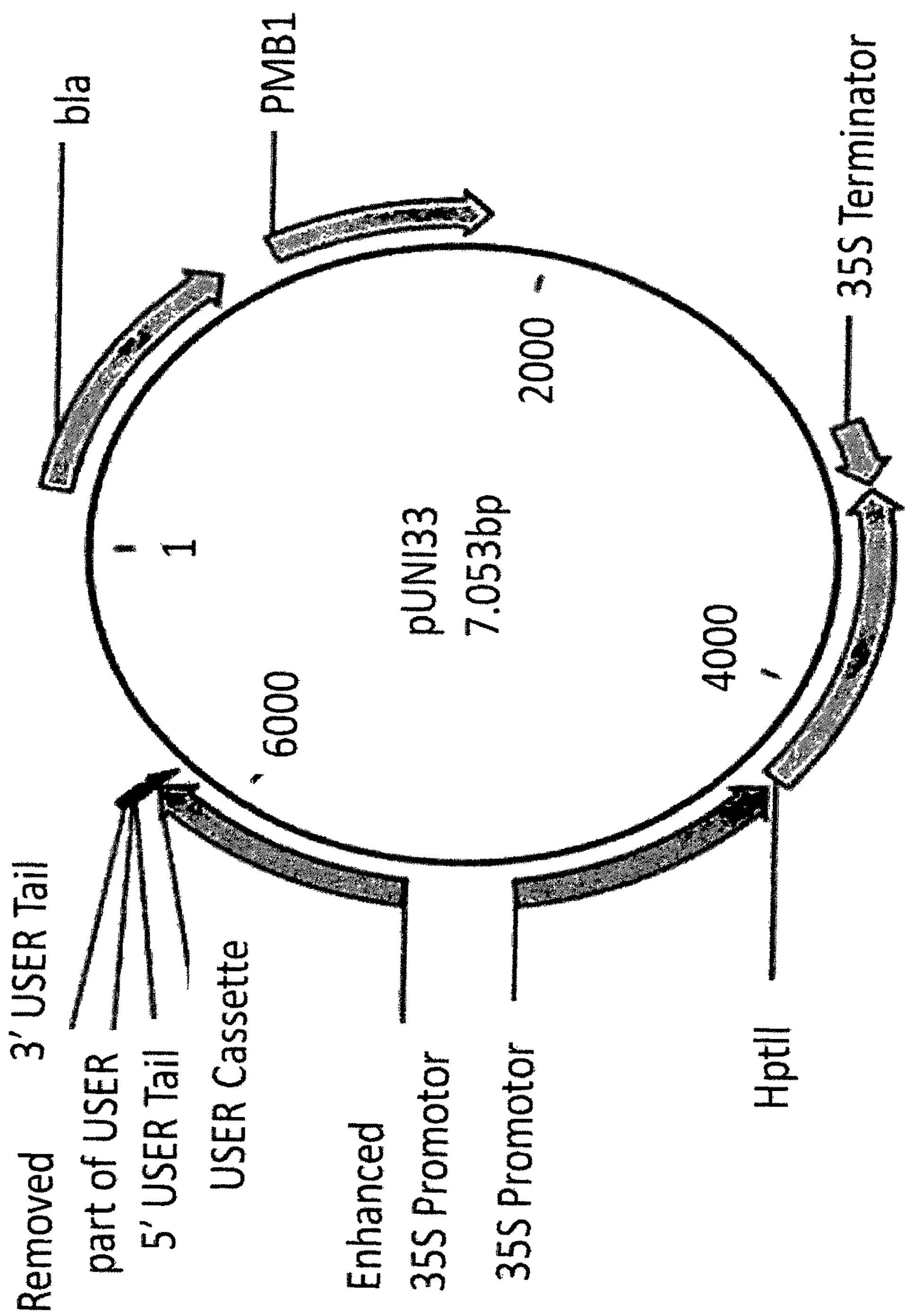

FIG. 11. Map of pUNI33: See also SEQ ID NO 8. pUNI33 is an artificial DNA sequence designed for biological research. The sequence was created on the basis of pLIFE33.

Figure 12:
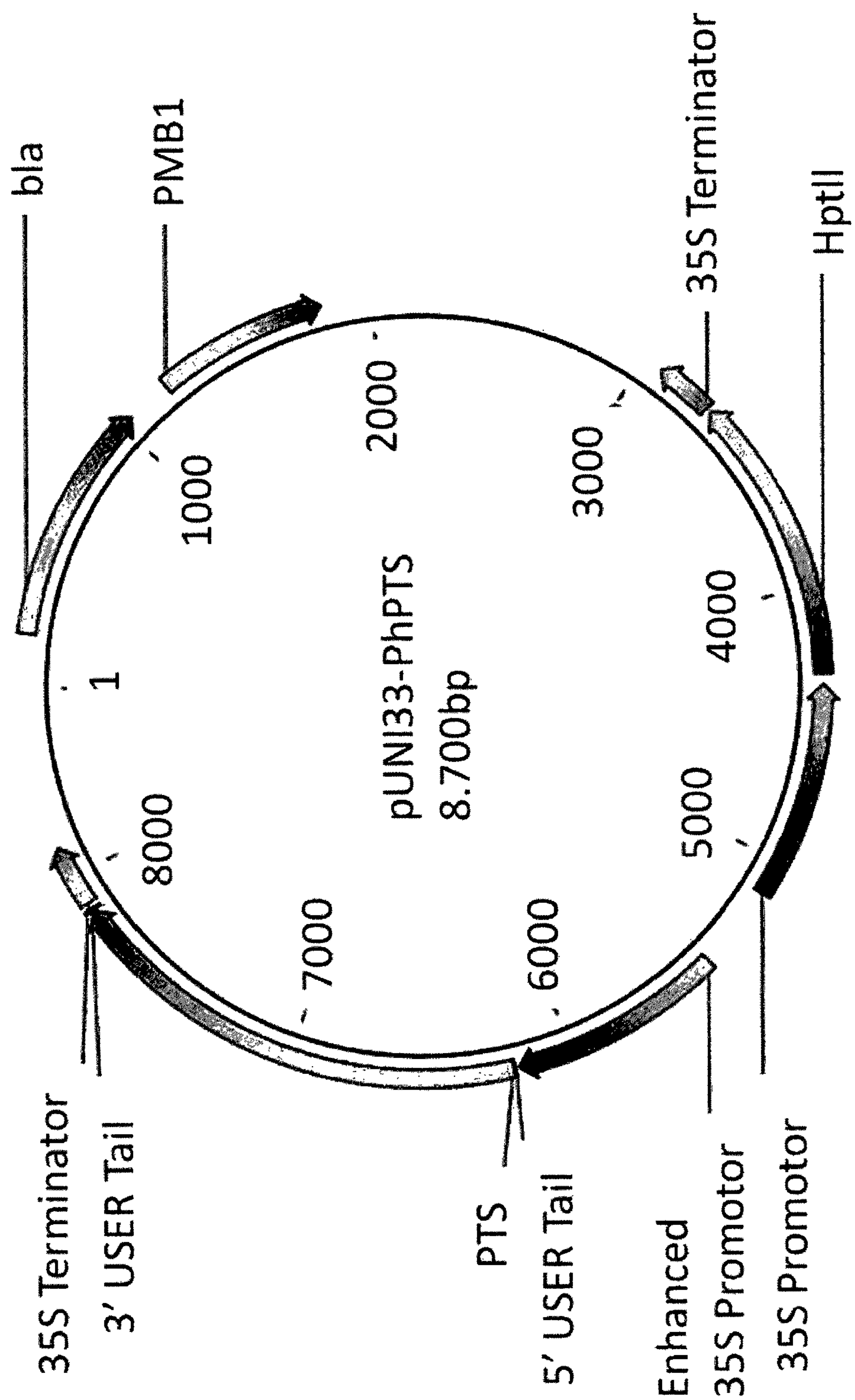

FIG. 12. Map of pUNI33 PTS: See also SEQ ID NO 9. pUNI33-PTS is an artificial DNA sequence designed for patchoulol biosynthesis in moss. The sequence was created on the basis of pUNI33.

Figure 13:
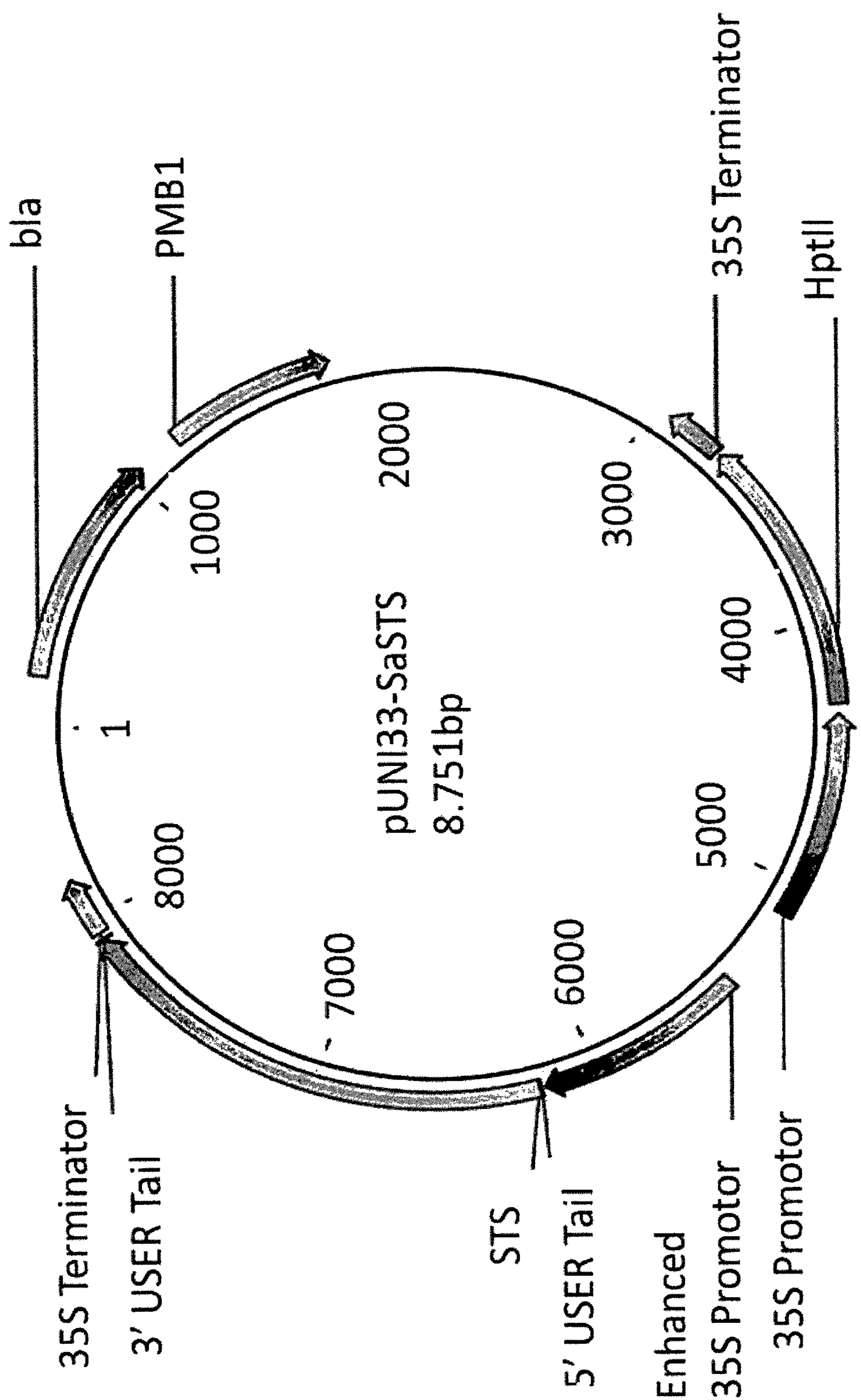

FIG. 13. Map of pUNI33 STS: See also SEQ ID NO 10. pUNI33-STS is an artificial DNA sequence designed for β-santalene biosynthesis in moss. The sequence was created on the basis of pUNI33.

Figure 14:
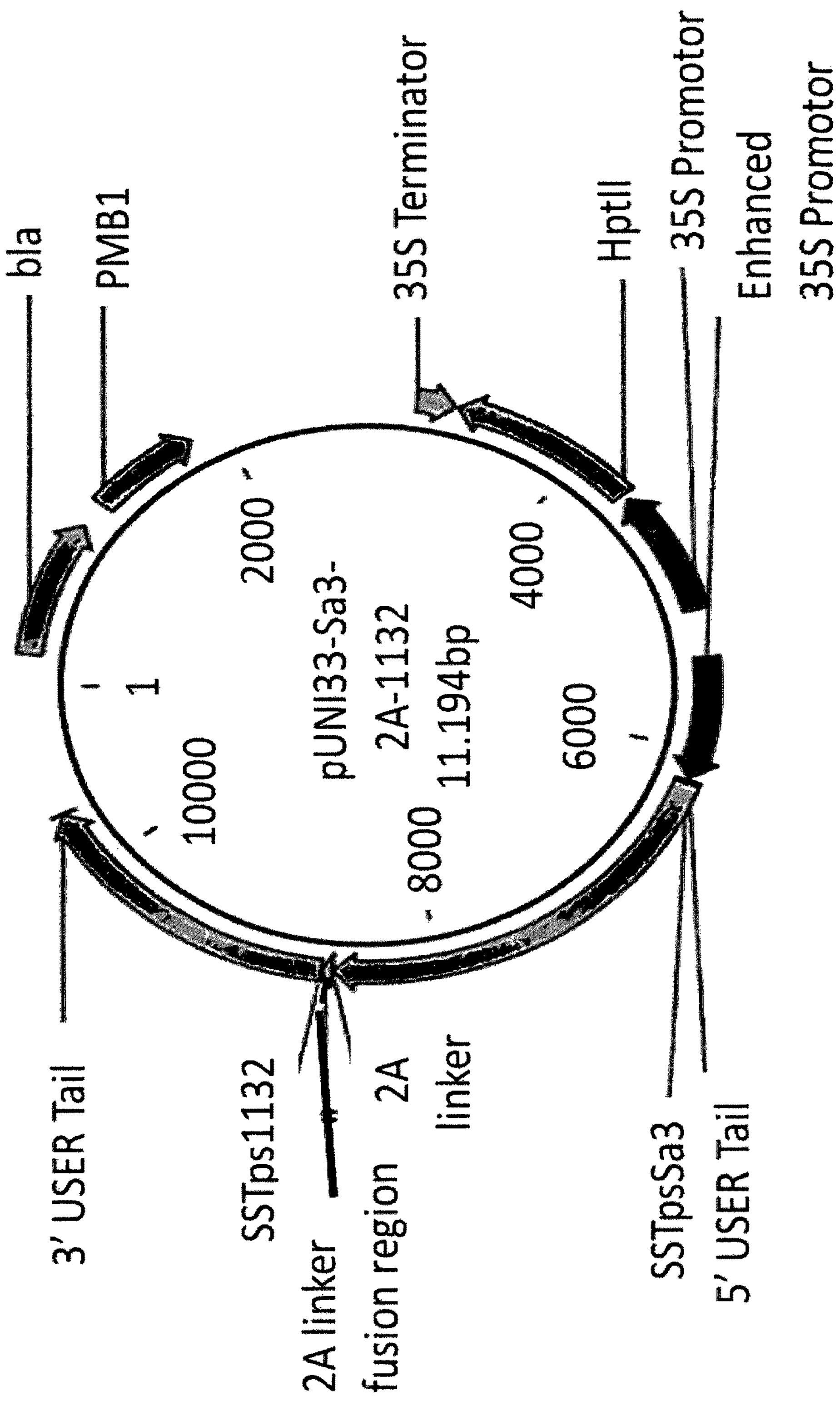

FIG. 14. Map of pUNI33-TPSsa3-2A-TPS1132. See also SEQ ID NO 11. pUNI33-TPSsa3-2A-TPS1132 is an artificial DNA sequence designed for sclareol biosynthesis in moss. The sequence was created on the basis of pUNI33.

Figure 15:
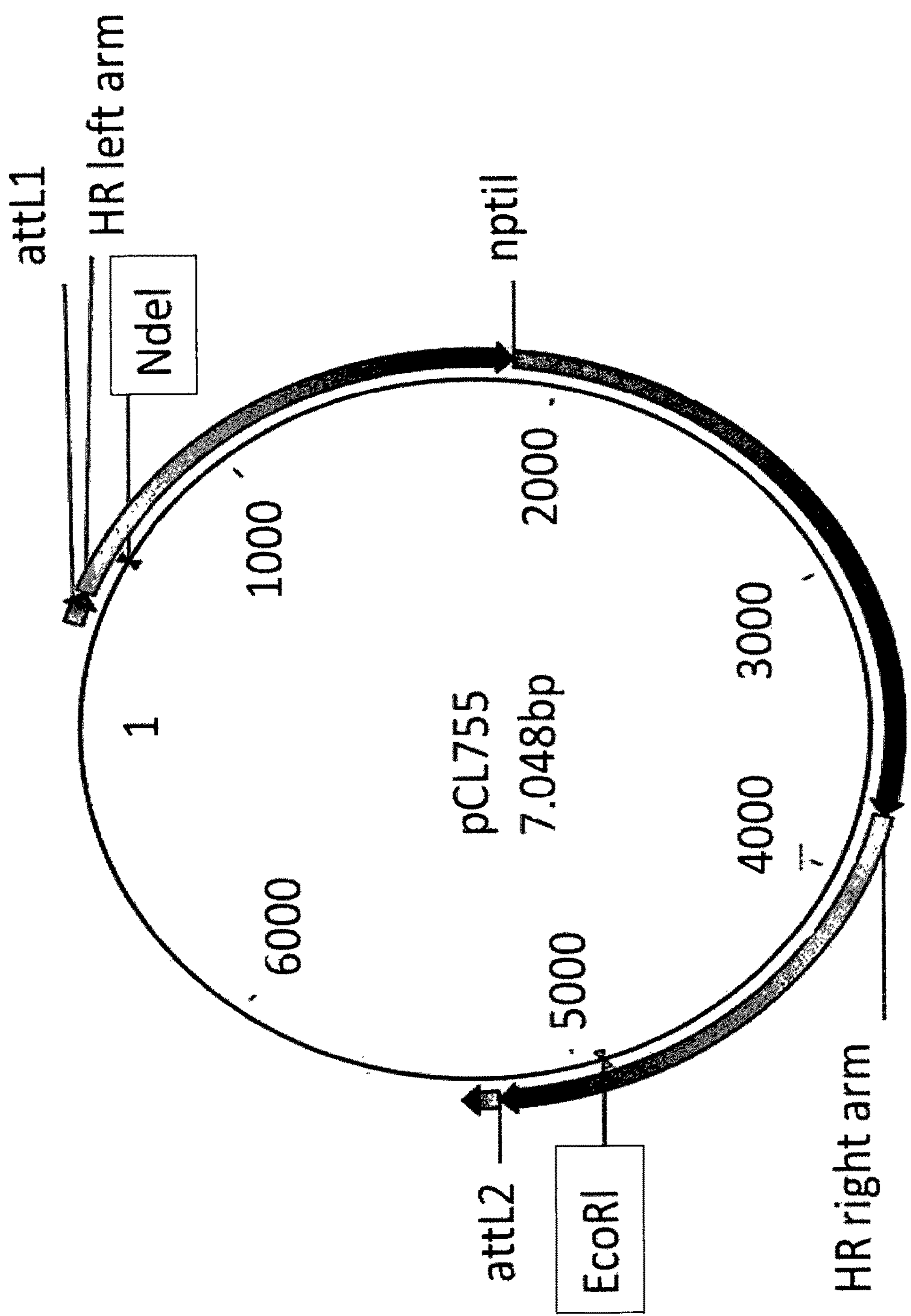

FIG. 15. Map of pCL755: See also SEQ ID NO 14. pCL755 is an artificial DNA sequence designed for disrupting the moss endogenous enzyme PpCPS/KS.

Figure 16:
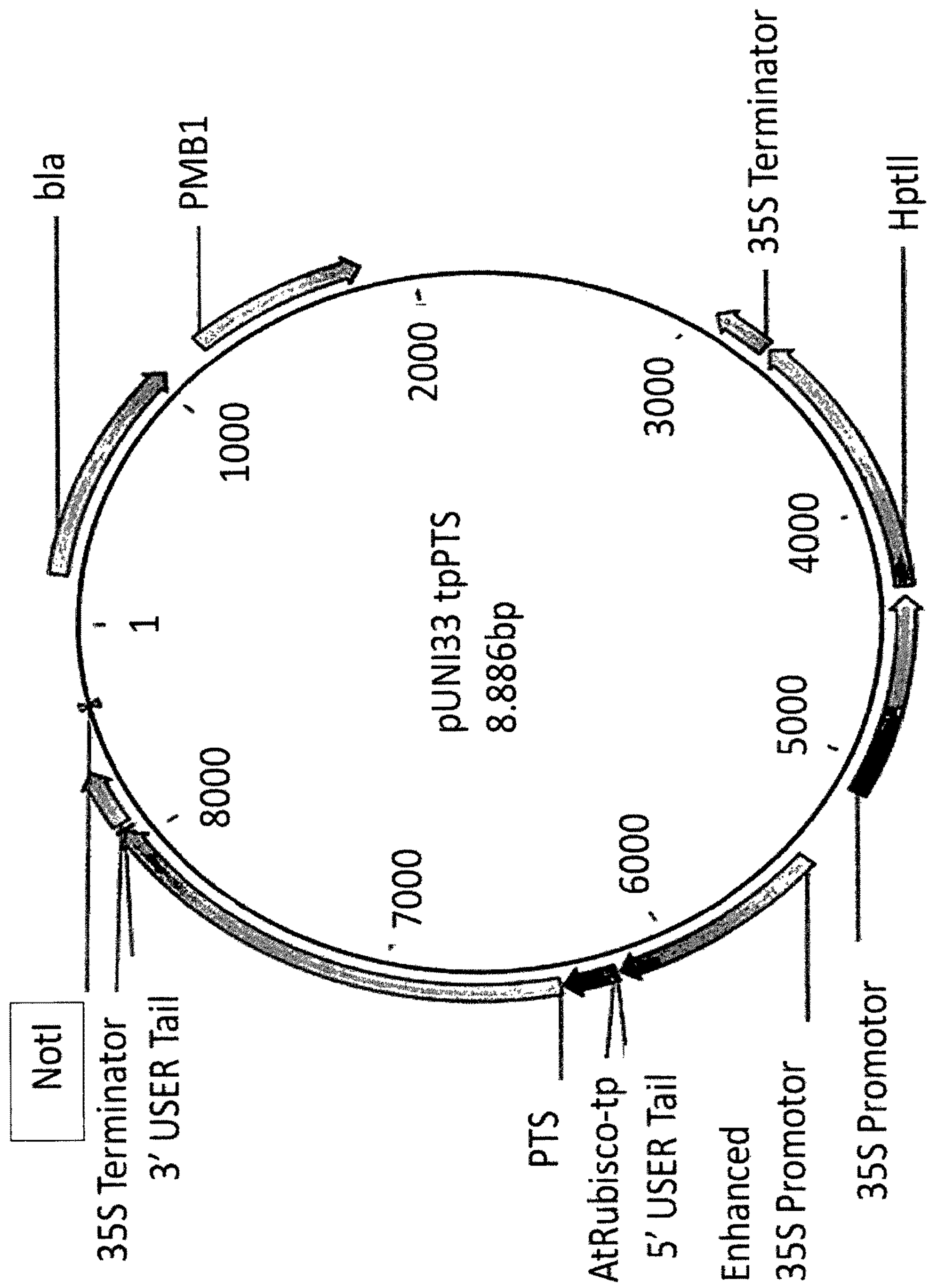

FIG. 16. Map of pUNI33 tpPTS: See also SEQ ID NO 15. pUNI33-tpPTS is an artificial DNA sequence designed for sclareol biosynthesis in moss. The sequence was created on the basis of pUNI33.

SEQ ID NO 1 is a gene having pathcoulol synthase activity (PTS). The gene is derived from the plant *Pogostemon cablin* and is equivalent to GenBank: AAS86323.1.

SEQ ID NO 2 is a gene having β-santalene synthese activity (STS). The gene is derived from the plant *Santalum album* and is equivalent to GenBank: ADO87000.1.

SEQ ID NO 3 comprises two genes having sclareol synthese activity (TPSsa3/TPS1132). The genes are derived from the plant *Salvia sclarea* and is equivalent to GenBank: AET21246.1/AET21247.1.

SEQ ID NO 6: DNA sequence of pJET1.2. pJET1.2 is a cloning vector from Thermo Scientific SEQ ID NO 7: DNA sequence of pLIFE33. pLIFE33 is a binary vector derived from the pCAMBIA1300u vector containing CaMV 35S promoter followed by empty standard PAC (USER: Uracil-Specific Excision Reagent) cassette SEQ ID NO 8: DNA sequence of pUNI33. pUNI33 is an artificial DNA sequence designed for biological research and was created on the basis of pLIFE33.

SEQ ID NO 9: DNA sequence of pUNI33-PTS. pUNI33-PTS is an artificial DNA sequence designed for biological research and was created on the basis of pLIFE33.

SEQ ID NO 10: DNA sequence of pUNI33-STS. pUNI33-STS is an artificial DNA sequence designed for biological research and was created on the basis of pLIFE33.

SEQ ID NO 11: DNA sequence of pUNI33-TPSsa3-2A-TPS1132. pUNI33-TPSsa3-2A-TPS1132 is an artificial DNA sequence designed for biological research and was created on the basis of pLIFE33.

SEQ ID NO 14: DNA sequence of pCL755. pCL755 is an artificial DNA sequence designed for disrupting the moss endogenous enzyme PpCPS/KS.

SEQ ID NO 15: DNA sequence of pUNI33-tpPTS. pUNI33-tpPTS is an artificial DNA sequence designed for biological research and was created on the basis of pLIFE33.

SEQ ID NO 16: DNA sequence of pUNI33-tpSTS. pUNI33-tpSTS is an artificial DNA sequence designed for biological research and was created on the basis of pLIFE33.

DETAILED DESCRIPTION OF THE INVENTION

In the following, the present invention is described in more detail. All individual features and details can be individually applied to each embodiment described.

Mosses, as such, are grouped as a single division within the plant kingdom, Bryophyta. Further, Bryophyta can be subdivided into eight classes; Takakiopsida, Sphagnopsida, Andreaeopsida, Andreaeobryopsida, Oedipodiopsida, Polytrichopsida, Tetraphidopsidaan and Bryopsida. Hence, by the term moss cells are meant moss cells belonging to Bryophyta and its subclasses. In one embodiment of the present invention, moss cells belonging to the class of Bryopsida are preferred, in particularly *Physcomitrella patens*.

A moss cell is according to the present invention meant to be "capable of producing FPP or GGPP" when it produces FPP or GGPP.

By the term, "polypeptide", is meant, unless specifically limited, an enzyme capable of catalyzing the synthesis of a terpene, starting from FPP or GPPP or from any intermediate products thereof provided by a polypeptide.

In the present context, a synthase is defined as enzyme (polypeptide) that catalyzes the synthesis of a specific or unspecific reaction whether or not the synthase uses nucleoside triphosphates during the reaction. This definition is in correspondence to the dictate of the Joint Commission on Biochemical Nomenclature (JCBN).

By the term, "terpene synthase", is meant, unless specifically limited, a polypeptide capable of catalyzing the synthesis of a sesquiterpene or a diterpene in the form of any of its stereoisomers or a mixture thereof, starting from FPP or GGPP, respectively.

By the term, "sesquiterpene synthase", is meant, unless specifically limited, a polypeptide capable of catalyzing the synthesis of a sesquiterpene in the form of any of its stereoisomers or a mixture thereof, starting from FPP.

By the term, "patchoulol synthase", is meant, unless specifically limited, a polypeptide capable of catalyzing the synthesis of patchoulol in the form of any of its stereoisomers or a mixture thereof, starting from FPP. Patchoulol may be the only product or may be part of a mixture of sesquiterpenes. Patchoulol is defined by the way of its structure, as represented by formula I in FIG. 6.

By the term, "β-santalene synthase" is meant, unless specifically limited, a polypeptide capable of catalyzing the synthesis of β-santalene in the form of any of its stereoisomers or a mixture thereof starting from FPP. β-Santalene may be the only product or may be part of a mixture of sesquiterpenes. β-Santalene is defined by the way of its structure, as represented by formula II in FIG. 6.

By the term, "diterpene synthase", is meant, unless specifically limited, a polypeptide capable of catalyzing the synthesis of a diterpene in the form of any of its stereoisomers or a mixture thereof, starting from the acyclic terpene precursor GGPP or from a diterpene diphosphate ester such as LPP.

By the term, "sclareol synthase", is meant, unless specifically limited, one or more polypeptides capable of catalyzing the synthesis of sclareol in the form of any of its stereoisomers or a mixture thereof starting from labdenediol diphosphate (LPP) or GGPP. Sclareol may be the only product or may be part of a mixture of diterpenes. Sclareol is defined by the way of its structure, as represented by formula III in FIG. 6.

For the purpose of the present invention, the term "nucleic acid molecules" and nucleic acid sequence" is meant to be the same, unless otherwise provided.

The percentage of identity between two nucleic acid sequences is a function of the number of nucleic acid residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of nucleic acid sequence identity can be achieved in various ways using computer programs and for instance publicly available computer programs available on the world wide web. Preferably, the BLAST program (Tatiana et al, FEMS Microbial Lett., 1999, 174:247-250, 1999) set to the default parameters, available from the National Center for Biotechnology Information (NCBI) website at ncbi.nlm.nih.gov/BLAST/b12seq/wblast2.cgi, can be used to obtain an optimal alignment of peptidic or nucleotidic sequences and to calculate the percentage of sequence identity.

According to the present invention, a moss cell can be genetically modified (transgenic moss cell) to provide for the preparation or accumulation of patchoulol, β-santalene, or sclareol. The transgenic moss cell may thus been transformed with a heterologous nucleic acid molecule encoding a sesquiterpene or diterpene synthase capable of performing the conversions required or involved in the metabolism of patchoulol, β-santalene, or sclareol. The transgenic moss cell may be transformed to comprise one or more heterologous nucleic acids molecules, SEQ ID NO 1, SEQ ID NO 2, or SEQ ID NO 3, encoding the synthase polypeptides, which may have a substantial effect on the production of the desired end compounds; patchoulol, β-santalene, and/or sclareol, or in the preparation of the relevant precursors in the transgenic moss cell.

A heterologous nucleic acid molecule encoding a terpene synthase or a combination of several hetereologous nucleic acid molecules encoding terpene synthases can be transformed into a moss cell, whereby the hetereologous nucleic acid molecules(s) can be modified either in their activity or number in the transgenic moss cell. A hetereologous nucleic acid molecule encoding a sesquiterpene or diterpene synthase can be isolated from any suitable organism, e.g. prokaryotes, plant cells, or eukaryotes, which comprises an endogenous nucleic acid sequence encoding a sesquiterpene or diterpene synthase.

A moss cell can be transformed with a heterologous nucleic acid molecule having at least about 70% sequence identity to a heterologous nucleotide sequence, SEQ ID NO 1, SEQ ID NO 2, or SEQ ID NO 3, which encodes a polypeptide having a specified enzymatic activity, or a complementary sequence to any of these sequences.

According to the present invention, a moss cell can be engineered by introducing a heterologous nucleic acid molecule encoding the sequence of SEQ ID NO 1 to express or overexpress a patchoulol synthase for the preparation of patchoulol starting from FPP.

According to the present invention, a moss cell can be engineered by introducing a nucleic acid molecule encoding the sequence of SEQ ID NO 2 to express or overexpress a β-santalene synthase for the preparation of β-santalene starting from FPP.

According to the present invention, a moss cell can be engineered by introducing a nucleic acid molecule encoding the sequence of SEQ ID NO 3 to express or overexpress a diterpene synthase(s) for the preparation of sclareol and/or intermediates thereof starting from GGPP.

Factors such as pH, cofactors, codon usage, and posttranslational modifications contribute to expression and functionality of the peptides.

*Physcomitrella* contains all the cellular compartments relevant for terpenoid biosynthesis found in higher plants, such as the endoplasmic reticulum (ER) and plastids. In addition, codon usage is conserved between *Physcomitrella* and higher plants such as *Arabidopsis thaliana*, as are several posttranslational modifications such as N-glycosylation [6-9]. Thus, *Physcomitrella* has strong potential to heterologously express functional enzymes with the same functionality as the endogenous higher plant [10]. This was demonstrated by successful expression of a diterpene synthase in *Physcomitrella* using the native plastid targeting signal and codons from *Taxus brevifolia* [11].

According to the present invention, a transgenic moss cell can be transformed so as to reduce an endogenous terpenoid compound. Reduction of an endogenous terpenoid compound may increase availability for engineered pathways associated with production of patchoulol, β-santalene, or sclareol compounds. Reduction of an endogenous terpenoid compound can increase production or accumulation of a target terpenoid compound in a moss cell. Thus, a transgenic moss cell may be transformed by reducing or eliminating one or more polypeptides in order to reduce the amounts of terpenoid compounds the transgenic moss cell can produce. Non-limiting examples for reduction or removal of terpene synthases would be mevalonate diphosphate decarboxylase, Mevalonate kinase, 4-hydroxyphenylpyruvate dioxygenase; geranylgeranyl pyrophosphate synthase; ent-Kaurene synthetase; farnesyl pyrophosphate synthase; etc.

In a preferred embodiment of the present invention, the transgenic moss cell belongs to the genus *Physcomitrella*. An example of a *Physcomitrella* moss that can be transformed to accumulate a terpenoid includes, but is not limited to, *Physcomitrella patens.*

*Physcomitrella* represents an ancient lineage of land plants, and its metabolic and chemical diversity is low compared to higher plants. This is illustrated by the number of cytochromes P450 (P450s) and UDP glycosyltransferases (UGTs) found in the genome. The genomes of *Arabidopsis thaliana* and *Oryza sativa* contain 246 and 343 P450s respectively, while the genome of *Physcomitrella* only contains 71 P450s [12]. Similarly the genome of *Physcomitrella* contains a low number of UGTs compared to other land plants [13]. The low number of P450s and UGTs found in *Physcomitrella* and the correspondingly lower chemical diversity reduces the risk of un-specific modifications by endogenous enzymes, through pathways used in higher plants for detoxification of xenobiotics. In addition to this *Physcomitrella* has a simple terpenoid profile and the genome of *Physcomitrella* only contains a single functional terpene synthase (TPS) [14]. This gene encodes a bifunctional copalyl synthase/kaurene synthase (PpCPS/KS), responsible for producing of ent-kaurene, a common precursor for the phytohormone gibberellic acid (GA) which is essential for growth and development in vascular plants [15]. Despite the importance of GAs in vascular plants, they have not been detected in *Physcomitrella* and ent-kaurene as well as ent-kaurenoic acid do not have a clear role in *Physcomitrella* [16, 17]. Although the role of kaurene-type molecules in *Physcomitrella* is unclear, they are produced in impressively large quantities, indicating a high native capacity to produce terpenoids [18]. Gene editing by efficient homologous recombination in *Physcomitrella* provides a very powerful tool for metabolic engineering [19]. Targeted knockouts of PpCPS/KS result in viable kaurene-free moss lines [20]. Knocking out moss terpenoid synthesis genes can be accomplished by homologous recombination, see e.g. [21]. In addition to having a terpenoid free-background, FPP or GGPP (the universal precursors for sesquiterpenes and diterpenes biosynthesis) could be redirected into heterologously expressed terpenoid pathways.

A heterologous nucleic acid molecule encoding a terpene synthase can be operably linked to a promoter for transformation of the moss cell. According to the present invention, the promoter can be any promoter functional in a moss cell.

There are several methods known in the art for the creation of transgenic plants and also in moss cells. These are well described in the art [21-23].

Protoplast transformation is the most commonly used method for *Physcomitrella* transformation, and is well described in the literature [21]. The method requires careful handling and regeneration of fragile protoplasts and must be done under sterile conditions. This method can be very efficient and yield a large number of stable transformants, however, several attempts may be needed to successfully recover stable *Physcomitrella* lines. Another robust alternative to e.g. PEG mediated transformation of protoplasts is biolistic transformation, i.e. direct gene transfer by particle bombardment may be utilized. In another embodiment, *agrobacterium*-mediated transformation may be utilized.

The DNA vectors used for transmation may additional contain various transit peptides targeting the peptides for specific cellular compartments, such as a transit peptides from *Arabidopsis thaliana*, RuBisCO.

In one embodiment, the transformation may be introduced into the cytosol, or into the chloroplasts, of the transgenic moss cell.

Direct gene transfer by particle bombardment provides an example for transforming plant tissue. In this technique a particle, or microprojectile, coated with DNA is shot through the physical barriers of the cell. Particle bombardment can be used to introduce DNA into any target tissue that is penetrable by DNA coated particles, but for stable transformation, it is imperative that regenerable cells be used. Typically, the particles are made of gold or tungsten. The particles are coated with DNA using either $CaCl_2$ or ethanol precipitation methods which are commonly known in the art. DNA coated particles are shot out of a particle gun. A suitable particle gun can be purchased from Bio-Rad Laboratories (Hercules, Calif.). Particle penetration is controlled by varying parameters such as the intensity of the explosive burst, the size of the particles, or the distance particles must travel to reach the target tissue. The DNA used for coating the particles may comprise an expression cassette suitable for driving the expression of the gene of interest that will comprise a promoter operably linked to the gene of interest. For example, moss transformation protocols are described in US App Pub No. 2003/0157592.

An important tool for transforming moss cells suitable to carry out the method of the invention in vivo is an expression vector comprising a nucleic acid molecule according to any embodiment of the invention. The skilled person is capable of selecting a suitable vector according to the expression system. In one embodiment, the expression vector includes the nucleic acid molecule of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid molecule of the invention.

The expression vector may be used in the methods for preparing a transgenic moss cell to comprise the heterologous nucleic acid molecules of the present invention, in the methods for producing polypeptides having a patchoulol synthase activity, β-santalene synthase activity, or sclareol synthase activity, or in the methods for preparing patchoulol, β-santalene, or sclareol, as disclosed further below.

Generation of variant nucleotides having the above required percent identities is common general knowledge. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, a person skilled in the art could generate a large number of nucleotide and/or polypeptide variants having, for example, at least 70%-99% identity to the reference sequence described herein and screen such for desired phenotypes according to methods routine in the art.

In one embodiment of the present invention, methods for metabolite production using simple and inexpensive photobioreactors as well as the basic tools for performing gene editing by homologous recombination are provided. Processes for culturing moss cells are known in the art (see e.g., Decker and Reski 2008; Knight et al. 2002 Molecular Plant Biology 2, 285-301; Cove et al. 2009 Emerging Model Organisms: A Laboratory Manual, Vol. 1. CSHL Press, Cold Spring Harbor, N.Y., USA, 2009). Thus, the culturing of a transgenic moss cell described herein can be carried out in accordance with such processes.

Patchoulol, β-santalene, or sclareol compounds prepared in a transgenic moss cell may be accumulated, converted to another terpenoid compound, or both. Generally, patchoulol, β-santalene, or sclareol compounds will have higher levels of accumulation if no additional terpenoid synthases with specificity for a terpenoid compound has been engineered into the moss cell.

In one embodiment, the essential oils produced by the transgenic moss cell may be isolated and/or purified further. The essential oils produced may decompose at high temperatures, and normal distillation is therefore not necessarily optimal. The essential oils may thus be purified by distillation, often by using steam. Other processes include expression or solvent extraction.

If the essential oils produced by the transgenic moss is intracellular, the transgenic moss cell may be disrupted by applying steam scalding, drying, high stress shear, or other suitable means.

In one embodiment steam distillation is preferred. By adding water or steam, the boiling points of the compounds may be depressed, allowing them to evaporate at lower temperatures, preferably below the temperatures at which the deterioration of the material becomes appreciable or neglible.

In one embodiment vaccume distillation is preferred. Alternatively, if the essential oils are very sensitive to heat, steam distillation can be combined with vacuum distillation.

After distillation the vapors are condensed as usual, usually yielding a two-phase system of water and the essential oils, allowing for decantation.

All methods described herein can be performed in any suitable order unless otherwise indicated or otherwise clearly contradicted by context. The use of any and all examples, or exemplary language provided with respect to certain embodiments herein is intended merely to better illustrate the invention and does not pose a limitation on the scope of the invention otherwise claimed.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

EXAMPLES

The following examples are intended to illustrate the various embodiments of the present invention. Thus, each individual example should not be construed as limiting the scope of the present invention. The examples provide techniques for establishing *Physcomitrella* as a heterologous moss cell for terpenoid biosynthesis. This includes two protocols for transformation and recovery of transgenic *Physcomitrella* lines as well as methods for metabolic profiling and characterization.

Plant Materials, Growth Conditions and Transformation

1. Wild type P. patens (Gransden ecotype) was obtained from the International Moss Stock Center at the University of Freiburg (see their website at moss-stock-center.org/) and a PpCPS/KS KO (bifunctional Copalyl Diphosphate/Kaurene Synthase KnockOut) moss line was created.

2. Growth conditions and transformation are described in detail [21].

Growth Media for *Physcomitrella patens*

1. Phy B media, modified from minimal media [24]: For one liter mix 800 mg $Ca(NO_3)_2$, 250 mg $MgSO_4 \cdot 7H_2O$, 12.5 mg $FeSO_4 \cdot 7H_2O$, 10 mL $KH_2PO_4$ buffer (25 g $KH_2PO_4$ per liter and adjusted to pH 6.5 with 4M KOH) and 0.25 mL trace element solution (110 mg $CuSO_4 \cdot 5H_2O$, 110 mg $ZnSO_4 \cdot 7H_2O$, 1228 mg $H_3BO_3$, 778 mg $MnCl_2 \cdot 4H_2O$, 110 mg $CoCl_2 \cdot 6H_2O$, 53 mg KI, 50 mg $Na_2MoO_4 \cdot 2H_2O$ per liter). The minimal medium was supplemented with 0.5 g ammonium tartrate per liter. The medium can be solidified with 0.7% (w/v) Agar A, and was sterilized by autoclaving at 121° C.

2. BCD media: For one liter mix 12.5 mg $FeSO_4 \cdot 7H_2O$, 10 mL solution B (25 g/L $MgSO_4 \cdot 7H_2O$), 10 mL solution C (25 g/L $KH_2PO_4$ adjusted to pH 6.5 with 4 M KOH), 10 ml solution D (101 g/L $KNO_3$), 1 mL trace element solution (614 mg $H_3BO_3$, 389 mg $MnCl_2 \cdot 4H_2O$, 55 mg $Al_2(SO_4)_3 \cdot K_2SO_4 \cdot 24H_2O$, 55 mg $CoCl_2 \cdot 6H_2O$, 55 mg $CuSO_4 \cdot 5H_2O$, 55 mg $ZnSO_4 \cdot 7H_2O$, 28 mg KBr, 28 mg KI, 28 mg LiCl, 28 mg and $SnCl_2 \cdot 2H_2O$ per liter). The medium was solidified with 0.7% (w/v) Agar A and was sterilized by autoclaving at 121° C. After autoclaving, 10 ml sterile 1M $CaCl_2$ solution was added (10 mM final concentration).

Example 1

DNA Expression Vectors Construction for PEG-Mediated Transformation

DNA expression vector containing Patchoulol synthase (PTS), SEQ ID NO 1, or β-santalene synthase (STS), SEQ ID NO 2, genes for random integration into the *Physcomitrella* genome was constructed as the following procedures:

1. pLIFE33 was double-digested using Psil and Pmel to generate the fragments containing the hygromycin-resistant cassette and the CaMV 35S promoter-driven operon containing the USER cassette.

2. The digested fragment was ligated into pJET1.2 in a blunted-end way and the resultant construct was referred to as pUNI33.

3. The PTS and STS genes were amplified by PCR using the primer pairs with USER-compatible overhangs, respectively.

4. The PTS and STS genes were integrated into the USER cassette sites of pUNI33 by USER cloning and referred to as pUNI33 PTS & pUNI33 STS, respectively.

The DNA expression vectors which targeted the PTS or STS enzyme into the plastids were constructed by adding the transit peptide of *Arabidopsis thaliana* RuBisCO enzyme at the 5' end of the PTS or STS gene by USER fusion. They were referred to as pUNI33 tpPTS & pUNI33 tpSTS.

The expression vector containing the two sclareol synthase (TPSsa3 and TPS1132, SEQ ID NO 3) genes was constructed as the following procedures:

1. pLIFE33 was double-digested by using Psil and Pmel to generate a fragment containing the hptII expression cassette, and the CaMV 35S promoter-driven expression cassette for gene-of-interest.

2. The digested fragment was ligated into pJET1.2 in a blunted-end way and the resultant construct was referred to as pUNI33.

3. The TPSsa3 and TPS1132 gene were amplified by PCR using the primer pairs with USER-compatible overhangs to fit pUNI33 cloning.

4. The two sclareol genes, which were linked by 2A (Ma, Chonglie and Mitra, Amitava 2002) through fusion PCR, were integrated to the USER cassette of pUNI33. The final construct was named pUNI33-TPSsa3-2A-TPS1132.

pCL755, which was used to knockout PpCPS/KS gene, was constructed as followings:

1. Part of PpCPS/KS gene was amplified by nested PCR (the sequence shown in the supplementary materials);

2. The PCR product was cloned into pDONR201 and digested with XhoI;

3. The nptII cassette was obtained from pMBL6 by XhoI digestion and ligated into the backbone vector from step 3;

4. The resulting vector was referred to as pCL755.

Example 2

PEG-mediated Transformation of *Physcomitrella*

Preparation of DNAs for Transformation

The DNA expression vectors were subjected to linearization before PEG-mediated transformation. pUNI33 PTS was taken here as an example and all the other vectors were subjected to the same treatment.

1. pUNI33 PTS was prepared from *E. coli* cultures using standard miniprep kits.

2. 200 ul (~30 μg) of pUNI33 was digested using the restriction enzyme NotI-HF overnight. The restriction enzyme was inactivated by heating at 60° C. for 20 minutes.

3. The next day, 1-2 μl of digestion mix was loaded on the agarose gel to check if the digestion was completed. Linearized pUNI33 PTS was precipitated by adding 0.7 volumes of room temperature isopropyl alcohol, mixing and centrifuging at 15 k rcf 4° C. for 30 minutes. The supernatant was carefully decanted, and the pellet was washed with 70% ethanol. DNA was centrifuged again at 15 k rcf for 15 minutes and the supernatant was carefully decanted. The pellet was air-dried and DNA was re-dissolved 30 μL sterile $H_2O$. Final DNA concentration should be between 600-1000 ng/μL.

Preparation and Transformation of Protoplasts

1. On the day of transformation, new PEG solution was prepared, and allowed to stand for 2 hours before use. The solution was subsequently sterilized by filtration by passing it through a 0.22 μm syringe filter.

2. 5-7 day old moss protonema tissue was harvested by scraping it off cellophane-overlaid agar plates and placed in a sterile 50 mL plastic tube. 1 mL of a 0.5% Driselase solution was prepared for every 40 mg tissue. The Driselase powder was dissolved in 8.5% D-mannitol, and sterilized using a syringe filter and *Physcomitrella* tissue was added subsequently. The mixture was incubated for 30-60 minutes with occasional inversion of tube until the tissue had been thoroughly digested.

3. The Driselase-treated tissue was poured through a sterile 100 μm stainless steel mesh screen, and the protoplasts were recovered in a sterile beaker. Undigested tissue and cellular debris do not pass through the mesh.

4. The protoplasts were centrifuged at 200 rcf for 5 minutes, with gentle breaking.

5. The supernatant was decanted using a serological pipette.

6. The pellet was re-suspended in protoplast wash solution using the same volume as driselase in step 2.

7. The steps 4 and 5 were repeated.

8. The protoplasts were re-suspended in half the original volume of 8.5% D-mannitol and the density was estimated using a hemocytometer.

9. The solution was centrifuged at 200 rcf for 5 minutes, and the supernatant removed. The pellet was re-suspended in sterile MMM solution yielding a protoplast concentration of 1.5-2×$10^6$ protoplasts/mL.

10. 30 μl (approximately 20-30 μg) of linearized DNA was added to the bottom of a 15 mL conical tube. 300 μL of protoplast suspension and 300 μL of sterile PEG solution were added and mixed with the DNA by flicking the tube.

11. The mixture was incubated at 45° C. in a water bath for 5 minutes followed by 5 minutes at room temperature.

12. The protoplast suspension was diluted 5 times with 300 μL of 8.5% D-mannitol, followed by an additional 5 times dilution with 1 mL of 8.5% D-mannitol.

13. The transformed protoplasts were centrifuged at 200 rcf with gentle braking for 5 minutes, and the supernatant was removed.

14. The protoplasts was resuspended in 500 μL 8.5% D-mannitol, and 2.5 mL of molten PRMT was added.

15. 1 ml of the protoplast suspension was added to a PRMB Petri dish overlaid with sterile cellophane. At least 3 plates were made from each transformation event.

16. The plates were sealed with 3M tape, and placed in a growth chamber under standard conditions.

17. The protoplasts were allowed to regenerate their cell walls for 5-7 days, and then the cellophane and regenerating plants were to the selective media and selection of positive transformants as proceeded as described in section 2.7.

Example 3

Selection Procedure in Order to Obtain Stable Moss Lines

1. Cellophane discs with transformed moss were transferred onto solid PhyB media with 30 μg/mL hygromycin and incubated for two weeks under standard conditions.

2. The cellophane discs were transferred with recovered transformants to solid PhyB media and incubated for another 2 weeks for relaxation. Unstable or transient transformants lose the plasmid and the ability to survive on selective media in this period.

3. Step 1 and 2 was repeated. Moss lines obtained after two rounds of selection were considered to be stably transformed moss lines.

Example 4

Metabolite Profiling of Stable Moss Lines Using GC-MS

Analysis of Volatile Sesquiterpenoid Products 20 mL sterile GC vials were used to analyze the volatile metabolites using the HS-SPME (Headspace-Solid Phase Micro Extraction) technique.

1. 3 mL solid Phy B media was added into each 20 mL GC vial and inoculated with moss.

2. The GC vials were incubated for 2-3 weeks in the growth chamber as described.

3. The volatiles in the headspace were sampled on a SPME fiber for 30 minutes and then analyzed by GC-MS.

HS-SPME Conditions

A 23 Gauge, 50/30 μm, DVB/CAR/PDMS SPME fiber (Sigma 57298-U) was used to sample the volatiles. The fiber was penetrated into the 20 mL GC vial and exposed in the headspace for 30 min at the room temperature, followed by 1 min desorption in the injection. The GC-MS is described below.

Quantification of Volatile Sesquiterpenoid Using Dodecane Overlayed Liquid Cultures 1. A 100 mL Erlenmeyer flask containing 20 ml BCD media was inoculated with 2 mL of one week old plate blended for 30 seconds in 10 mL sterile water. The flasks were sealed with a sterile flask sponge cap. After 4 days 1.5 mL (7.5 v/v) dodecane was added under sterile conditions, and cultivation was continued for 2 weeks.

2. 10 ml of culture containing dodecane was centrifuged at 4000 rpm for 5 min in a glass tube.

3. 100 μL of dodecane was diluted in 900 μL hexane and analyzed by GC-MS.

4. The concentrations of the metabolite of interest in each moss line were calculated based on the external authentic standard and the dry weight of the moss. Each moss line was tested in triplicate.

GC-MS Analysis Conditions

The GC-MS analysis was performed with the following conditions: Injection volume was 1 μl using a splitless injection mode, and the injector temperature was 250° C. The analysis was performed in pressure hold mode with He as carrier gas at 160.0 kPa. The coloumn was a SLB®-5 ms capillary GC column (Sigma 28466-U, 14 m [L]×0.10 mm [D]×0.10 μm [thickness]). The GC temperature program was: 0-3 min 45° C., 10° C./min to 300° C. and hold 5 min, the interface temperature was 150° C., and the MS-ion source temperature 260° C., the voltage was 70 eV, relative to tuning. The MS analysis was performed with a scan range from m/z 50 to m/z 350, a solvent cut time at 5 min, and with a threshold of 100.

Quantification of Sclareol 1. 300 mg fresh weight of moss was loaded into a Crimp neck vial N11 (11.6×32 mm, usage volume 1.5 ml).

2. 1 ml ethyl acetate was added, and extraction was performed for 2 hours, using ultrasonic treatment to facilitate the extraction.

3. The EtOAc was filtrated and transferred in to a new vial, then analysed on the GC-MS as described.

4. The moss left in the first vial was dried at 75° C. for 48 hours, and the dry weight was established.

5. The concentrations of sclareol in each moss line were calculated based on the external authentic standard and the dry weight of the moss.

Example 5

Cultivation of *Physcomitrella*

Cultivation of *Physcomitrella* was performed according to standard protocols [21]. All work with *Physcomitrella* was done under sterile conditions using sterile materials and standard sterile techniques. All moss handling was performed with sterile forceps.

Cultivation on Solid Media Using Petri Dishes.

1. A lump (approximately 2-5 mm in diameter) of *Physcomitrella* gametophyte tissue was placed on a Petri dish with Phy B solid media. The plates were sealed with 3M surgical tape 2. The cultures were incubated at standard conditions in a 25° C. growth chamber.

Cultivation on Solid Media Overlaid with Cellophane Discs.

The growing *Physcomitrella* on top of cellophane the tissue did not adhere to the solid agar and was therefore easy to handle.

1. A 9 mm Petri dish filled with Phy B solid media was overlayed with a sterilized disc of cellophane. The lid was closed to let the cellophane disc absorb moisture for 10 min, then straightened to avoid air bubbles and wrinkles.

2. A lump of approximately one week old tissue (around 10 mm in diameter) was added to 10 mL sterile water in a 50 mL tube and homogenized using a Polytron tissue disruptor.

3. A serological pipette was used to transfer 1-3 mL of homogenized suspension to Petri dishes with cellophane overlaid Phy B media and the plates were carefully dried uncovered.

4. The plates were sealed carefully with surgical tape and the cultures were incubated one week in a growth chamber at standard conditions.

5. The tissue was harvested by scraping it off the cellophane.

6. For further biomass generation step 1-5 was repeated using a plate of protonemal tissue blended in 10 mL $H_2O$.

Cultivation in Liquid Medium Using Simple Medium Scale Photo-Bioreactors.

1. Tissue from a plate of one week old protonemal tissue was added to 5-10 mL sterile water and homogenized by a Polytron.

2. The solution was inoculated in 50-100 mL BCD liquid media. In addition to BCD media, liquid Phy B and KNOP media may be used for liquid growth. In order to obtain very high growth rates approximately 1.5% of $CO_2$ may be supplemented to the moss culture and the light intensity may be increased.

3. The flask using a sterile BugStopper was sealed and incubated for up to 3 months on a rotary shaker in a growth chamber.

4. The tissue was homogenized every week.

Results

The Transgenic Moss Lines Producing Patchoulol 29 transgenic lines producing patchoulol were obtained after 2 rounds of selection.

Among them, 5 transgenic lines producing the highest amounts of patchoulol were selected according to HS-SPME results. The volatile metabolites were captured by dodecane overlays (FIG. 2) and the yields of patchoulol were quantified.

5 transgenic moss lines with plastid-targeted PTS enzyme were also obtained and they showed the identical volatile metabolites profile to that of cytosolic-targeted ones. 3 transgenic moss lines with plastid-targeted PTS enzymes in the PpCPS/KS KO (bifunctional Copalyl Diphosphate/Kaurene Synthase KnockOut) moss line were also obtained and they showed the identical volatile metabolites profile to that of cytosolic-targeted ones. 16 and 10 stable lines were obtained with PpCPS/KS gene knockout in WT-PTS35 and WT-tpPTS9, respectively. Patchoulol was identified and no kaurene products were detected using HS-SPME analysis.

The Transgenic Moss Lines Producing β-Santalene 2 transgenic lines producing β-santalene with cytosolic STS enzyme in the WT moss line were obtained (FIG. 4).

1 transgenic line producing β-santalene with cytosolic STS enzyme in the PpCPS/KS KO line was obtained and the volatile metabolites profile was identical to that in the WT line.

1 transgenic line producing β-santalene with plastidic STS enzyme was obtained.

The Transgenic Moss Lines Producing Sclareol 2 transgenic lines producing Sclareol were obtained both with WT and PpCPS/KS KO background line. The stable transgenic lines were named WT-pUNI33-TPSsa3-2A-TPS1132 and KO-pUNI33-TPSsa3-2A-TPS1132 respectively. The volatile metabolites profile demonstrated sclareol production in transformed moss (FIG. 7).

A time-course measurement of scalreol production in KO-pUNI33-TPSsa3-2A-TPS1132 was conducted and the yield was dependent on moss age, with the highest production around 22 days after subculture to yield 280 μg/g dry weight (FIG. 8).

Example 6

The DNA expression vector containing PTS (patchoulol synthase gene, SEQ ID NO 1) or STS (α/β-santalene, SEQ ID NO 2) gene for random integration into the *Physcomitrella* genome was constructed as the following procedures:

1. pLIFE33 was double-digested using PsiI and PmI to generate the fragments containing the hygromycin-resistant cassette and the CaMV 35S promoter-driven operon containing the USER cassette.
2. The digested blunt-end fragment was ligated into pJET1.2 and the resultant construct was referred to as pUNI33.
3. The PTS and STS genes were amplified by PCR using the primer pairs PTS-F & R and STS-F & R with USER-compatible overhangs, respectively.
4. The PTS and STS genes were integrated into the USER cassette sites of pUNI33 by USER cloning and referred to as pUNI33 PTS & pUNI33 STS, respectively.

The DNA expression vectors, which targeted the PTS or STS enzyme into the plastids, were constructed by adding the transit peptide of *Arabidopsis thaliana* RuBisCO small subunit enzyme at the N-terminus of the PTS or STS enzyme by USER fusion. They were referred to as pUNI33 tpPTS & pUNI33 tpSTS.

pCL755, used to knockout PpCPS/KS gene, was constructed as followings:

1. A 3 kb fragment of the PpCPS/KS was amplified by PCR using the primers oCL252 and oCL254 and the nested primers oCL253 and oCL255 including attB1 and attB2 overhangs;
2. The PCR product was cloned into pDONR201 and digested with XhoI;
3. The nptII cassette was obtained from pMBL6 by XhoI digestion and ligated into the backbone vector from step 3;
4. The resulting vector was referred to as pCL755.

The primer sequences and vector descriptions are shown in Table S1 and S2.

Before PEG-mediated transformation, the vectors were linearized using NotI-HF (New England Biolabs), concentrated by isopropanol and approximately 20 μg of DNA was prepared. For CPS/KS disruption, the vector pCL755 was double digested by EcoRI and NdeI and concentrated by isopropanol as well. Linearized DNA was subsequently mixed with moss protoplasts using the PEG-mediated transformation method. After 5-7 days of regeneration, the moss tissues were transferred to antibiotic selection to recover stable transgenic lines using appropriate antibiotics.

The volatile metabolites profile of all the transgenic lines was determined by HS-SPME (Headspace-Solid Phase Micro-Extraction) and GC-MS (Gas Chromatography-Mass Spectrum) analysis. Specification of HS-SPME and GC-MS for qualitative study is described above.

The volatile metabolites were putatively identified by comparing the mass spectra in the NIST and WILEY library and their retention index (RI). Quantification of volatile metabolites was conducted in liquid culture overlaid with dodecane (Sigma-Aldrich).

Fresh moss tissues were blended and inoculated (each inoculum approximately 10 mg DW) into 50 ml PhyB medium in 250 ml shake flasks, and cultivated on a rotary shaker at standard conditions. After 2 weeks, the media together with moss tissues were extracted using 50 (for the PTS lines) or 25 ml heptane (for the STS lines) by hand shaking for 1 min. After phase separation, 1 ml of the organic phase was taken into the GC vial and 1 ul was injected into GC-MS. Quantification of patchoulol and α-santalene was achieved based on a standard curve.

The moss tissue was filtered using a vacuum pump and dried at 60° C. overnight, and the dry weights were measured the next day.

GC-MS analysis was performed on a GCMS 7890/5975C (Agilent) equipped with a LTM column module (DB-1MS) (10 m×0.18 mm i.d.×0.18 μm). Samples (1 μl) were injected with a split ratio of 25:1 into LTM (DB-1 MS) column using the following temperature program: 50° C. (held for 1 min), 50-320° C. (30° C./min, held for 1 min), and the total time is 11 min (2 min solvent delay). The oven temperature was 200° C. (held for 11 min). The injector temperature of GC was 250° C. The ion source temperature of the mass spectrometer was 230° C. and the transfer line temperature was set at 250° C. Helium was used as carrier gas at constant flow rate 0.7 ml/min. Data were acquired by EI+ with SIM (Selected Ion Monitor) mode. The detail of SIM method to quantify patchoulol and α-santalene was as follows:

RT (retention time) 2.00 to 6.00 min diagnostic ions 98, 138, 161, 222 were selected to monitor patchoulol and 93, 94, 107, 121, 122, 204 for a/β-santalene;

RT 6.00 to 11.00 min diagnostic ions 232, 257, 272, 290 were selected to monitor 16α-hydroxykaurane.

16α-hydroxykaurane was quantified in approximate level according to the external standards (patchoulol or α-santalene) curves. The statistical significance was calculated using Student's t-test defining the significant level as P value<0.05.

The transcripts of the regulatory genes in the terpenoid biosynthetic pathway were quantified by RT-qPCR (Real Time-quantitative PCR). Three biological replicates were selected for each 2-week old transgenic line and their total RNAs were extracted using Spectrum™ Total RNA Kit (Sigma) and the concentrations and quality (A260/A280>1.8; A260/A230>2.0) were measured using Nanodrop 1000D.

The first-strand cDNA was subsequently generated using iScript™ cDNA synthesis Kit (Bio-Rad). cDNA was used as templates in RT-qPCR using the dyNAmo SYBR Green qPCR kit (Thermo Scientific).

*P. patens* actin2 (NP_188508) was used as the reference gene here, and the transcripts level was calculated using the $2^{-\Delta\Delta t}$ method. The nucleotide sequences of the qPCR primers are listed in Table S3 in the supporting information.

Results:

The Metabolite Profile of the Cytosolic PTS Lines.

DNA for cytosolic expression of PTS was introduced into wild type moss by random integration. After two rounds of antibiotic selection, 44 independent stable lines named WT-PTS1 to WT-PTS44 were obtained. Of these, 29 emitted the patchoulol and other sesquiterpene products as analyzed by HS-SPME and GC-MS analysis (FIGS. 18 and 19). In addition to the native diterpene metabolites in the moss, at least 16 different sesquiterpene products including patchoulol were detected in the headspace (FIGS. 18 and 19). Among them, seychellene was the most abundant volatile followed by α-patchoulene and α-guaiene.

Five cytosolic PTS lines, WT-PTS10, 14, 19, 27 & 35, were subsequently selected according to their relatively larger peak area of seychellene for metabolite quantification. Patchoulol was confirmed to be the major sesquiterpene product in the WT-PTS lines in liquid cultures overlaid with dodecane along with several other sesquiterpene hydrocarbons detected (FIGS. 18 and 19). The five selected cytosolic PTS lines produced 0.2-0.8 mg patchoulol/g dry weight (DW), cf. Table S4. The amount of the native diterpene metabolite 16α-hydroxykaurane was significantly reduced compared to the WT moss, with the exception of the line WT-PTS10 (Table S4).

The Metabolites Profile in the KO Lines.

The CPS/KS gene was disrupted in both WT and WT-PTS35 to augment the IPP pool and redirect the carbon flux from native diterpenes to sesquiterpene patchoulol production in *P. patens*.

The CPS/KS knockout line designated as KO was first constructed by disrupting the corresponding gene CPS/KS by homologous recombination. Using KO as the background line, one transgenic line named KO-tpPTS1 was obtained by introducing the plastid-targeted PTS enzyme. However, the yield of patchoulol in KO-tpPTS1 was below detection (<1 μg/g DW) compared to 0.02 mg patchoulol/g DW in WT-tpPTS2, one of the plastidic PTS lines in the WT background (Table S4). To eliminate the positional effect of random integration events, the effect of CPS/KS disruption on patchoulol production was evaluated by knocking out CPS/KS in the previously characterized line WT-PTS35.

The CPS/KS gene was knocked out in the cytosolic PTS line using the identical approach as previously described. The headspace volatile analysis identified one line from the transformants, which showed presence of patchoulol but absence of the diterpene metabolites, PTS35-KO. However, the yield of patchoulol was apparently reduced to 0.4 mg/g DW in PTS35-KO (Table S4). Disruption of CPS/KS in one of the plastidic PTS lines, WT-tpPTS2, was also attempted but no transgenic lines with a positive chemotype lacking kaurenoids was obtained. In summary, both studies showed that disruption of the CPS/KS gene neither improved the patchoulol yield in the cytosolic nor in the plastidic PTS line.

The Metabolites Profile of the Plastidic PTS Lines.

PTS enzyme was targeted into the moss plastids by fusing the transit peptide of *Arabidopsis* RuBisCO small subunit at the N-terminus of the enzyme. Both the WT and KO line were used as the background lines to test the effect of the plastidic targeting of the PTS enzyme on patchoulol production. Besides the native diterpenes and heterologous sesquiterpene products (including patchoulol), the headspace volatiles analysis showed emission of monoterpene products in both the WT and KO plastidic lines (FIG. 20).

Genotyping of the Cytosolic PTS Lines.

In the cytosolic PTS lines, the PTS gene transcripts level in the five WT-PTS lines were quantified by RT-qPCR, cf. Table G.

Five WT-PTS lines showed in general very high PTS transcript level, among which WT-PTS27 was the highest. WT-PTS27 was about 10-100 folds higher than the endogenous terpenoid biosynthetic genes, indicating the high expression activity of the PTS gene in the moss genome (Table S6). Moreover, the expression level of the HMGR gene was investigated and, it was found that this rate-limiting gene in the MEV pathway was up-regulated in all the five WT-PTS lines. However, unlike HMGR, both FPS and SQS showed differentiated expression profiles in the five WT-PTS lines. The FPS expression was strongly reduced in WT-PTS10 and WT-PTS14, whereas highly overexpressed in the rest of the three lines WT-PTS19, 27 and 35. Similarly for SQS, its expression was decreased in WT-PTS10 and 14, but remained constant or slightly increased in WT-PTS19, 27 and 35. With respect to the MEP pathway and its downstream routes towards diterpenes synthesis, the genes DXS, DXR, GGPS, and CPS/KS were examined in transcripts level. DXS and GGPS showed a very similar expression pattern with each other in the 5 cytosolic PTS lines. Intriguingly, DXS and GGPS were down-regulated in the three higher patchoulol-producers WT-PTS19, 27 & 35, in contrast to the slight up-regulation in WT-PTS10 & 14. In addition, DXR either remained stable or was overexpressed in the 5 cytosolic PTS lines. Regarding to the bi-functional diterpene synthase gene CPS/KS in *P. patens*, it showed much higher expression level in WT-PTS10 than the WT line, while the rest four lines remained either constant or strongly reduced.

Genotyping of the CPS/KS KO Lines.

Disruption of the CPS/KS gene was conducted to redirect the diterpenes metabolism to the sesquiterpenes production in *P. patens*, cf. Table G.

One of the patchoulol-producing moss lines WT-PTS35 was selected to disrupt the CPS/KS gene by homologous recombination, PTS35-KO. The genotyping work confirmed the reduction of the CPS/KS transcript level in PTS35-KO compared to WT but was slightly increased against WT-PTS35, probably because the qPCR primers of the CPS/KS gene annealed to the 5'-UTR. The genomic diagnostic work showed that a 2-kb PCR product was successfully amplified when using primer pair oSSB94 & oSSB95, but no PCR product was amplified when the primer pair oCL77 and oCL252 was used, indicating a possible unexpected integration way of the nptII cassette into the moss genome of PTS35-KO. Regarding the change in transcripts level, all the regulatory genes in the MEV pathway and its downstream route, PTS, HMGR, FPS and SQS, were transcriptional down-regulated. Unlike the expression pattern of the regulatory genes in the MEV pathway, the expression patterns in the MEP and its downstream pathway seemed to be differentially regulated. In PTS35-KO, the activity of DXS and GGPS was significantly up-regulated but the transcript level of DXR was obviously reduced, the same trend as CPS/KS disruption in WT. A similar phenomenon was observed in GGR and PSY, which catalyze the first committed step in phytol and carotenoid synthesis, respectively. GGR activity was decreased but PSY was boosted in PTS35-KO, indicating the rebalance of different terpneoid products from the MEP and its downstream pathway in *P. patens*.

Genotyping of the Plastidic PTS Lines.

Several plastidic PTS lines in WT or KO background were obtained, and the genetic background of two of these lines, WT-tpPTS2 and KO-tpPTS1, were investigated in terms of the regulatory gene transcripts level, cf. Table G.

PTS transcript levels of WT-tpPTS2 and KO-tpPTS1 were found to be at the same magnitude as some cytosolic PTS lines. For example WT-PTS14. HMGR, FPS and SQS transcripts level were all down-regulated after the PTS enzyme was targeted into the plastids of the WT line, while in contrast they were all up-regulated after the PTS enzyme was targeted into the plastids of the KO line. Likewise, DXS, DXR and GGPS were all down-regulated, when the PTS enzyme was targeted into the plastids of the WT line, while in contrast, they were stable or overexpressed when the PTS enzyme was targeted into the plastids of the KO line. In addition, CPS/KS, GGR and PSY were all down-regulated in WT-tpPTS2, being especially significant for GGR, while no significant GGR and PSY transcripts level change was observed between KO and KO-tpPTS1. Very low amounts of CPS/KS transcript level was detected in KO and KO-tpPTS1, i.e. the lines where the CPS/KS gene was assumed to be disrupted. This could also be ascribed to the 5'-UTR annealing sites of the qPCR primers of the CPS/KS gene.

The Metabolites Profile of the Cytosolic STS Lines.

STS (α/β-santalene synthase) gene from the sandalwood *S. album* was introduced into the moss genome by random integration. Four stable transgenic lines WT-STS3, 6, 11 & 13 were obtained, and HS-SPME coupled with GC-MS analysis showed that α-santalene, α-bergamotene, epi-β-santalene and β-santalene were emitted into the headspace besides the endogenous diterpene metabolites (FIG. 21). The yields of α/β-santalene were—attempted to be—quantified in liquid cultures overlaid with dodecane, but none of the four transgenic lines appears to produce sufficient amounts of detectable α/β-santalene, indicating that the culture produced about or below 1 μg β-santalene/g DW in *P. patens* (Table S5). However, the 16α-hydroxykaurane amounts varied a lot between the four transgenic lines (Table S7). WT-STS3 showed same level of 16α-hydroxykaurane as WT, but the rest three lines WT-STS6, 11 and 13 produced less amounts of 16α-hydroxykaurane (Table S7). Especially in WT-STS11, the amount of 16α-hydroxykaurane was reduced to 0.05 mg/g DW (Table S7).

The Metabolites Profile in the CPS/KS-KO STS Lines.

One cytosolic STS line in the KO background was obtained, KO-STS1. The volatile metabolites analysis confirmed emission of α/β-santalene into the headspace and no detection of native diterpene products in KO-STS1 (data not shown). The yield of α/β-santalene was investigated as well but again it was not sufficient high to reach the detectable level (Table S5).

The Metabolites Profile of the Plastidic STS Lines.

Like the PTS enzyme, the STS enzyme was targeted into the plastids of the WT line using the transit peptide of *Arabidopsis* RuBisCO small subunit. Four plastidic STS lines were obtained, and the HS-SPME GC-MS analysis showed that one of the four lines, named WT-tpSTS1, emitted monoterpenes besides the sesquiterpene products and the native diterpene metabolites (FIG. 22). However, 3 additional plastidic STS lines WT-tpSTS8, 9, & 10 produced low amounts of α/β-santalene and no monoterpenes was detected (data not shown). The yield of α/β-santalene in WT-tpSTS1 was subsequently determined to be 0.039±0.008 and 0.035±0.001 mg/g DW respectively, which were the highest α/β-santalene yields achieved in *P. patens* (Table S5).

Genotyping of the Cytosolic & Plastidic STS Lines.

In order to understand why the yields of α/β-santalene were low in the cytosolic STS lines, the transcripts level of the selected key genes in the terpenoid biosynthetic pathway were investigated, cf. Table G.

The transcripts profile showed an extremely low expression levels of the STS gene in WT-STS6 and WT-STS13 compared to WT-tpSTS1, of which the STS transcript level was in the same magnitude as the cytosolic PTS lines. In addition, HMGR, FPS and SQS behaved differently after the STS enzyme was introduced into the cytosol of the WT line. Thus, HMGR was overexpressed but FPS and SQS were down-regulated. However, all 3 genes were up-regulated in the plastidic line WT-tpSTS1. Regarding the genes in the MEP and its downstream pathway, different expression profiles were observed for the different regulatory genes. DXS and GGPS were up-regulated in both the cytosolic and plastidic STS lines, while the DXR level in these 3 selected lines were either reduced or improved. Moreover, the expression level of CPS/KS was reduced in both the cytosolic and plastidic STS lines. With respect to the pigments biosynthetic genes, the GGR transcript level remained constant, but the transcript level of PSY was up-regulated in WT-tpSTS1.

Genotyping of the CPS/KS KO Lines.

Compared to the STS lines in the WT background, the STS line obtained in the KO background showed an 8-fold higher STS transcript level, which appear to be too low to produce sufficient detectable amounts of α/β-santalene by GC-MS, cf. table G. The CPS/KS transcript level study confirmed the disruption of the transcriptional activity of the CPS/KS gene in KO-STS1. Likewise, the HMGR gene was up-regulated in both KO and KO-STS1, but both FPS and SQS were down-regulated. In the MEP and its downstream pathway, DXS, DXR, GGPS and PSY were all up-regulated, while GGR remained constant after the introduction of the STS gene in the KO line. When comparing between WT and KO, all regulatory genes except DXR in the MEP pathway were over-expressed after disruption of the CPS/KS gene in WT.

Abbreviations

"WT" equals "wildtype"

TABLE G

Fold change of gene expression in mutant lines compared to WT of *P. patens*

| | native MEV genes | | | native MEP genes | | | | | |
|---|---|---|---|---|---|---|---|---|---|
| | PpHMGR | FPS | SQS | DXS | DXR | GGPS | CPS/KS | GGR | PSY |
| WT | 1 | 1 | 1 | 1 | 1 | 1 | 1 | 1 | 1 |
| KO | 1.683 | 0.635 | 0.670 | 1.299 | 0.352 | 1.022 | 0.234 | 1.731 | 2.499 |
| WT-PTS10 | 1.487 | 0.449 | 0.701 | 2.086 | 1.386 | 2.131 | 5.609 | | |
| WT-PTS14 | 4.205 | 0.229 | 0.706 | 1.656 | 2.001 | 1.174 | 0.579 | | |
| WT-PTS19 | 2.741 | 1.430 | 0.988 | 0.924 | 1.027 | 0.730 | 1.082 | | |
| WT-PTS27 | 3.339 | 1.243 | 0.962 | 0.898 | 1.025 | 0.558 | 1.211 | | |
| WT-PTS35 | 3.006 | 1.595 | 1.240 | 0.512 | 1.697 | 0.330 | 0.181 | 0.702 | 0.556 |
| WT-tpPTS2 | 0.769 | 0.276 | 0.716 | 0.498 | 0.101 | 0.305 | 0.662 | 0.376 | 0.699 |

TABLE G-continued

Fold change of gene expression in mutant lines compared to WT of *P. patens*

| | native MEV genes | | native MEP genes | | | | | | |
|---|---|---|---|---|---|---|---|---|---|
| | PpHMGR | FPS | SQS | DXS | DXR | GGPS | CPS/KS | GGR | PSY |
| KO-tpPTS1 | 3.104 | 0.879 | 0.772 | 1.262 | 1.773 | 1.380 | 0.308 | 0.468 | 1.468 |
| PTS35-KO | 2.213 | 0.548 | 0.572 | 1.096 | 1.040 | 2.258 | 0.377 | 0.351 | 1.837 |
| WT-STS6 | 1.648 | 0.241 | 0.692 | 2.193 | 0.637 | 1.728 | 0.607 | | |
| WT-STS13 | 3.731 | 0.512 | 0.555 | 1.698 | 1.232 | 2.670 | 0.403 | | |
| WT-tpSTS1 | 4.529 | 2.327 | 1.076 | 2.348 | 1.794 | 1.911 | 0.532 | 0.978 | 1.553 |
| KO-STS1 | 2.070 | 0.694 | 0.715 | 2.706 | 1.139 | 2.192 | 0.331 | 1.740 | 3.891 |

Table S1 the nucleotide sequences of the primers used for vectorsconstruction

| Primer | Nucleotide sequence (5'->3') |
|---|---|
| PTS-F | GGCTTAAUATGGAGTTGTATGCCCAAAG |
| PTS-R | GGTTTAAUTTAATATGGAACAGGGTGAAG |
| STS-F | GGCTTAAUATGGATTCTTCCACCGCCAC |
| STS-R | GGTTTAAUCTACTCCTCGCCGAGAGGAA |
| tp-F | GGCTTAAUATGGCTTCCTCTATGCTCTCCTC |
| PTS-R | GGTTTAAUTTAATATGGAACAGGGTGAAGGTACAA C |
| tp-R | AGATCTUCCCCCGTTGCTTGC |
| tp-STS-F | AAGATCUAGCTGCATGAAGGAGCTCGGCGCGCCT ATGGATTCTTCCACCGCCACC |
| oCL252 | CTCTGTCTCTCCCACAATCCTCC |
| oCL77 | CCTGTGCAAGGTAAGAAGATGG |
| oSSB94 | AAGCCGACTTCAACATGTG |
| oSSB95 | AACCCGAAGCTCTTCCAC |

TABLE S2 the vectors used and constructed for PEG-mediated moss transformation

| vector | description |
|---|---|
| pCAMBIA230035Su | pCAMBIA2300 with USER cassette, hygromycin resistant |
| pCAMBIA130035Su | pCAMBIA1300 with USER cassette, kanamycin resistant |
| pUNI33 | pJET1.2 backbone with the essential compartment from pCAMBIA130035Su (plant antibiotic resistant cassette, 35S promoter-USER cloning site-35S terminator) |
| pUNI6 | pJET1.2 backbone with the essential compartment from pCAMBIA230035Su (plant antibiotic resistant cassette, 35S promoter-USER cloning site-35S terminator) |
| pUNI33 PTS | pUNI33 containing the coding region of the PTS gene |

TABLE S2-continued the vectors used and constructed for PEG-mediated moss transformation

| vector | description |
|---|---|
| pUNI33 STS | pUNI33 containing the coding region of the STS gene |
| pUNI33 tpPTS | pUNI33 containing the PTS gene with transit peptide sequence of *Arabidopsis* RuBisCO small subunit |
| pUNI33 tpSTS | pUNI33 containing the STS gene with transit peptide sequence of *Arabidopsis* RuBisCO small subunit |
| pCL755 | pDONR201::CPS/KS containing a cassette containing p35S-nptII-CamVter between two 1.5 kb homologous recombination arms from the CPS/KS gene |

Table S3 the selected regulatory genes and the nucleotide sequences of the qPCR primers

| gene | Primer | Nucleotide sequence |
|---|---|---|
| PTS | PTS-QF | AAGCACAAACCCACAACCAAGGAG |
| | PTS-QR | AGAGCTTACATGGAAGAGGCCCAA |
| STS | STS-QF | CCTTCCTGATCTTCTGCACTAC |
| | STS-QR | ATTATCGCCTCTTGCCATCTC |
| PpHMGR | P100 | CCATTCGTCCAACATTTTGATGA |
| | P101 | GGGAGCAAGCAAGTTTAACACTG |
| FPS | P134 | CAGGACGACTATCTTGACTGTTACG |
| | P135 | TTCCTTCAATAACTGTTTCTGGG |
| SQS | SQS-QF | CAGTTGCAATCTTCAGCAGTTC |
| | SQS-QR | CACCTCAACCTGCTAGTCTAATC |
| DXS | P70 | GGAGTGAGGTTGTTGTTGTTGTTG |
| | P71 | CAAGGCAGCCATAGTGAGAAAC |
| DXR | P92 | GGTCTCAGTTGCTTCCGAAATAC |
| | P93 | GAAAGAAAAGGAGAGCGTTGG |
| GGPS | P112 | GCTTCTCTCCCTTCGTCTCTCATAG |
| | P113 | CCAGCACACCACACAACTCAAC |
| CPS/KS | P136 | GCTTCCAGCACCTTGATACAGA |
| | P137 | CGACGCTTCTTTAGGCATTGA |

-continued

| Table S3 the selected regulatory genes and the nucleotide sequences of the qPCR primers | | |
|---|---|---|
| gene | Primer | Nucleotide sequence |
| GGR | P120 | AGGGTTCTTATCCGTTGATACTGC |
| | P121 | GATGTCCTGTTTTACAAGTGAATGAG |
| PSY | P124 | TCTTACAATCTGCTGGGATGGTG |
| | P125 | CCTCAAGTGCCTGGACTGGTCA |
| Actin2 | P84 | GCGAAGAGCGAGTATGACGAG |
| | P85 | CTCCATAACCCCACCTGACAA |

TABLE S4

Quantification of patchoulol and 16α-hydroxykaurane (mg/g DW) in all the PTS lines

| | Patchoulol | P value | 16α-hydroxykaurane | P value |
|---|---|---|---|---|
| WT | 0 | — | 2.42 ± 0.10 | — |
| KO | 0 | — | 0 | — |
| WT-PTS10 | 0.29 ± 0.04 | — | 3.23 ± 0.07 | — |
| WT-PTS14 | 0.20 ± 0.10 | — | 0.16 ± 0.11 | — |
| WT-PTS19 | 0.83 ± 0.08 | — | 0.61 ± 0.14 | — |
| WT-PTS27 | 0.32 ± 0.04 | — | 0.39 ± 0.13 | — |

TABLE S4-continued

Quantification of patchoulol and 16α-hydroxykaurane (mg/g DW) in all the PTS lines

| | Patchoulol | P value | 16α-hydroxykaurane | P value |
|---|---|---|---|---|
| WT-PTS35 | 0.60 ± 0.04 | — | 0.22 ± 0.03 | — |
| PTS35-KO | 0.38 ± 0.03 | 4.5123E−06 | 0 | — |
| WT-tpPTS2 | 0.02 ± 0.01 | — | 1.54 ± 0.14 | — |
| KO-tpPTS1 | n.d. (not detected) | — | 0 | — |

TABLE S5 the α/β-santalene and 16α-hydroxykaurane amounts (mg/g DW) in the STS lines

| | α-santalene | β-santalene | 16α-hydroxykaurane |
|---|---|---|---|
| WT | 0 | 0 | 2.42 ± 0.01 |
| KO | 0 | 0 | 0 |
| WT-STS3 | n.d. | n.d. | 3.21 ± 0.55 |
| WT-STS6 | n.d. | n.d. | 1.69 ± 0.37 |
| WT-STS11 | n.d. | n.d. | 0.04 ± 0.02 |
| WT-STS13 | n.d. | n.d. | 1.51 ± 0.50 |
| KO-STS1 | n.d. | n.d. | 0 |
| WT-tpSTS1 | 0.039 ± 0.008 | 0.035 ± 0.005 | 16.557 ± 5.034 |

TABLE S6 the transcripts level of the selected regulatory genes in the WT, KO and all the transgenic moss lines. They were all normalized by the actin2 gene in *P. patens*.

| | PTS | HMGR | FPS | SQS |
|---|---|---|---|---|
| WT | — | 0.107 ± 0.006 | 0.212 ± 0.033 | 0.069 ± 0.005 |
| KO | — | 0.180 ± 0.070 | 0.134 ± 0.005 | 0.047 ± 0.003 |
| WT-PTS10 | 9.159 ± 0.547 | 0.159 ± 0.014 | 0.095 ± 0.002 | 0.049 ± 0.001 |
| WT-PTS14 | 3.169 ± 1.002 | 0.449 ± 0.121 | 0.048 ± 0.019 | 0.049 ± 0.003 |
| WT-PTS19 | 11.553 ± 0.160 | 0.292 ± 0.032 | 0.303 ± 0.007 | 0.069 ± 0.005 |
| WT-PTS27 | 22.045 ± 2.633 | 0.356 ± 0.053 | 0.263 ± 0.022 | 0.067 ± 0.007 |
| WT-PTS35 | 5.731 ± 2.413 | 0.321 ± 0.027 | 0.338 ± 0.017 | 0.086 ± 0.006 |
| PTS35-KO | 2.460 ± 0.801 | 0.236 ± 0.005 | 0.116 ± 0.013 | 0.040 ± 0.001 |
| WT-tpPTS2 | 2.985 ± 0.267 | 0.082 ± 0.008 | 0.058 ± 0.014 | 0.050 ± 0.004 |
| KO-tpPTS1 | 3.192 ± 0.289 | 0.331 ± 0.037 | 0.186 ± 0.004 | 0.054 ± 0.003 |
| | **DXS** | **DXR** | **GGPS** | **CPS/KS** |
| WT | 0.067 ± 0.014 | 0.166 ± 0.008 | 0.117 ± 0.013 | 0.098 ± 0.004 |
| KO | 0.086 ± 0.018 | 0.058 ± 0.030 | 0.120 ± 0.039 | 0.023 ± 0.004 |
| WT-PTS10 | 0.139 ± 0.006 | 0.230 ± 0.005 | 0.250 ± 0.079 | 0.552 ± 0.140 |
| WT-PTS14 | 0.110 ± 0.011 | 0.332 ± 0.035 | 0.138 ± 0.025 | 0.057 ± 0.027 |
| WT-PTS19 | 0.062 ± 0.014 | 0.170 ± 0.019 | 0.086 ± 0.016 | 0.106 ± 0.012 |
| WT-PTS27 | 0.060 ± 0.011 | 0.170 ± 0.010 | 0.065 ± 0.007 | 0.119 ± 0.011 |
| WT-PTS35 | 0.034 ± 0.010 | 0.281 ± 0.030 | 0.039 ± 0.005 | 0.018 ± 0.002 |
| PTS35-KO | 0.073 ± 0.006 | 0.172 ± 0.030 | 0.265 ± 0.032 | 0.037 ± 0.010 |
| WT-tpPTS2 | 0.033 ± 0.004 | 0.017 ± 0.006 | 0.036 ± 0.027 | 0.065 ± 0.009 |
| KO-tpPTS1 | 0.084 ± 0.015 | 0.294 ± 0.024 | 0.162 ± 0.039 | 0.030 ± 0.007 |
| | **STS** | **HMGR** | **FPS** | **SQS** |
| WT-STS6 | 0.010 ± 0.003 | 0.176 ± 0.022 | 0.051 ± 0.004 | 0.048 ± 0.003 |
| WT-STS13 | 0.006 ± 0.003 | 0.398 ± 0.011 | 0.108 ± 0.035 | 0.039 ± 0.007 |
| WT-tpSTS1 | 6.670 ± 2.040 | 0.483 ± 0.210 | 0.493 ± 0.112 | 0.075 ± 0.007 |
| KO-STS1 | 0.083 ± 0.012 | 0.221 ± 0.016 | 0.147 ± 0.001 | 0.050 ± 0.004 |
| | **DXS** | **DXR** | **GGPS** | **CPS/KS** |
| WT-STS6 | 0.146 ± 0.022 | 0.106 ± 0.016 | 0.202 ± 0.016 | 0.060 ± 0.012 |
| WT-STS13 | 0.113 ± 0.009 | 0.204 ± 0.086 | 0.313 ± 0.025 | 0.040 ± 0.008 |
| WT-tpSTS1 | 0.156 ± 0.029 | 0.297 ± 0.114 | 0.224 ± 0.016 | 0.052 ± 0.011 |
| KO-STS1 | 0.180 ± 0.039 | 0.189 ± 0.023 | 0.257 ± 0.052 | 0.033 ± 0.011 |

TABLE S6-continued the transcripts level of the selected regulatory genes in the WT, KO and all the transgenic moss lines. They were all normalized by the actin2 gene in *P. patens*.

| | GGR | PSY |
|---|---|---|
| WT | 0.908 ± 0.047 | 0.133 ± 0.011 |
| KO | 1.572 ± 0.031 | 0.333 ± 0.010 |
| WT-PTS35 | 0.638 ± 0.306 | 0.074 ± 0.017 |
| PTS35-KO | 0.319 ± 0.043 | 0.244 ± 0.021 |
| WT-tpPTS2 | 0.341 ± 0.047 | 0.093 ± 0.009 |
| KO-tpPTS1 | 0.425 ± 0.031 | 0.195 ± 0.029 |
| WT-tpSTS1 | 0.888 ± 0.219 | 0.207 ± 0.023 |
| KO-STS1 | 1.580 ± 0.109 | 0.518 ± 0.079 |

TABLE S7

Production of levels of Patchoulol, santalene and 16-hydroxykaurene

| | 16-hydroxy-kaurane | stdev |
|---|---|---|
| WT | 2.4209 | 0.0997 |
| WT-STS3 | 3.2115 | 0.5484 |
| WT-STS6 | 1.6868 | 0.3742 |
| WT-STS11 | 0.0449 | 0.0167 |
| WT-STS13 | 1.5142 | 0.4877 |
| KO-STS1 | nd | nd |
| WT-tpSTS1 | 16.5572 | 5.0341 |

nd: not detected.
The leves are given in mg/g dry weight.

REFERENCES

1. Kirby J, Keasling J D: Biosynthesis of plant isoprenoids: Perspectives for microbial engineering. *Annu Rev Plant Biol* 2009, 60:335-355.

2. Pickel B, Drew D P, Manczak T, Weitzel C, Simonsen H T, Ro D K: Identification and characterization of a kunzeaol synthase from *Thapsia garganica: implications for the biosynthesis of the pharmaceutical thapsigargin. Biochemical Journal* 2012, 448(2):261-271.

3. Martin D M, Fäldt J, Bohlmann J: Functional characterization of nine Norway spruce TPS genes and evolution of gymnosperm terpene synthases of the TPS-d subfamily. *Plant Physiol* 2004, 135(4): 1908-1927.

4. Hamberger B, Ohnishi T, Hamberger B, Séguin A, Bohlmann J: Evolution of diterpene metabolism: Sitka spruce CYP720B4 catalyzes multiple oxidations in resin acid biosynthesis of conifer defense against insects. *Plant Physiol* 2011, 157(4):1677-1695.

5. Fischer M J, Meyer S, Claudel P, Perrin M, Ginglinger J F, Gertz C, Masson J E, Werck-Reinhardt D, Hugueney P, Karst F: Specificity of *Ocimum basilicum* geraniol synthase modified by its expression in different heterologous systems. *J Biotechnol* 2012, 163(1):24-29.

6. Rensing S A, Fritzowsky D, Lang D, Reski R: Protein encoding genes in an ancient plant: analysis of codon usage, retained genes and splice sites in a moss, *Physcomitrella patens. Bmc Genomics* 2005, 6:43.

7. Viëtor R, Loutelier-Bourhis C, Fitchette A C, Margerie P, Gonneau M, Faye L, Lerouge P: Protein N-glycosylation is similar in the moss *Physcomitrella patens* and in higher plants. *Planta* 2003, 218(2):269-275.

8. Koprivova A, Altmann F, Gorr G, Kopriva S, Reski R, Decker E L: N-glycosylation in the moss *Physcomitrella patens* is organized similarly to that in higher plants. *Plant Biol* 2003, 5(6):582-591.

9. Mega T: Plant-type N-glycans containing fucose and xylose in Bryophyta (mosses) and Tracheophyta (ferns). *Biosci Biotechnol Biochem* 2007, 71(12):2893-2904.

10. Simonsen H T, Drew D P, Lunde C: Perspectives on using *Physcomitrella patens* as an alternative production platform for thapsigargin and other terpenoid drug candidates. *Perspect Medicin Chem* 2009, 3:1-6.

11. Anterola A, Shanle E, Perroud P F, Quatrano R: Production of taxa-4(5), 11(12)-diene by transgenic *Physcomitrella patens. Transgeic Res* 2009, 18(4):655-660.

12. Hamberger B, Bak S: Plant P450s as versatile drivers for evolution of species specific chemical diversity In: *Phil Trans R Soc B* (*in press*). 2013.

13. Yonekura-Sakakibara K, Hanada K: An evolutionary view of functional diversity in family 1 glycosyltransferases. *Plant J* 2011, 66(1):182-193.

14. Chen F, Tholl D, Bohlmann J, Pichersky E: The family of terpene synthases in plants: a mid-size family of genes for specialized metabolism that is highly diversified throughout the kingdom. *Plant J* 2011, 66(1):212-229.

15. Sakamoto T, Miura K, Itoh H, Tatsumi T, Ueguchi-Tanaka M, Ishiyama K, Kobayashi M, Agrawal G K, Takeda S, Abe K et al: An overview of gibberellin metabolism enzyme genes and their related mutants in rice. *Plant Physiol* 2004, 134(4):1642-1653.

16. Anterola A, Shanle E: Genomic insights in moss gibberellin biosynthesis. *Bryologist* 2008, 111(2):218-230.

17. Johri M M: Hormonal regulation in green plant lineage families. *Physiol Mol Biol Plants* 2008, 14(1-2):23-38.

18. von Schwartzenberg K, Schultze W, Kassner H: The moss *Physcomitrella patens* releases a tetracyclic diterpene. *Plant Cell Rep* 2004, 22(10):780-786.

19. Schaefer D G, Zrÿd J P: Efficient gene targeting in the moss *Physcomitrella patens. Plant J* 1997, 11(6): 1195-1206.

20. Hayashi K, et al: Endogenous diterpenes derived from ent-daurene, a common gibberellin precursor, regulate protonema differentiation of the moss *Physcomitrella patens. Plant Physiol* 2010, 153(3): 1085-1097.

21. Bach S S, King B C, Zhan X, Simonsen H T, Hamberger B: Heterologous stable expression of terpenoid biosynthetic genes using the moss *Physcomitrella patens*. In: Methods in Molecular Biology Edited by Rodriguez-Concepcion M, vol. The Plant Isoprenoids; 2013: in press.

22. Reski R: Molecular genetics of *Physcomitrella. Planta* 1999, 208:301-309.

23. Reski R: Development, genetics and molecular biology of mosses. *Botanica Acta* 1998, 111:1-15.

24. Ashton N W, Grimsley N H, Cove D J: Analysis of Gametophytic Development in the Moss, *Physcomitrella-Patens*, Using Auxin and Cytokinin Resistant Mutants. *Planta* 1979, 144(5):427-435.

What is claimed is:

1. A transgenic moss plant or moss cell capable of producing farnesyl-pyrophosphate (FPP) or geranylgeranyl-pyrophosphate (GGPP), wherein the transgenic moss plant or moss cell comprises a heterologous nucleic acid molecule encoding a polypeptide having a patchoulol synthase activity to catalyze the conversion of FPP to patchoulol, wherein the polypeptide having a patchoulol synthase activity comprises an amino acid sequence having at least 94% sequence identity to SEQ ID NO: 17, wherein the transgenic moss plant or moss cell is *Physcomitrella patens*, and wherein the transgenic moss plant or moss cell emits volatile patchoulol.

2. The transgenic moss plant or moss cell of claim 1, wherein the polypeptide comprises an amino acid sequence at least 96%, 97%, 98%, or 99% identical to SEQ ID NO: 17.

3. The transgenic moss plant or moss cell of claim 1, wherein the heterologous nucleic acid molecule comprises the nucleotide sequence of SEQ ID NO: 1.

4. A method for producing a transgenic moss plant or moss cell that emits volatile patchoulol comprising introducing into a moss cell capable of producing farnesyl-pyrophosphate (FPP) or geranylgeranyl-pyrophosphate (GGPP) a heterologous nucleic acid molecule encoding a polypeptide having a patchoulol synthase activity to catalyze the conversion of FPP to patchoulol, and optionally regenerating a transgenic moss plant from the moss cell; wherein the polypeptide having a patchoulol synthase activity comprises an amino acid sequence having at least 94% sequence identity to SEQ ID NO: 17, wherein the transgenic moss plant or moss cell is *Physcomitrella patens*.

5. The method of claim 4, wherein the polypeptide comprises an amino acid sequence at least 96%, 97%, 98%, or 99% identical to SEQ ID NO: 17.

6. The method of claim 4, wherein the heterologous nucleic acid molecule comprises the nucleotide sequence of SEQ ID NO: 1.

7. A method for preparing patchoulol in a transgenic moss plant or moss cell comprising;

culturing or cultivating the transgenic moss plant or moss cell of claim 1 to express the polypeptide having a patchoulol synthase activity encoded by the heterologous nucleic acid molecule.

8. The method of claim 7, wherein the polypeptide comprises an amino acid sequence at least 96%, 97%, 98%, or 99% identical to SEQ ID NO: 17.

* * * * *

SEQUENCE LISTING

<160> NUMBER OF SEQ ID NOS: 17

<210> SEQ ID NO 1
<211> LENGTH: 1659
<212> TYPE: DNA
<213> ORGANISM: Pogostemon cablin

<400> SEQUENCE: 1

```
atggagttgt atgcccaaag tgttggagtg ggtgctgctt ctcgtcctct tgcgaatttt     60

catccatgtg tgtggggaga caaattcatt gtctacaacc cacaatcatg ccaggctgga    120

gagagagaag aggctgagga gctgaaagtg gagctgaaaa gagagctgaa ggaagcatca    180

gacaactaca tgcggcaact gaaaatggtg gatgcaatac aacgattagg cattgactat    240

ctttttgtgg aagatgttga tgaagctttg aagaatctgt ttgaaatgtt tgatgctttc    300

tgcaagaata atcatgacat gcacgccact gctctcagct ttcgccttct cagacaacat    360

ggatacagag tttcatgtga agtttttgaa aagtttaagg atggcaaaga tggatttaag    420

gttccaaatg aggatggagc ggttgcagtc cttgaattct tcgaagccac gcatctcaga    480

gtccatggag aagacgtcct tgataatgct tttgacttca ctaggaacta cttggaatca    540

gtctatgcaa ctttgaacga tccaaccgcg aaacaagtcc acaacgcatt gaatgagttc    600

tcttttcgaa gaggattgcc acgcgtggaa gcaaggaagt acatatcaat ctacgagcaa    660

tacgcatctc atcacaaagg cttgctcaaa cttgctaagc tggatttcaa cttggtacaa    720

gctttgcaca gaagggagct gagtgaagat tctaggtggt ggaagacttt acaagtgccc    780

acaaagctat cattcgttag agatcgattg gtggagtcct acttctgggc ttcgggatct    840

tatttcgaac cgaattattc ggtagctagg atgattttag caaaagggct ggctgtatta    900

tctcttatgg atgatgtgta tgatgcatat ggtacttttg aggaattaca aatgttcaca    960

gatgcaatcg aaaggtggga tgcttcatgt ttagataaac ttccagatta catgaaaata   1020

gtatacaagg ccctttgga tgtgtttgag gaagttgacg aggagttgat caagctaggc   1080

gcaccatatc gagcctacta tggaaaagaa gccatgaaat acgccgcgag agcttacatg   1140

gaagaggccc aatggaggga gcaaaagcac aaacccacaa ccaaggagta tatgaagctg   1200

gcaaccaaga catgtggcta cataactcta ataatattat catgtcttgg agtggaagag   1260

ggcattgtga ccaaagaagc cttcgattgg gtgttctccc gacctccttt catcgaggct   1320

acattaatca ttgccaggct cgtcaatgat attacaggac acgagtttga gaaaaaacga   1380

gagcacgttc gcactgcagt agaatgctac atggaagagc acaaagtggg gaagcaagag   1440

gtggtgtctg aattctacaa ccaaatggag tcagcatgga aggacattaa tgaggggttc   1500

ctcagaccag ttgaatttcc aatccctcta ctttatctta ttctcaattc agtccgaaca   1560

cttgaggtta tttacaaaga gggcgattcg tatacacacg tgggtcctgc aatgcaaaac   1620

atcatcaagc agttgtacct tcaccctgtt ccatattaa                          1659
```

<210> SEQ ID NO 2
<211> LENGTH: 1710
<212> TYPE: DNA
<213> ORGANISM: Santalum sp.

<400> SEQUENCE: 2

```
atggattctt ccaccgccac cgccatgaca gctccattca ttgatcctac tgatcatgtg     60

aatctcaaaa ctgatactga tgcctcagag aatcgaagga tgggaaatta taaacccagc    120

atttggaatt atgatttttt acaatcactt gcaactcatc acaatattgt ggaagagagg    180
```

```
catctaaagc ttgctgagaa gctgaagggc caagtgaagt ttatgtttgg ggcaccaatg    240

gagccgttag caaagctgga gcttgtggat gtggttcaaa ggcttgggct aaaccaccta    300

tttgagacag agatcaagga agcgctgttt agtatttaca aggatgggag caatggatgg    360

tggtttggcc accttcatgc gacatctctc cgatttaggc tgctacgaca gtgtgggctt    420

tttattcccc aagatgtgtt taaaacgttc caaaacaaaa ctggggaatt tgatatgaaa    480

ctgtgggaca acgtaaaagg gctgctgagc ttatatgaag cttcatactt gggatggaag    540

ggtgaaaaca tcctagatga agccaaggcc ttcaccacca agtgcttgaa aagtgcatgg    600

gaaaatatat ccgaaaagtg gttagccaaa agagtgaagc atgctttggc tttgcctttg    660

cattggagag tccctcgaat cgaagctaga tggttcattg aggtatatga gcaagaagcg    720

aatatgaacc caacactact caaactcgca aaattagact ttaatatggt gcaatcaatt    780

catcagaaag agattgggga attagcaagg tggtgggtga ctactggctt ggataagtta    840

gactttgcta ggaataattt actgcagagc tatatgtgga gctgcgcgat tgcttccgac    900

ccgaagttca aacttgctag agaaactatt gtcgaaatcg gaagtgtact cacagttgtt    960

gacgatggat atgacgtcta tggttcaatg gacgaacttg atctctacac aagctccgtt   1020

gaaaggtgga gctgtgtgaa aattgacaag ttgccaaaca cgttaaaatt aatttttatg   1080

tctatgttca acaagaccaa tgaggttggt cttcgagtcc agcatgagcg aggctacaat   1140

agcatcccta cttttatcaa agcgtgggtt gaacagtgta aatcatacca gaaagaagca   1200

agatggttcc acgggggaca cacgcctcca ttggaagaat atagcttgaa tggacttgtt   1260

tccataggat tccctctctt gttaatcaca ggctacgtgg caatcgctga gaacgaggct   1320

gcactggata aagtgcaccc ccttcctgat cttctgcact actcctccct ccttagtcgc   1380

ctcatcaatg atataggaac gtctccggat gagatggcaa gaggcgataa tctgaagtca   1440

atccattgtt acatgaacga aactggggct tccgaggaag ttgctcgtga gcacataaag   1500

ggagtaatcg aggagaattg gaaaatactg aatcagtgct gctttgatca atctcagttt   1560

caggagcctt ttataacctt caatttgaac tctgttcgag ggtctcattt cttctatgaa   1620

tttggggatg gctttggggt gacggatagc tggacaaagg ttgatatgaa gtccgttttg   1680

atcgacccta ttcctctcgg cgaggagtag                                    1710
```

<210> SEQ ID NO 3
<211> LENGTH: 4143
<212> TYPE: DNA
<213> ORGANISM: Salvia sclarea

<400> SEQUENCE: 3

```
atgacttctg taaatttgag cagagcacca gcagcgatta cccggcgcag gctgcagcta     60

cagccggaat ttcatgccga gtgttcatgg ctgaaaagca gcagcaaaca cgcgcccttg    120

accttgagtt gccaaatccg tcctaagcaa ctctcccaaa tagctgaatt gagagtaaca    180

agcctggatg cgtcgcaagc gagtgaaaaa gacatttccc ttgttcaaac tccgcataag    240

gttgaggtta atgaaaagat cgaggagtca atcgagtacg tccaaaatct gttgatgacg    300

tcgggcgacg ggcgaataag cgtgtcaccc tatgacacgg cagtgatcgc cctgatcaag    360

gacttgaaag ggcgcgacgc cccgcagttt ccgtcatgtc tcgagtggat cgcgcaccac    420

caactggctg atggctcatg gggcgacgaa ttcttctgta tttatgatcg gattctaaat    480

acattggcat gtgtcgtagc cttgaaatca tggaaccttc actctgatat tattgaaaaa    540
```

-continued

```
ggagtgacgt acatcaagga gaatgtgcat aaacttaaag gtgcaaatgt tgagcacagg    600
acagcggggt tcgaacttgt ggttcctact tttatgcaaa tggccacaga tttgggcatc    660
caagatctgc cctatgatca tcccctcatc aaggagattg ctgacacaaa acaacaaaga    720
ttgaaagaga tacccaagga tttggtttac caaatgccaa cgaatttact gtacagttta    780
gaagggttag gagatttgga gtgggaaagg ctactgaaac tgcagtcggg caatggctcc    840
ttcctcactt cgccgtcgtc caccgccgcc gtcttgatgc ataccaaaga tgaaaaatgt    900
ttgaaataca tcgaaaacgc cctcaagaat tgcgacggag gagcaccaca tacttatcca    960
gtcgatatct tctcaagact ttgggcaatc gataggctac aacgcctagg aatttctcgt   1020
ttcttccagc acgagatcaa gtatttctta gatcacatcg aaagcgtttg ggaggagacc   1080
ggagttttca gtggaagata tacgaaattt agcgatattg atgacacgtc catgggcgtt   1140
aggcttctca aaatgcacgg atacgacgtc gatccaaatg tactaaaaca tttcaagcaa   1200
caagatggta aattttcctg ctacattggt caatcggtcg agtctgcatc tccaatgtac   1260
aatctttata gggctgctca actaagattt ccaggagaag aagttcttga agaagccact   1320
aaatttgcct ttaacttctt gcaagaaatg ctagtcaaag atcgacttca agaaagatgg   1380
gtgatatccg accacttatt tgatgagata aagctggggt tgaagatgcc atggtacgcc   1440
actctacccc gagtcgaggc tgcatattat ctagaccatt atgctggttc tggtgatgta   1500
tggattggca agagtttcta caggatgcca gaaatcagca atgatacata caaggagctt   1560
gcgatattgg atttcaacag atgccaaaca caacatcagt tggagtggat ccacatgcag   1620
gaatggtacg acagatgcag ccttagcgaa ttcgggataa gcaaaagaga gttgcttcgc   1680
tcttactttc tggccgcagc aaccatattc gaaccggaga gaactcaaga gaggcttctg   1740
tgggccaaaa ccagaattct ttctaagatg atcacttcat ttgtcaacat tagtggaaca   1800
acactatctt tggactacaa tttcaatggc ctcgatgaaa taattagtag tgccaatgaa   1860
gatcaaggac tggctgggac tctgctggca accttccatc aacttctaga cggattcgat   1920
atatacactc tccatcaact caaacatgtt tggagccaat ggttcatgaa agtgcagcaa   1980
ggagagggaa gcggcgggga agacgcggtg ctcctagcga acacgctcaa catctgcgcc   2040
ggcctcaacg aagacgtgtt gtccaacaat gaatacacgg ctctgtccac cctcacaaat   2100
aaaatctgca atcgcctcgc ccaaattcaa gacaataaga ttctccaagt tgtggatggg   2160
agcataaagg ataaggagct agaacaggat atgcaggcgt tggtgaagtt agtgcttcaa   2220
gaaaatggcg gcgccgtaga cagaaacatc agacacacgt tttgtcggt ttccaagact    2280
ttctactacg atgcctacca cgacgatgag acgaccgatc ttcatatctt caaagtactc   2340
tttcgaccgg ttgtacaaac tttgaatttt gatttgctta agttggcagg agatgtggaa   2400
tctaacccag gacctatgtc gctcgccttc aacgtcggag ttacgccttt ctccggccaa   2460
agagttggga gcaggaaaga aaaatttcca gtccaaggat ttcctgtgac cacccccaat   2520
aggtcacgtc tcatcgttaa ctgcagcctt actacaatag atttcatggc gaaaatgaaa   2580
gagaatttca agagggaaga cgataaattt ccaacgacaa cgactcttcg atccgaagat   2640
ataccctcta atttgtgtat aatcgacacc cttcaaaggt tgggggtcga tcaattcttc   2700
caatatgaaa tcaacactat tctagataac acattcaggt tgtggcaaga aaaacacaaa   2760
gttatatatg gcaatgttac tactcatgca atggcattta ggcttttgcg agtgaaagga   2820
tacgaagttt catcagagga gttggctcca tatggtaacc aagaggctgt tagccagcaa   2880
acaaatgacc tgccgatgat tattgagctt tatagagcag caaatgagag aatatatgaa   2940
```

```
gaagagagga gtcttgaaaa aattcttgct tggactacca tctttctcaa taagcaagtg   3000

caagataact caattcccga caaaaaactg cacaaactgg tggaattcta cttgaggaat   3060

tacaaaggca taaccataag attgggagct agacgaaacc tcgagctata tgacatgacc   3120

tactatcaag ctctgaaatc tacaaacagg ttctctaatt tatgcaacga agattttcta   3180

gttttcgcaa agcaagattt cgatatacat gaagcccaga accagaaagg acttcaacaa   3240

ctgcaaaggt ggtatgcaga ttgtaggttg gacaccttaa actttggaag agatgtagtt   3300

attattgcta attatttggc ttcattaatt attggtgatc atgcgtttga ctatgttcgt   3360

ctcgcatttg ccaaaacatc tgtgcttgta acaattatgg atgatttttt cgactgtcat   3420

ggctctagtc aagagtgtga caagatcatt gaattagtaa aagaatggaa ggagaatccg   3480

gatgcagagt acggatctga ggagcttgag atccttttta tggcgttgta caatacagta   3540

aatgagttgg cggagagggc tcgtgttgaa caggggcgta gtgtcaaaga gtttctagtc   3600

aaactgtggg ttgaaatact ctcagctttc aagatagaat tagatacatg gagcaatggc   3660

acgcagcaaa gcttcgatga atacatttct tcgtcgtggt tgtcgaacgg ttcccggctg   3720

acaggtctcc tgacgatgca attcgtcgga gtaaaattgt ccgatgaaat gcttatgagt   3780

gaagagtgca ctgatttggc taggcatgtc tgtatggtcg gccggctgct caacgacgtg   3840

tgcagttctg agagggagcg cgaggaaaat attgcaggaa aaagttatag cattctacta   3900

gcaactgaga aagatggaag aaaagttagt gaagatgaag ccattgcaga gatcaatgaa   3960

atggttgaat atcactggag aaaagtgttg cagattgtgt ataaaaaaga aagcattttg   4020

ccaagaagat gcaaagatgt atttttggag atggctaagg gtacgtttta tgcttatggg   4080

atcaacgatg aattgacttc tcctcagcaa tccaaggaag atatgaaatc ctttgtcttt   4140

tga                                                                 4143
```

<210> SEQ ID NO 4

<400> SEQUENCE: 4

000

<210> SEQ ID NO 5

<400> SEQUENCE: 5

000

<210> SEQ ID NO 6
<211> LENGTH: 2974
<212> TYPE: DNA
<213> ORGANISM: Artificial Sequence
<220> FEATURE:
<223> OTHER INFORMATION: synthetic pJET1.2
<220> FEATURE:
<221> NAME/KEY: misc_feature
<222> LOCATION: (1)..(2974)

<400> SEQUENCE: 6

```
gcccctgcag ccgaattata ttatttttgc caaataattt ttaacaaaag ctctgaagtc     60

ttcttcattt aaattcttag atgatacttc atctggaaaa ttgtcccaat tagtagcatc    120

acgctgtgag taagttctaa accatttttt tattgttgta ttatctctaa tcttactact    180

cgatgagttt tcggtattat ctctattttt aacttggagc aggttccatt cattgttttt    240

ttcatcatag tgaataaaat caactgcttt aacacttgtg cctgaacacc atatccatcc    300
```

```
ggcgtaatac gactcactat agggagagcg gccgccagat cttccggatg gctcgagttt    360
ttcagcaaga tatctttcta gaagatctcc tacaatattc tcagctgcca tggaaaatcg    420
atgttcttct tttattctct caagattttc aggctgtata ttaaaactta tattaagaac    480
tatgctaacc acctcatcag gaaccgttgt aggtggcgtg ggttttcttg gcaatcgact    540
ctcatgaaaa ctacgagcta aatattcaat atgttcctct tgaccaactt tattctgcat    600
tttttttgaa cgaggtttag agcaagcttc aggaaactga gacaggaatt ttattaaaaa    660
tttaaatttt gaagaaagtt cagggttaat agcatccatt ttttgctttg caagttcctc    720
agcattctta acaaaagacg tctcttttga catgtttaaa gtttaaacct cctgtgtgaa    780
attgttatcc gctcacaatt ccacacatta tacgagccgg aagcataaag tgtaaagcct    840
ggggtgccta atgagtgagc taactcacat taattgcgtt gcgctcactg ccaattgctt    900
tccagtcggg aaacctgtcg tgccagctgc attaatgaat cggccaacgc gcggggagag    960
gcggtttgcg tattgggcgc tcttccgctt cctcgctcac tgactcgctg cgctcggtcg   1020
ttcggctgcg gcgagcggta tcagctcact caaaggcggt aatacggtta tccacagaat   1080
caggggataa cgcaggaaag aacatgtgag caaaaggcca gcaaaaggcc aggaaccgta   1140
aaaaggccgc gttgctggcg tttttccata ggctccgccc ccctgacgag catcacaaaa   1200
atcgacgctc aagtcagagg tggcgaaacc cgacaggact ataaagatac caggcgtttc   1260
cccctggaag ctccctcgtg cgctctcctg ttccgaccct gccgcttacc ggatacctgt   1320
ccgcctttct cccttcggga agcgtggcgc tttctcatag ctcacgctgt aggtatctca   1380
gttcggtgta ggtcgttcgc tccaagctgg gctgtgtgca cgaacccccc gttcagcccg   1440
accgctgcgc cttatccggt aactatcgtc ttgagtccaa cccggtaaga cacgacttat   1500
cgccactggc agcagccact ggtaacagga ttagcagagc gaggtatgta ggcggtgcta   1560
cagagttctt gaagtggtgg cctaactacg gctacactag aaggacagta tttggtatct   1620
gcgctctgct gaagccagtt accttcggaa aaagagttgg tagctcttga tccggcaaac   1680
aaaccaccgc tggtagcggt ggtttttttg tttgcaagca gcagattacg cgcagaaaaa   1740
aaggatctca agaagatcct ttgatctttt ctacggggtc tgacgctcag tggaacgaaa   1800
actcacgtta agggattttg gtcatgagat tatcaaaaag gatcttcacc tagatccttt   1860
taaattaaaa atgaagtttt aaatcaatct aaagtatata tgagtaaact tggtctgaca   1920
gttaccaatg cttaatcagt gaggcaccta tctcagcgat ctgtctattt cgttcatcca   1980
tagttgcctg actccccgtc gtgtagataa ctacgatacg ggagggctta ccatctggcc   2040
ccagtgctgc aatgataccg cgagacccac gctcaccggc tccagattta tcagcaataa   2100
accagccagc cggaagggcc gagcgcagaa gtggtcctgc aactttatcc gcctccatcc   2160
agtctattaa ttgttgccgg gaagctagag taagtagttc gccagttaat agtttgcgca   2220
acgttgttgc cattgctaca ggcatcgtgg tgtcacgctc gtcgtttggt atggcttcat   2280
tcagctccgg ttcccaacga tcaaggcgag ttacatgatc ccccatgttg tgcaaaaaag   2340
cggttagctc cttcggtcct ccgatcgttg tcagaagtaa gttggccgca gtgttatcac   2400
tcatggttat ggcagcactg cataattctc ttactgtcat gccatccgta agatgctttt   2460
ctgtgactgg tgagtactca accaagtcat tctgagaata gtgtatgcgg cgaccgagtt   2520
gctcttgccc ggcgtcaata cgggataata ccgcgccaca tagcagaact ttaaaagtgc   2580
tcatcattgg aaaacgttct tcggggcgaa aactctcaag gatcttaccg ctgttgagat   2640
```

```
ccagttcgat gtaacccact cgtgcaccca actgatcttc agcatctttt actttcacca   2700

gcgtttctgg gtgagcaaaa acaggaaggc aaaatgccgc aaaaaaggga ataagggcga   2760

cacggaaatg ttgaatactc atactcttcc tttttcaata ttattgaagc atttatcagg   2820

gttattgtct catgagcgga tacatatttg aatgtattta gaaaaataaa caaatagggg   2880

ttccgcgcac atttccccga aaagtgccac ctgacgtcta agaaaccatt attatcatga   2940

cattaaccta taaaaatagg cgtatcacga ggcc                               2974
```

<210> SEQ ID NO 7
<211> LENGTH: 10003
<212> TYPE: DNA
<213> ORGANISM: Artificial Sequence
<220> FEATURE:
<223> OTHER INFORMATION: synthetic pLIFE33
<220> FEATURE:
<221> NAME/KEY: misc_feature
<222> LOCATION: (1)..(10003)

<400> SEQUENCE: 7

```
cgtaatcatg gtcatagctg tttcctgtgt gaaattgtta tccgctcaca attccacaca     60

acatacgagc cggaagcata aagtgtaaag cctggggtgc ctaatgagtg agctaactca    120

cattaattgc gttgcgctca ctgcccgctt tccagtcggg aaacctgtcg tgccagctgc    180

attaatgaat cggccaacgc gcggggagag gcggtttgcg tattggctag agcagcttgc    240

caacatggtg gagcacgaca ctctcgtcta ctccaagaat atcaaagata cagtctcaga    300

agaccaaagg gctattgaga cttttcaaca aagggtaata tcgggaaacc tcctcggatt    360

ccattgccca gctatctgtc acttcatcaa aaggacagta gaaaaggaag gtggcaccta    420

caaatgccat cattgcgata aaggaaaggc tatcgttcaa gatgcctctg ccgacagtgg    480

tcccaaagat ggacccccac ccacgaggag catcgtggaa aaagaagacg ttccaaccac    540

gtcttcaaag caagtggatt gatgtgataa catggtggag cacgacactc tcgtctactc    600

caagaatatc aaagatacag tctcagaaga ccaaagggct attgagactt ttcaacaaag    660

ggtaatatcg ggaaacctcc tcggattcca ttgcccagct atctgtcact tcatcaaaag    720

gacagtagaa aaggaaggtg gcacctacaa atgccatcat tgcgataaag gaaaggctat    780

cgttcaagat gcctctgccg acagtggtcc caaagatgga cccccaccca cgaggagcat    840

cgtggaaaaa gaagacgttc caaccacgtc ttcaaagcaa gtggattgat gtgatatctc    900

cactgacgta agggatgacg cacaatccca ctatccttcg caagaccttc ctctatataa    960

ggaagttcat ttcatttgga gaggacacgc tgaaatcacc agtctctctc tacaaatcta   1020

tctctctcga gctttcgcag atcccggggg gcaatgagat atgaaaaagc ctgaactcac   1080

cgcgacgtct gtcgagaagt ttctgatcga aaagttcgac agcgtctccg acctgatgca   1140

gctctcggag ggcgaagaat ctcgtgcttt cagcttcgat gtaggagggc gtggatatgt   1200

cctgcgggta aatagctgcg ccgatggttt ctacaaagat cgttatgttt atcggcactt   1260

tgcatcggcc gcgctcccga ttccggaagt gcttgacatt ggggagttta gcgagagcct   1320

gacctattgc atctcccgcc gtgcacaggg tgtcacgttg caagacctgc ctgaaaccga   1380

actgcccgct gttctacaac cggtcgcgga ggctatggat gcgatcgctg cggccgatct   1440

tagccagacg agcgggttcg gcccattcgg accgcaagga atcggtcaat acactacatg   1500

gcgtgatttc atatgcgcga ttgctgatcc ccatgtgtat cactggcaaa ctgtgatgga   1560

cgacaccgtc agtgcgtccg tcgcgcaggc tctcgatgag ctgatgcttt gggccgagga   1620
```

-continued

```
ctgccccgaa gtccggcacc tcgtgcacgc ggatttcggc tccaacaatg tcctgacgga   1680
caatggccgc ataacagcgg tcattgactg gagcgaggcg atgttcgggg attcccaata   1740
cgaggtcgcc aacatcttct tctggaggcc gtggttggct tgtatggagc agcagacgcg   1800
ctacttcgag cggaggcatc cggagcttgc aggatcgcca cgactccggg cgtatatgct   1860
ccgcattggt cttgaccaac tctatcagag cttggttgac ggcaatttcg atgatgcagc   1920
ttgggcgcag ggtcgatgcg acgcaatcgt ccgatccgga gccgggactg tcgggcgtac   1980
acaaatcgcc cgcagaagcg cggccgtctg gaccgatggc tgtgtagaag tactcgccga   2040
tagtggaaac cgacgcccca gcactcgtcc gagggcaaag aaatagagta gatgccgacc   2100
ggatctgtcg atcgacaagc tcgagtttct ccataataat gtgtgagtag ttcccagata   2160
agggaattag ggttcctata gggtttcgct catgtgttga gcatataaga aacccttagt   2220
atgtatttgt atttgtaaaa tacttctatc aataaaattt ctaattccta aaaccaaaat   2280
ccagtactaa aatccagatc ccccgaatta attcggcgtt aattcagtac attaaaaacg   2340
tccgcaatgt gttattaagt tgtctaagcg tcaatttgtt tacaccacaa tatatcctgc   2400
caccagccag ccaacagctc cccgaccggc agctcggcac aaaatcacca ctcgatacag   2460
gcagcccatc agtccgggac ggcgtcagcg ggagagccgt tgtaaggcgg cagactttgc   2520
tcatgttacc gatgctattc ggaagaacgg caactaagct gccgggtttg aaacacggat   2580
gatctcgcgg agggtagcat gttgattgta acgatgacag agcgttgctg cctgtgatca   2640
ccgcggtttc aaaatcggct ccgtcgatac tatgttatac gccaactttg aaaacaactt   2700
tgaaaaagct gttttctggt atttaaggtt ttagaatgca aggaacagtg aattggagtt   2760
cgtcttgtta taattagctt cttggggtat ctttaaatac tgtagaaaag aggaaggaaa   2820
taataaatgg ctaaaatgag aatatcaccg gaattgaaaa aactgatcga aaaataccgc   2880
tgcgtaaaag atacggaagg aatgtctcct gctaaggtat ataagctggt gggagaaaat   2940
gaaaacctat atttaaaaat gacggacagc cggtataaag ggaccaccta tgatgtggaa   3000
cgggaaaagg acatgatgct atggctggaa ggaaagctgc ctgttccaaa ggtcctgcac   3060
tttgaacggc atgatggctg gagcaatctg ctcatgagtg aggccgatgg cgtcctttgc   3120
tcggaagagt atgaagatga acaaagccct gaaaagatta tcgagctgta tgcggagtgc   3180
atcaggctct ttcactccat cgacatatcg gattgtccct atacgaatag cttagacagc   3240
cgcttagccg aattggatta cttactgaat aacgatctgg ccgatgtgga ttgcgaaaac   3300
tgggaagaag acactccatt taaagatccg cgcgagctgt atgatttttt aaagacggaa   3360
aagcccgaag aggaacttgt cttttcccac ggcgacctgg gagacagcaa catctttgtg   3420
aaagatggca aagtaagtgg ctttattgat cttgggagaa gcggcagggc ggacaagtgg   3480
tatgacattg ccttctgcgt ccggtcgatc agggaggata tcggggaaga acagtatgtc   3540
gagctatttt ttgacttact ggggatcaag cctgattggg agaaaataaa atattatatt   3600
ttactggatg aattgtttta gtacctagaa tgcatgacca aaatccctta acgtgagttt   3660
tcgttccact gagcgtcaga ccccgtagaa aagatcaaag gatcttcttg agatcctttt   3720
tttctgcgcg taatctgctg cttgcaaaca aaaaaaccac cgctaccagc ggtggtttgt   3780
ttgccggatc aagagctacc aactcttttt ccgaaggtaa ctggcttcag cagagcgcag   3840
ataccaaata ctgtccttct agtgtagccg tagttaggcc accacttcaa gaactctgta   3900
gcaccgccta catacctcgc tctgctaatc ctgttaccag tggctgctgc cagtggcgat   3960
aagtcgtgtc ttaccgggtt ggactcaaga cgatagttac cggataaggc gcagcggtcg   4020
```

```
ggctgaacgg ggggttcgtg cacacagccc agcttggagc gaacgaccta caccgaactg   4080

agatacctac agcgtgagct atgagaaagc gccacgcttc ccgaagggag aaaggcggac   4140

aggtatccgg taagcggcag ggtcggaaca ggagagcgca cgagggagct tccaggggga   4200

aacgcctggt atctttatag tcctgtcggg tttcgccacc tctgacttga gcgtcgattt   4260

ttgtgatgct cgtcaggggg gcggagccta tggaaaaacg ccagcaacgc ggccttttta   4320

cggttcctgg ccttttgctg gccttttgct cacatgttct ttcctgcgtt atcccctgat   4380

tctgtggata accgtattac cgcctttgag tgagctgata ccgctcgccg cagccgaacg   4440

accgagcgca gcgagtcagt gagcgaggaa gcggaagagc gcctgatgcg gtattttctc   4500

cttacgcatc tgtgcggtat ttcacaccgc atatggtgca ctctcagtac aatctgctct   4560

gatgccgcat agttaagcca gtatacactc cgctatcgct acgtgactgg gtcatggctg   4620

cgccccgaca cccgccaaca cccgctgacg cgccctgacg ggcttgtctg ctcccggcat   4680

ccgcttacag acaagctgtg accgtctccg ggagctgcat gtgtcagagg ttttcaccgt   4740

catcaccgaa acgcgcgagg cagggtgcct tgatgtgggc gccggcggtc gagtggcgac   4800

ggcgcggctt gtccgcgccc tggtagattg cctggccgta ggccagccat ttttgagcgg   4860

ccagcggccg cgataggccg acgcgaagcg gcggggcgta gggagcgcag cgaccgaagg   4920

gtaggcgctt tttgcagctc ttcggctgtg cgctggccag acagttatgc acaggccagg   4980

cgggttttaa gagttttaat aagttttaaa gagttttagg cggaaaaatc gcctttttttc   5040

tcttttatat cagtcactta catgtgtgac cggttcccaa tgtacggctt tgggttccca   5100

atgtacgggt tccggttccc aatgtacggc tttgggttcc caatgtacgt gctatccaca   5160

ggaaagagac cttttcgacc tttttcccct gctagggcaa tttgccctag catctgctcc   5220

gtacattagg aaccggcgga tgcttcgccc tcgatcaggt tgcggtagcg catgactagg   5280

atcgggccag cctgccccgc ctcctccttc aaatcgtact ccggcaggtc atttgacccg   5340

atcagcttgc gcacggtgaa acagaacttc ttgaactctc cggcgctgcc actgcgttcg   5400

tagatcgtct tgaacaacca tctggcttct gccttgcctg cggcgcggcg tgccaggcgg   5460

tagagaaaac ggccgatgcc gggatcgatc aaaaagtaat cggggtgaac cgtcagcacg   5520

tccgggttct tgccttctgt gatctcgcgg tacatccaat cagctagctc gatctcgatg   5580

tactccggcc gcccggtttc gctctttacg atcttgtagc ggctaatcaa ggcttcaccc   5640

tcggataccg tcaccaggcg gccgttcttg gccttcttcg tacgctgcat ggcaacgtgc   5700

gtggtgttta accgaatgca ggtttctacc aggtcgtctt tctgctttcc gccatcggct   5760

cgccggcaga acttgagtac gtccgcaacg tgtggacgga acacgcggcc gggcttgtct   5820

cccttccctt cccggtatcg gttcatggat tcggttagat gggaaaccgc catcagtacc   5880

aggtcgtaat cccacacact ggccatgccg gccggccctg cggaaacctc tacgtgcccg   5940

tctggaagct cgtagcggat cacctcgcca gctcgtcggt cacgcttcga cagacggaaa   6000

acggccacgt ccatgatgct gcgactatcg cgggtgccca cgtcatagag catcggaacg   6060

aaaaaatctg gttgctcgtc gcccttgggc ggcttcctaa tcgacggcgc accggctgcc   6120

ggcggttgcc gggattcttt gcggattcga tcagcggccg cttgccacga ttcaccgggg   6180

cgtgcttctg cctcgatgcg ttgccgctgg gcggcctgcg cggccttcaa cttctccacc   6240

aggtcatcac ccagcgccgc gccgatttgt accgggccgg atggtttgcg accgtcacgc   6300

cgattcctcg ggcttggggg ttccagtgcc attgcagggc cggcagacaa cccagccgct   6360
```

```
tacgcctggc caaccgcccg ttcctccaca catggggcat tccacggcgt cggtgcctgg   6420
ttgttcttga ttttccatgc cgcctccttt agccgctaaa attcatctac tcatttattc   6480
atttgctcat ttactctggt agctgcgcga tgtattcaga tagcagctcg gtaatggtct   6540
tgccttggcg taccgcgtac atcttcagct tggtgtgatc ctccgccggc aactgaaagt   6600
tgacccgctt catggctggc gtgtctgcca ggctggccaa cgttgcagcc ttgctgctgc   6660
gtgcgctcgg acggccggca cttagcgtgt ttgtgctttt gctcattttc tctttacctc   6720
attaactcaa atgagttttg atttaatttc agcggccagc gcctggacct cgcgggcagc   6780
gtcgccctcg ggttctgatt caagaacggt tgtgccggcg gcggcagtgc ctgggtagct   6840
cacgcgctgc gtgatacggg actcaagaat gggcagctcg tacccggcca gcgcctcggc   6900
aacctcaccg ccgatgcgcg tgcctttgat cgcccgcgac acgacaaagg ccgcttgtag   6960
ccttccatcc gtgacctcaa tgcgctgctt aaccagctcc accaggtcgg cggtggccca   7020
tatgtcgtaa gggcttggct gcaccggaat cagcacgaag tcggctgcct tgatcgcgga   7080
cacagccaag tccgccgcct ggggcgctcc gtcgatcact acgaagtcgc gccggccgat   7140
ggccttcacg tcgcggtcaa tcgtcgggcg gtcgatgccg acaacggtta gcggttgatc   7200
ttcccgcacg gccgcccaat cgcgggcact gccctgggga tcggaatcga ctaacagaac   7260
atcggccccg gcgagttgca gggcgcgggc tagatgggtt gcgatggtcg tcttgcctga   7320
cccgcctttc tggttaagta cagcgataac cttcatgcgt tccccttgcg tatttgttta   7380
tttactcatc gcatcatata cgcagcgacc gcatgacgca agctgtttta ctcaaataca   7440
catcaccttt ttagacggcg gcgctcggtt tcttcagcgg ccaagctggc cggccaggcc   7500
gccagcttgg catcagacaa accggccagg atttcatgca gccgcacggt tgagacgtgc   7560
gcgggcggct cgaacacgta cccggccgcg atcatctccg cctcgatctc ttcggtaatg   7620
aaaaacggtt cgtcctggcc gtcctggtgc ggtttcatgc ttgttcctct tggcgttcat   7680
tctcggcggc cgccagggcg tcggcctcgg tcaatgcgtc ctcacggaag gcaccgcgcc   7740
gcctggcctc ggtgggcgtc acttcctcgc tgcgctcaag tgcgcggtac agggtcgagc   7800
gatgcacgcc aagcagtgca gccgcctctt tcacggtgcg gccttcctgg tcgatcagct   7860
cgcgggcgtg cgcgatctgt gccggggtga gggtagggcg gggccaaac ttcacgcctc   7920
gggccttggc ggcctcgcgc ccgctccggg tgcggtcgat gattagggaa cgctcgaact   7980
cggcaatgcc ggcgaacacg gtcaacacca tgcggccggc cggcgtggtg gtgtcggccc   8040
acggctctgc caggctacgc aggcccgcgc cggcctcctg gatgcgctcg gcaatgtcca   8100
gtaggtcgcg ggtgctgcgg gccaggcggt ctagcctggt cactgtcaca acgtcgccag   8160
ggcgtaggtg gtcaagcatc ctggccagct ccgggcggtc gcgcctggtg ccggtgatct   8220
tctcggaaaa cagcttggtg cagccggccg cgtgcagttc ggcccgttgg ttggtcaagt   8280
cctggtcgtc ggtgctgacg cgggcatagc ccagcaggcc agcggcggcg ctcttgttca   8340
tggcgtaatg tctccggttc tagtcgcaag tattctactt tatgcgacta aaacacgcga   8400
caagaaaacg ccaggaaaag ggcagggcgg cagcctgtcg cgtaacttag gacttgtgcg   8460
acatgtcgtt ttcagaagac ggctgcactg aacgtcagaa gccgactgca ctatagcagc   8520
ggaggggttg gatcaaagta ctttgatccc gaggggaacc ctgtggttgg catgcacata   8580
caaatggacg aacggataaa ccttttcacg cccttttaaa tatccgttat tctaataaac   8640
gctcttttct cttaggttta cccgccaata tatcctgtca aacactgata gtttaaactg   8700
aaggcgggaa acgacaatct gatccaagct caagctgctc tagcattcgc cattcaggct   8760
```

```
gcgcaactgt tgggaagggc gatcggtgcg ggcctcttcg ctattacgcc agctggcgaa   8820

agggggatgt gctgcaaggc gattaagttg ggtaacgcca gggttttccc agtcacgacg   8880

ttgtaaaacg acggccagtg ccaagcttct agagatcgta cccctggatt ttggttttag   8940

gaattagaaa ttttattgat agaagtattt tacaaataca aatacatact aagggtttct   9000

tatatgctca acacatgagc gaaaccctat aagaacccta attcccttat ctgggaacta   9060

ctcacacatt attatagaga gagatagatt tgtagagaga gactggtgat ttcagcgggc   9120

atgcgtcgac gagctcccgg ggctgaggtt taattaagga tccttaatta agcctcagcc   9180

tgcaggtcgt cctctccaaa tgaaatgaac ttccttatat agaggaaggg tcttgcgaag   9240

gatagtggga ttgtgcgtca tcccttacgt cagtggagat atcacatcaa tccacttgct   9300

ttgaagacgt ggttggaacg tcttcttttt ccacgatgct cctcgtgggt gggggtccat   9360

ctttgggacc actgtcggca gaggcatctt gaacgatagc ctttccttta tcgcaatgat   9420

ggcatttgta ggtgccacct tccttttcta ctgtcctttt gatgaagtga cagatagctg   9480

ggcaatggaa tccgaggagg tttcccgata ttaccctttg ttgaaaagtc tcaatagccc   9540

tttggtcttc tgagactgta tctttgatat tcttggagta gacgagagtg tcgtgctcca   9600

ccatgttatc acatcaatcc acttgctttg aagacgtggt tggaacgtct tctttttcca   9660

cgatgctcct cgtgggtggg ggtccatctt tgggaccact gtcggcagag gcatcttgaa   9720

cgatagcctt tcctttatcg caatgatggc atttgtaggt gccaccttcc ttttctactg   9780

tccttttgat gaagtgacag atagctgggc aatggaatcc gaggaggttt cccgatatta   9840

ccctttgttg aaaagtctca atagcccttt ggtcttctga gactgtatct ttgatattct   9900

tggagtagac gagagtgtcg tgctccacca tgttgacgga tctctagaag cttgcatgcc   9960

tgcaggtcga ctctagagga tccccgggta ccgagctcga att                   10003
```

<210> SEQ ID NO 8
<211> LENGTH: 7053
<212> TYPE: DNA
<213> ORGANISM: Artificial Sequence
<220> FEATURE:
<223> OTHER INFORMATION: synthetic pUNI33
<220> FEATURE:
<221> NAME/KEY: misc_feature
<222> LOCATION: (1)..(7053)

<400> SEQUENCE: 8

```
ggcctcgtga tacgcctatt tttataggtt aatgtcatga taataatggt ttcttagacg     60

tcaggtggca cttttcgggg aaatgtgcgc ggaaccccta tttgtttatt tttctaaata    120

cattcaaata tgtatccgct catgagacaa taaccctgat aaatgcttca ataatattga    180

aaaaggaaga gtatgagtat tcaacatttc cgtgtcgccc ttattccctt ttttgcggca    240

ttttgccttc ctgtttttgc tcacccagaa acgctggtga aagtaaaaga tgctgaagat    300

cagttgggtg cacgagtggg ttacatcgaa ctggatctca acagcggtaa gatccttgag    360

agttttcgcc ccgaagaacg ttttccaatg atgagcactt ttaaagttct gctatgtggc    420

gcggtattat cccgtattga cgccgggcaa gagcaactcg gtcgccgcat acactattct    480

cagaatgact tggttgagta ctcaccagtc acagaaaagc atcttacgga tggcatgaca    540

gtaagagaat tatgcagtgc tgccataacc atgagtgata acactgcggc caacttactt    600

ctgacaacga tcggaggacc gaaggagcta accgcttttt tgcacaacat gggggatcat    660

gtaactcgcc ttgatcgttg ggaaccggag ctgaatgaag ccataccaaa cgacgagcgt    720
```

```
gacaccacga tgcctgtagc aatggcaaca acgttgcgca aactattaac tggcgaacta    780
cttactctag cttcccggca acaattaata gactggatgg aggcggataa agttgcagga    840
ccacttctgc gctcggccct tccggctggc tggtttattg ctgataaatc tggagccggt    900
gagcgtgggt ctcgcggtat cattgcagca ctggggccag atggtaagcc ctcccgtatc    960
gtagttatct acacgacggg gagtcaggca actatggatg aacgaaatag acagatcgct   1020
gagataggtg cctcactgat taagcattgg taactgtcag accaagttta ctcatatata   1080
ctttagattg atttaaaact tcatttttaa tttaaaagga tctaggtgaa gatccttttt   1140
gataatctca tgaccaaaat cccttaacgt gagttttcgt tccactgagc gtcagacccc   1200
gtagaaaaga tcaaaggatc ttcttgagat cctttttttc tgcgcgtaat ctgctgcttg   1260
caaacaaaaa aaccaccgct accagcggtg gtttgtttgc cggatcaaga gctaccaact   1320
ctttttccga aggtaactgg cttcagcaga gcgcagatac caaatactgt ccttctagtg   1380
tagccgtagt taggccacca cttcaagaac tctgtagcac cgcctacata cctcgctctg   1440
ctaatcctgt taccagtggc tgctgccagt ggcgataagt cgtgtcttac cgggttggac   1500
tcaagacgat agttaccgga taaggcgcag cggtcgggct gaacgggggg ttcgtgcaca   1560
cagcccagct tggagcgaac gacctacacc gaactgagat acctacagcg tgagctatga   1620
gaaagcgcca cgcttcccga agggagaaag gcggacaggt atccggtaag cggcagggtc   1680
ggaacaggag agcgcacgag ggagcttcca gggggaaacg cctggtatct ttatagtcct   1740
gtcgggtttc gccacctctg acttgagcgt cgatttttgt gatgctcgtc aggggggcgg   1800
agcctatgga aaaacgccag caacgcggcc tttttacggt tcctggcctt ttgctggcct   1860
tttgctcaca tgttctttcc tgcgttatcc cctgattctg tggataaccg tattaccgcc   1920
tttgagtgag ctgataccgc tcgccgcagc cgaacgaccg agcgcagcga gtcagtgagc   1980
gaggaagcgg aagagcgccc aatacgcaaa ccgcctctcc ccgcgcgttg gccgattcat   2040
taatgcagct ggcacgacag gtttcccgac tggaaagcaa ttggcagtga gcgcaacgca   2100
attaatgtga gttagctcac tcattaggca ccccaggctt tacactttat gcttccggct   2160
cgtataatgt gtggaattgt gagcggataa caatttcaca caggaggttt aaactttaaa   2220
catgtcaaaa gagacgtctt ttgttaagaa tgctgaggaa cttgcaaagc aaaaaatgga   2280
tgctattaac cctgaacttt cttcaaaatt taaattttta ataaaattcc tgtctcagtt   2340
tcctgaagct tgctctaaac ctcgttcaaa aaaaatgcag aataaagttg gtcaagagga   2400
acatattgaa tatttagctc gtagttttca tgagagtcga ttgccaagaa aacccacgcc   2460
acctacaacg gttcctgatg aggtggttag catagttctt aatataagtt ttaatataca   2520
gcctgaaaat cttgagagaa taaaagaaga acatcgattt tccatggcag ctgagaatat   2580
tgtaggagat cttctagaaa gattaacaag acgaactcca attcactgtt ccttgcattc   2640
taaaacctta aataccagaa aacagctttt tcaaagttgt tttcaaagtt ggcgtataac   2700
atagtatcga cggagccgat tttgaaaccg cggtgatcac aggcagcaac gctctgtcat   2760
cgttacaatc aacatgctac cctccgcgag atcatccgtg tttcaaaccc ggcagcttag   2820
ttgccgttct tccgaatagc atcggtaaca tgagcaaagt ctgccgcctt acaacggctc   2880
tcccgctgac gccgtcccgg actgatgggc tgcctgtatc gagtggtgat tttgtgccga   2940
gctgccggtc ggggagctgt tggctggctg gtggcaggat atattgtggt gtaaacaaat   3000
tgacgcttag acaacttaat aacacattgc ggacgttttt aatgtactga attaacgccg   3060
```

```
aattaattcg ggggatctgg attttagtac tggattttgg ttttaggaat tagaaatttt   3120
attgatagaa gtattttaca aatacaaata catactaagg gtttcttata tgctcaacac   3180
atgagcgaaa ccctatagga accctaattc ccttatctgg gaactactca cacattatta   3240
tggagaaact cgagcttgtc gatcgacaga tccggtcggc atctactcta tttctttgcc   3300
ctcggacgag tgctggggcg tcggtttcca ctatcggcga gtacttctac acagccatcg   3360
gtccagacgg ccgcgcttct gcgggcgatt tgtgtacgcc cgacagtccc ggctccggat   3420
cggacgattg cgtcgcatcg accctgcgcc caagctgcat catcgaaatt gccgtcaacc   3480
aagctctgat agagttggtc aagaccaatg cggagcatat acgcccggag tcgtggcgat   3540
cctgcaagct ccggatgcct ccgctcgaag tagcgcgtct gctgctccat acaagccaac   3600
cacggcctcc agaagaagat gttggcgacc tcgtattggg aatccccgaa catcgcctcg   3660
ctccagtcaa tgaccgctgt tatgcggcca ttgtccgtca ggacattgtt ggagccgaaa   3720
tccgcgtgca cgaggtgccg gacttcgggg cagtcctcgg cccaaagcat cagctcatcg   3780
agagcctgcg cgacggacgc actgacggtg tcgtccatca cagtttgcca gtgatacaca   3840
tggggatcag caatcgcgca tatgaaatca cgccatgtag tgtattgacc gattccttgc   3900
ggtccgaatg ggccgaaccc gctcgtctgg ctaagatcgg ccgcagcgat cgcatccata   3960
gcctccgcga ccggttgtag aacagcgggc agttcggttt caggcaggtc ttgcaacgtg   4020
acaccctgtg cacggcggga gatgcaatag gtcaggctct cgctaaactc cccaatgtca   4080
agcacttccg gaatcgggag cgcggccgat gcaaagtgcc gataaacata acgatctttg   4140
tagaaaccat cggcgcagct atttacccgc aggacatatc cacgccctcc tacatcgaag   4200
ctgaaagcac gagattcttc gccctccgag agctgcatca ggtcggagac gctgtcgaac   4260
ttttcgatca gaaacttctc gacagacgtc gcggtgagtt caggcttttt catatctcat   4320
tgccccccgg gatctgcgaa agctcgagag agatagattt gtagagagag actggtgatt   4380
tcagcgtgtc ctctccaaat gaaatgaact tccttatata gaggaaggtc ttgcgaagga   4440
tagtgggatt gtgcgtcatc ccttacgtca gtggagatat cacatcaatc cacttgcttt   4500
gaagacgtgg ttggaacgtc ttctttttcc acgatgctcc tcgtgggtgg gggtccatct   4560
ttgggaccac tgtcggcaga ggcatcttga acgatagcct ttcctttatc gcaatgatgg   4620
catttgtagg tgccaccttc cttttctact gtccttttga tgaagtgaca gatagctggg   4680
caatggaatc cgaggaggtt tcccgatatt accctttgtt gaaaagtctc aatagccctt   4740
tggtcttctg agactgtatc tttgatattc ttggagtaga cgagagtgtc gtgctccacc   4800
atgttatcac atcaatccac ttgctttgaa gacgtggttg gaacgtcttc tttttccacg   4860
atgctcctcg tgggtggggg tccatctttg ggaccactgt cggcagaggc atcttgaacg   4920
atagcctttc ctttatcgca atgatggcat ttgtaggtgc caccttcctt ttctactgtc   4980
cttttgatga agtgacagat agctgggcaa tggaatccga ggaggtttcc cgatattacc   5040
ctttgttgaa aagtctcaat agccctttgg tcttctgaga ctgtatcttt gatattcttg   5100
gagtagacga gagtgtcgtg ctccaccatg ttggcaagct gctctagcca atacgcaaac   5160
cgcctctccc cgcgcgttgg ccgattcatt aatgcagctg gcacgacagg tttcccgact   5220
ggaaagcggg cagtgagcgc aacgcaatta atgtgagtta gctcactcat taggcacccc   5280
aggctttaca ctttatgctt ccggctcgta tgttgtgtgg aattgtgagc ggataacaat   5340
ttcacacagg aaacagctat gaccatgatt acgaattcga gctcggtacc cggggatcct   5400
ctagagtcga cctgcaggca tgcaagcttc tagagatccg tcaacatggt ggagcacgac   5460
```

```
actctcgtct actccaagaa tatcaaagat acagtctcag aagaccaaag ggctattgag   5520

acttttcaac aaagggtaat atcgggaaac ctcctcggat tccattgccc agctatctgt   5580

cacttcatca aaaggacagt agaaaaggaa ggtggcacct acaaatgcca tcattgcgat   5640

aaaggaaagg ctatcgttca agatgcctct gccgacagtg gtcccaaaga tggaccccca   5700

cccacgagga gcatcgtgga aaaagaagac gttccaacca cgtcttcaaa gcaagtggat   5760

tgatgtgata acatggtgga gcacgacact ctcgtctact ccaagaatat caaagataca   5820

gtctcagaag accaaagggc tattgagact tttcaacaaa gggtaatatc gggaaacctc   5880

ctcggattcc attgcccagc tatctgtcac ttcatcaaaa ggacagtaga aaaggaaggt   5940

ggcacctaca aatgccatca ttgcgataaa ggaaaggcta tcgttcaaga tgcctctgcc   6000

gacagtggtc ccaaagatgg acccccaccc acgaggagca tcgtggaaaa agaagacgtt   6060

ccaaccacgt cttcaaagca agtggattga tgtgatatct ccactgacgt aagggatgac   6120

gcacaatccc actatccttc gcaagaccct tcctctatat aaggaagttc atttcatttg   6180

gagaggacga cctgcaggct gaggcttaat taaggatcct taattaaacc tcagccccgg   6240

gagctcgtcg acgcatgccc gctgaaatca ccagtctctc tctacaaatc tatctctctc   6300

tataataatg tgtgagtagt tcccagataa gggaattagg gttcttatag ggtttcgctc   6360

atgtgttgag catataagaa acccttagta tgtatttgta tttgtaaaat acttctatca   6420

ataaaatttc taattcctaa aaccaaaatc caggggtacg atctctagaa gcttggcact   6480

ggccgtcgtt ttacaacgtc gtgactggga aaaccctggc gttacccaac ttaatcgcct   6540

tgcagcacat ccccctttcg ccagctggcg taatagcgaa gaggcccgca ccgatcgccc   6600

ttcccaacag ttgcgcagcc tgaatggcga atgctagagc agcttgagct tggatcagat   6660

tgtcgtttcc cgccttcagt ttatcttgct gaaaaactcg agccatccgg aagatctggc   6720

ggccgctctc cctatagtga gtcgtattac gccggatgga tatggtgttc aggcacaagt   6780

gttaaagcag ttgattttat tcactatgat gaaaaaaaca atgaatggaa cctgctccaa   6840

gttaaaaata gagataatac cgaaaactca tcgagtagta agattagaga taatacaaca   6900

ataaaaaaat ggtttagaac ttactcacag cgtgatgcta ctaattggga caattttcca   6960

gatgaagtat catctaagaa tttaaatgaa gaagacttca gagcttttgt taaaaattat   7020

ttggcaaaaa taatataatt cggctgcagg ggc                                 7053
```

<210> SEQ ID NO 9
<211> LENGTH: 8700
<212> TYPE: DNA
<213> ORGANISM: Artificial Sequence
<220> FEATURE:
<223> OTHER INFORMATION: synthetic pUNI33 PTS
<220> FEATURE:
<221> NAME/KEY: misc_feature
<222> LOCATION: (1)..(8700)

<400> SEQUENCE: 9

```
ggcctcgtga tacgcctatt tttataggtt aatgtcatga taataatggt ttcttagacg     60

tcaggtggca cttttcgggg aaatgtgcgc ggaaccccta tttgtttatt tttctaaata    120

cattcaaata tgtatccgct catgagacaa taaccctgat aaatgcttca ataatattga    180

aaaaggaaga gtatgagtat tcaacatttc cgtgtcgccc ttattccctt ttttgcggca    240

ttttgccttc ctgtttttgc tcacccagaa acgctggtga aagtaaaaga tgctgaagat    300

cagttgggtg cacgagtggg ttacatcgaa ctggatctca acagcggtaa gatccttgag    360
```

```
agttttcgcc ccgaagaacg ttttccaatg atgagcactt ttaaagttct gctatgtggc    420
gcggtattat cccgtattga cgccgggcaa gagcaactcg gtcgccgcat acactattct    480
cagaatgact tggttgagta ctcaccagtc acagaaaagc atcttacgga tggcatgaca    540
gtaagagaat tatgcagtgc tgccataacc atgagtgata acactgcggc caacttactt    600
ctgacaacga tcggaggacc gaaggagcta accgcttttt tgcacaacat gggggatcat    660
gtaactcgcc ttgatcgttg ggaaccggag ctgaatgaag ccataccaaa cgacgagcgt    720
gacaccacga tgcctgtagc aatggcaaca acgttgcgca aactattaac tggcgaacta    780
cttactctag cttcccggca acaattaata gactggatgg aggcggataa agttgcagga    840
ccacttctgc gctcggccct tccggctggc tggtttattg ctgataaatc tggagccggt    900
gagcgtgggt ctcgcggtat cattgcagca ctggggccag atggtaagcc ctcccgtatc    960
gtagttatct acacgacggg gagtcaggca actatggatg aacgaaatag acagatcgct   1020
gagataggtg cctcactgat taagcattgg taactgtcag accaagttta ctcatatata   1080
ctttagattg atttaaaact tcatttttaa tttaaaagga tctaggtgaa gatccttttt   1140
gataatctca tgaccaaaat cccttaacgt gagttttcgt tccactgagc gtcagacccc   1200
gtagaaaaga tcaaaggatc ttcttgagat cctttttttc tgcgcgtaat ctgctgcttg   1260
caaacaaaaa aaccaccgct accagcggtg gtttgtttgc cggatcaaga gctaccaact   1320
ctttttccga aggtaactgg cttcagcaga gcgcagatac caaatactgt ccttctagtg   1380
tagccgtagt taggccacca cttcaagaac tctgtagcac cgcctacata cctcgctctg   1440
ctaatcctgt taccagtggc tgctgccagt ggcgataagt cgtgtcttac cgggttggac   1500
tcaagacgat agttaccgga taaggcgcag cggtcgggct gaacgggggg ttcgtgcaca   1560
cagcccagct tggagcgaac gacctacacc gaactgagat acctacagcg tgagctatga   1620
gaaagcgcca cgcttcccga agggagaaag gcggacaggt atccggtaag cggcagggtc   1680
ggaacaggag agcgcacgag ggagcttcca gggggaaacg cctggtatct ttatagtcct   1740
gtcgggtttc gccacctctg acttgagcgt cgatttttgt gatgctcgtc aggggggcgg   1800
agcctatgga aaaacgccag caacgcggcc tttttacggt tcctggcctt ttgctggcct   1860
tttgctcaca tgttctttcc tgcgttatcc cctgattctg tggataaccg tattaccgcc   1920
tttgagtgag ctgataccgc tcgccgcagc cgaacgaccg agcgcagcga gtcagtgagc   1980
gaggaagcgg aagagcgccc aatacgcaaa ccgcctctcc ccgcgcgttg gccgattcat   2040
taatgcagct ggcacgacag gtttcccgac tggaaagcaa ttggcagtga gcgcaacgca   2100
attaatgtga gttagctcac tcattaggca ccccaggctt tacactttat gcttccggct   2160
cgtataatgt gtggaattgt gagcggataa caatttcaca caggaggttt aaactttaaa   2220
catgtcaaaa gagacgtctt ttgttaagaa tgctgaggaa cttgcaaagc aaaaaatgga   2280
tgctattaac cctgaacttt cttcaaaatt taaattttta ataaaattcc tgtctcagtt   2340
tcctgaagct tgctctaaac ctcgttcaaa aaaaatgcag aataaagttg gtcaagagga   2400
acatattgaa tatttagctc gtagttttca tgagagtcga ttgccaagaa aacccacgcc   2460
acctacaacg gttcctgatg aggtggttag catagttctt aatataagtt ttaatataca   2520
gcctgaaaat cttgagagaa taaaagaaga acatcgattt tccatggcag ctgagaatat   2580
tgtaggagat cttctagaaa gattaacaag acgaactcca attcactgtt ccttgcattc   2640
taaaacctta aataccagaa aacagctttt tcaaagttgt tttcaaagtt ggcgtataac   2700
```

-continued atagtatcga cggagccgat tttgaaaccg cggtgatcac aggcagcaac gctctgtcat 2760
cgttacaatc aacatgctac cctccgcgag atcatccgtg tttcaaaccc ggcagcttag 2820
ttgccgttct tccgaatagc atcggtaaca tgagcaaagt ctgccgcctt acaacggctc 2880
tcccgctgac gccgtcccgg actgatgggc tgcctgtatc gagtggtgat tttgtgccga 2940
gctgccggtc ggggagctgt tggctggctg gtggcaggat atattgtggt gtaaacaaat 3000
tgacgcttag acaacttaat aacacattgc ggacgttttt aatgtactga attaacgccg 3060
aattaattcg ggggatctgg attttagtac tggattttgg ttttaggaat tagaaatttt 3120
attgatagaa gtattttaca aatacaaata catactaagg gtttcttata tgctcaacac 3180
atgagcgaaa ccctatagga accctaattc ccttatctgg gaactactca cacattatta 3240
tggagaaact cgagcttgtc gatcgacaga tccggtcggc atctactcta tttctttgcc 3300
ctcggacgag tgctggggcg tcggtttcca ctatcggcga gtacttctac acagccatcg 3360
gtccagacgg ccgcgcttct gcgggcgatt tgtgtacgcc cgacagtccc ggctccggat 3420
cggacgattg cgtcgcatcg accctgcgcc caagctgcat catcgaaatt gccgtcaacc 3480
aagctctgat agagttggtc aagaccaatg cggagcatat acgcccggag tcgtggcgat 3540
cctgcaagct ccggatgcct ccgctcgaag tagcgcgtct gctgctccat acaagccaac 3600
cacggcctcc agaagaagat gttggcgacc tcgtattggg aatccccgaa catcgcctcg 3660
ctccagtcaa tgaccgctgt tatgcggcca ttgtccgtca ggacattgtt ggagccgaaa 3720
tccgcgtgca cgaggtgccg gacttcgggg cagtcctcgg cccaaagcat cagctcatcg 3780
agagcctgcg cgacggacgc actgacggtg tcgtccatca cagtttgcca gtgatacaca 3840
tggggatcag caatcgcgca tatgaaatca cgccatgtag tgtattgacc gattccttgc 3900
ggtccgaatg ggccgaaccc gctcgtctgg ctaagatcgg ccgcagcgat cgcatccata 3960
gcctccgcga ccggttgtag aacagcgggc agttcggttt caggcaggtc ttgcaacgtg 4020
acaccctgtg cacggcggga gatgcaatag gtcaggctct cgctaaactc cccaatgtca 4080
agcacttccg gaatcgggag cgcggccgat gcaaagtgcc gataaacata acgatctttg 4140
tagaaaccat cggcgcagct atttacccgc aggacatatc cacgccctcc tacatcgaag 4200
ctgaaagcac gagattcttc gccctccgag agctgcatca ggtcggagac gctgtcgaac 4260
ttttcgatca gaaacttctc gacagacgtc gcggtgagtt caggcttttt catatctcat 4320
tgcccccggg gatctgcgaa agctcgagag agatagattt gtagagagag actggtgatt 4380
tcagcgtgtc ctctccaaat gaaatgaact tccttatata gaggaaggtc ttgcgaagga 4440
tagtgggatt gtgcgtcatc ccttacgtca gtggagatat cacatcaatc cacttgcttt 4500
gaagacgtgg ttggaacgtc ttcttttttcc acgatgctcc tcgtgggtgg gggtccatct 4560
ttgggaccac tgtcggcaga ggcatcttga acgatagcct ttcctttatc gcaatgatgg 4620
catttgtagg tgccaccttc cttttctact gtccttttga tgaagtgaca gatagctggg 4680
caatggaatc cgaggaggtt tcccgatatt accctttgtt gaaaagtctc aatagccctt 4740
tggtcttctg agactgtatc tttgatattc ttggagtaga cgagagtgtc gtgctccacc 4800
atgttatcac atcaatccac ttgctttgaa gacgtggttg gaacgtcttc tttttccacg 4860
atgctcctcg tgggtggggg tccatctttg ggaccactgt cggcagaggc atcttgaacg 4920
atagcctttc ctttatcgca atgatggcat ttgtaggtgc caccttcctt ttctactgtc 4980
cttttgatga agtgacagat agctgggcaa tggaatccga ggaggtttcc cgatattacc 5040
ctttgttgaa aagtctcaat agccctttgg tcttctgaga ctgtatcttt gatattcttg 5100

```
gagtagacga gagtgtcgtg ctccaccatg ttggcaagct gctctagcca atacgcaaac   5160
cgcctctccc cgcgcgttgg ccgattcatt aatgcagctg gcacgacagg tttcccgact   5220
ggaaagcggg cagtgagcgc aacgcaatta atgtgagtta gctcactcat taggcacccc   5280
aggctttaca ctttatgctt ccggctcgta tgttgtgtgg aattgtgagc ggataacaat   5340
ttcacacagg aaacagctat gaccatgatt acgaattcga gctcggtacc cggggatcct   5400
ctagagtcga cctgcaggca tgcaagcttc tagagatccg tcaacatggt ggagcacgac   5460
actctcgtct actccaagaa tatcaaagat acagtctcag aagaccaaag ggctattgag   5520
acttttcaac aaagggtaat atcgggaaac ctcctcggat tccattgccc agctatctgt   5580
cacttcatca aaaggacagt agaaaaggaa ggtggcacct acaaatgcca tcattgcgat   5640
aaaggaaagg ctatcgttca agatgcctct gccgacagtg gtcccaaaga tggaccccca   5700
cccacgagga gcatcgtgga aaaagaagac gttccaacca cgtcttcaaa gcaagtggat   5760
tgatgtgata acatggtgga gcacgacact ctcgtctact ccaagaatat caaagataca   5820
gtctcagaag accaaagggc tattgagact tttcaacaaa gggtaatatc gggaaacctc   5880
ctcggattcc attgcccagc tatctgtcac ttcatcaaaa ggacagtaga aaaggaaggt   5940
ggcacctaca aatgccatca ttgcgataaa ggaaaggcta tcgttcaaga tgcctctgcc   6000
gacagtggtc ccaaagatgg acccccaccc acgaggagca tcgtggaaaa agaagacgtt   6060
ccaaccacgt cttcaaagca agtggattga tgtgatatct ccactgacgt aagggatgac   6120
gcacaatccc actatccttc gcaagaccct tcctctatat aaggaagttc atttcatttg   6180
gagaggacga cctgcaggct gaggcttaat atggagttgt atgcccaaag tgttggagtg   6240
ggtgctgctt ctcgtcctct tgcgaatttt catccatgtg tgtggggaga caaattcatt   6300
gtctacaacc cacaatcatg ccaggctgga gagagagaag aggctgagga gctgaaagtg   6360
gagctgaaaa gagagctgaa ggaagcatca gacaactaca tgcggcaact gaaaatggtg   6420
gatgcaatac aacgattagg cattgactat ctttttgtgg aagatgttga tgaagctttg   6480
aagaatctgt ttgaaatgtt tgatgctttc tgcaagaata atcatgacat gcacgccact   6540
gctctcagct ttcgccttct cagacaacat ggatacagag tttcatgtga agtttttgaa   6600
aagtttaagg atggcaaaga tggatttaag gttccaaatg aggatggagc ggttgcagtc   6660
cttgaattct tcgaagccac gcatctcaga gtccatggag aagacgtcct tgataatgct   6720
tttgacttca ctaggaacta cttggaatca gtctatgcaa ctttgaacga tccaaccgcg   6780
aaacaagtcc acaacgcatt gaatgagttc tcttttcgaa gaggattgcc acgcgtggaa   6840
gcaaggaagt acatatcaat ctacgagcaa tacgcatctc atcacaaagg cttgctcaaa   6900
cttgctaagc tggatttcaa cttggtacaa gctttgcaca gaagggagct gagtgaagat   6960
tctaggtggt ggaagacttt acaagtgccc acaaagctat cattcgttag agatcgattg   7020
gtggagtcct acttctgggc ttcgggatct tatttcgaac cgaattattc ggtagctagg   7080
atgattttag caaaagggct ggctgtatta tctcttatgg atgatgtgta tgatgcatat   7140
ggtacttttg aggaattaca aatgttcaca gatgcaatcg aaaggtggga tgcttcatgt   7200
ttagataaac ttccagatta catgaaaata gtatacaagg ccctttttgga tgtgtttgag   7260
gaagttgacg aggagttgat caagctaggc gcaccatatc gagcctacta tggaaaagaa   7320
gccatgaaat acgccgcgag agcttacatg gaagaggccc aatggaggga gcaaaagcac   7380
aaacccacaa ccaaggagta tatgaagctg gcaaccaaga catgtggcta cataactcta   7440
```

```
ataatattat catgtcttgg agtggaagag ggcattgtga ccaaagaagc cttcgattgg   7500

gtgttctccc gacctccttt catcgaggct acattaatca ttgccaggct cgtcaatgat   7560

attacaggac acgagtttga gaaaaaacga gagcacgttc gcactgcagt agaatgctac   7620

atggaagagc acaaagtggg gaagcaagag gtggtgtctg aattctacaa ccaaatggag   7680

tcagcatgga aggacattaa tgaggggttc ctcagaccag ttgaatttcc aatccctcta   7740

ctttatctta ttctcaattc agtccgaaca cttgaggtta tttacaaaga gggcgattcg   7800

tatacacacg tgggtcctgc aatgcaaaac atcatcaagc agttgtacct tcaccctgtt   7860

ccatattaaa ttaaacctca gccccgggag ctcgtcgacg catgcccgct gaaatcacca   7920

gtctctctct acaaatctat ctctctctat aataatgtgt gagtagttcc cagataaggg   7980

aattagggtt cttatagggt ttcgctcatg tgttgagcat ataagaaacc cttagtatgt   8040

atttgtattt gtaaaatact tctatcaata aaatttctaa ttcctaaaac caaaatccag   8100

gggtacgatc tctagaagct tggcactggc cgtcgtttta caacgtcgtg actgggaaaa   8160

ccctggcgtt acccaactta atcgccttgc agcacatccc cctttcgcca gctggcgtaa   8220

tagcgaagag gcccgcaccg atcgcccttc ccaacagttg cgcagcctga atggcgaatg   8280

ctagagcagc ttgagcttgg atcagattgt cgtttcccgc cttcagttta tcttgctgaa   8340

aaactcgagc catccggaag atctggcggc cgctctccct atagtgagtc gtattacgcc   8400

ggatggatat ggtgttcagg cacaagtgtt aaagcagttg attttattca ctatgatgaa   8460

aaaaacaatg aatggaacct gctccaagtt aaaaatagag ataataccga aaactcatcg   8520

agtagtaaga ttagagataa tacaacaata aaaaaatggt ttagaactta ctcacagcgt   8580

gatgctacta attgggacaa ttttccagat gaagtatcat ctaagaattt aaatgaagaa   8640

gacttcagag cttttgttaa aaattatttg gcaaaaataa tataattcgg ctgcaggggc   8700
```

```
<210> SEQ ID NO 10
<211> LENGTH: 8751
<212> TYPE: DNA
<213> ORGANISM: Artificial Sequence
<220> FEATURE:
<223> OTHER INFORMATION: synthetic pUNI33 STS
<220> FEATURE:
<221> NAME/KEY: misc_feature
<222> LOCATION: (1)..(8751)

<400> SEQUENCE: 10

ggcctcgtga tacgcctatt tttataggtt aatgtcatga taataatggt ttcttagacg     60

tcaggtggca cttttcgggg aaatgtgcgc ggaaccccta tttgtttatt tttctaaata    120

cattcaaata tgtatccgct catgagacaa taaccctgat aaatgcttca ataatattga    180

aaaaggaaga gtatgagtat tcaacatttc cgtgtcgccc ttattccctt ttttgcggca    240

ttttgccttc ctgtttttgc tcacccagaa acgctggtga aagtaaaaga tgctgaagat    300

cagttgggtg cacgagtggg ttacatcgaa ctggatctca acagcggtaa gatccttgag    360

agttttcgcc ccgaagaacg ttttccaatg atgagcactt ttaaagttct gctatgtggc    420

gcggtattat cccgtattga cgccgggcaa gagcaactcg gtcgccgcat acactattct    480

cagaatgact tggttgagta ctcaccagtc acagaaaagc atcttacgga tggcatgaca    540

gtaagagaat tatgcagtgc tgccataacc atgagtgata acactgcggc caacttactt    600

ctgacaacga tcggaggacc gaaggagcta accgcttttt tgcacaacat gggggatcat    660

gtaactcgcc ttgatcgttg ggaaccggag ctgaatgaag ccataccaaa cgacgagcgt    720
```

```
gacaccacga tgcctgtagc aatggcaaca acgttgcgca aactattaac tggcgaacta    780
cttactctag cttcccggca acaattaata gactggatgg aggcggataa agttgcagga    840
ccacttctgc gctcggccct tccggctggc tggtttattg ctgataaatc tggagccggt    900
gagcgtgggt ctcgcggtat cattgcagca ctggggccag atggtaagcc ctcccgtatc    960
gtagttatct acacgacggg gagtcaggca actatggatg aacgaaatag acagatcgct   1020
gagataggtg cctcactgat taagcattgg taactgtcag accaagttta ctcatatata   1080
ctttagattg atttaaaact tcatttttaa tttaaaagga tctaggtgaa gatccttttt   1140
gataatctca tgaccaaaat cccttaacgt gagttttcgt tccactgagc gtcagacccc   1200
gtagaaaaga tcaaaggatc ttcttgagat cctttttttc tgcgcgtaat ctgctgcttg   1260
caaacaaaaa aaccaccgct accagcggtg gtttgtttgc cggatcaaga gctaccaact   1320
ctttttccga aggtaactgg cttcagcaga gcgcagatac caaatactgt ccttctagtg   1380
tagccgtagt taggccacca cttcaagaac tctgtagcac cgcctacata cctcgctctg   1440
ctaatcctgt taccagtggc tgctgccagt ggcgataagt cgtgtcttac cgggttggac   1500
tcaagacgat agttaccgga taaggcgcag cggtcgggct gaacgggggg ttcgtgcaca   1560
cagcccagct tggagcgaac gacctacacc gaactgagat acctacagcg tgagctatga   1620
gaaagcgcca cgcttcccga agggagaaag gcggacaggt atccggtaag cggcagggtc   1680
ggaacaggag agcgcacgag ggagcttcca gggggaaacg cctggtatct ttatagtcct   1740
gtcgggtttc gccacctctg acttgagcgt cgatttttgt gatgctcgtc aggggggcgg   1800
agcctatgga aaaacgccag caacgcggcc tttttacggt tcctggcctt ttgctggcct   1860
tttgctcaca tgttctttcc tgcgttatcc cctgattctg tggataaccg tattaccgcc   1920
tttgagtgag ctgataccgc tcgccgcagc cgaacgaccg agcgcagcga gtcagtgagc   1980
gaggaagcgg aagagcgccc aatacgcaaa ccgcctctcc ccgcgcgttg gccgattcat   2040
taatgcagct ggcacgacag gtttcccgac tggaaagcaa ttggcagtga gcgcaacgca   2100
attaatgtga gttagctcac tcattaggca ccccaggctt tacactttat gcttccggct   2160
cgtataatgt gtggaattgt gagcggataa caatttcaca caggaggttt aaactttaaa   2220
catgtcaaaa gagacgtctt ttgttaagaa tgctgaggaa cttgcaaagc aaaaaatgga   2280
tgctattaac cctgaacttt cttcaaaatt taaatttta ataaaattcc tgtctcagtt    2340
tcctgaagct tgctctaaac ctcgttcaaa aaaaatgcag aataaagttg gtcaagagga   2400
acatattgaa tatttagctc gtagttttca tgagagtcga ttgccaagaa aacccacgcc   2460
acctacaacg gttcctgatg aggtggttag catagttctt aatataagtt ttaatataca   2520
gcctgaaaat cttgagagaa taaaagaaga acatcgattt tccatggcag ctgagaatat   2580
tgtaggagat cttctagaaa gattaacaag acgaactcca attcactgtt ccttgcattc   2640
taaaacctta aataccagaa aacagctttt tcaaagttgt tttcaaagtt ggcgtataac   2700
atagtatcga cggagccgat tttgaaaccg cggtgatcac aggcagcaac gctctgtcat   2760
cgttacaatc aacatgctac cctccgcgag atcatccgtg tttcaaaccc ggcagcttag   2820
ttgccgttct tccgaatagc atcggtaaca tgagcaaagt ctgccgcctt acaacggctc   2880
tcccgctgac gccgtcccgg actgatgggc tgcctgtatc gagtggtgat tttgtgccga   2940
gctgccggtc ggggagctgt tggctggctg gtggcaggat atattgtggt gtaaacaaat   3000
tgacgcttag acaacttaat aacacattgc ggacgttttt aatgtactga attaacgccg   3060
aattaattcg gggatctgg atttagtac tggattttgg ttttaggaat tagaaatttt    3120
```

```
attgatagaa gtattttaca aatacaaata catactaagg gtttcttata tgctcaacac   3180
atgagcgaaa ccctatagga accctaattc ccttatctgg gaactactca cacattatta   3240
tggagaaact cgagcttgtc gatcgacaga tccggtcggc atctactcta tttctttgcc   3300
ctcggacgag tgctggggcg tcggtttcca ctatcggcga gtacttctac acagccatcg   3360
gtccagacgg ccgcgcttct gcgggcgatt tgtgtacgcc cgacagtccc ggctccggat   3420
cggacgattg cgtcgcatcg accctgcgcc caagctgcat catcgaaatt gccgtcaacc   3480
aagctctgat agagttggtc aagaccaatg cggagcatat acgcccggag tcgtggcgat   3540
cctgcaagct ccggatgcct ccgctcgaag tagcgcgtct gctgctccat acaagccaac   3600
cacggcctcc agaagaagat gttggcgacc tcgtattggg aatccccgaa catcgcctcg   3660
ctccagtcaa tgaccgctgt tatgcggcca ttgtccgtca ggacattgtt ggagccgaaa   3720
tccgcgtgca cgaggtgccg gacttcgggg cagtcctcgg cccaaagcat cagctcatcg   3780
agagcctgcg cgacggacgc actgacggtg tcgtccatca cagtttgcca gtgatacaca   3840
tggggatcag caatcgcgca tatgaaatca cgccatgtag tgtattgacc gattccttgc   3900
ggtccgaatg ggccgaaccc gctcgtctgg ctaagatcgg ccgcagcgat cgcatccata   3960
gcctccgcga ccggttgtag aacagcgggc agttcggttt caggcaggtc ttgcaacgtg   4020
acaccctgtg cacggcggga gatgcaatag gtcaggctct cgctaaactc cccaatgtca   4080
agcacttccg gaatcgggag cgcggccgat gcaaagtgcc gataaacata acgatctttg   4140
tagaaaccat cggcgcagct atttacccgc aggacatatc cacgccctcc tacatcgaag   4200
ctgaaagcac gagattcttc gccctccgag agctgcatca ggtcggagac gctgtcgaac   4260
ttttcgatca gaaacttctc gacagacgtc gcggtgagtt caggcttttt catatctcat   4320
tgccccccgg gatctgcgaa agctcgagag agatagattt gtagagagag actggtgatt   4380
tcagcgtgtc ctctccaaat gaaatgaact tccttatata gaggaaggtc ttgcgaagga   4440
tagtgggatt gtgcgtcatc ccttacgtca gtggagatat cacatcaatc cacttgcttt   4500
gaagacgtgg ttggaacgtc ttcttttttcc acgatgctcc tcgtgggtgg gggtccatct   4560
ttgggaccac tgtcggcaga ggcatcttga acgatagcct ttcctttatc gcaatgatgg   4620
catttgtagg tgccaccttc cttttctact gtccttttga tgaagtgaca gatagctggg   4680
caatggaatc cgaggaggtt tcccgatatt accctttgtt gaaaagtctc aatagccctt   4740
tggtcttctg agactgtatc tttgatattc ttggagtaga cgagagtgtc gtgctccacc   4800
atgttatcac atcaatccac ttgctttgaa gacgtggttg gaacgtcttc tttttccacg   4860
atgctcctcg tgggtggggg tccatctttg ggaccactgt cggcagaggc atcttgaacg   4920
atagcctttc ctttatcgca atgatggcat ttgtaggtgc caccttcctt ttctactgtc   4980
cttttgatga agtgacagat agctgggcaa tggaatccga ggaggtttcc cgatattacc   5040
ctttgttgaa aagtctcaat agccctttgg tcttctgaga ctgtatcttt gatattcttg   5100
gagtagacga gagtgtcgtg ctccaccatg ttggcaagct gctctagcca atacgcaaac   5160
cgcctctccc cgcgcgttgg ccgattcatt aatgcagctg gcacgacagg tttcccgact   5220
ggaaagcggg cagtgagcgc aacgcaatta atgtgagtta gctcactcat taggcacccc   5280
aggctttaca ctttatgctt ccggctcgta tgttgtgtgg aattgtgagc ggataacaat   5340
ttcacacagg aaacagctat gaccatgatt acgaattcga gctcggtacc cggggatcct   5400
ctagagtcga cctgcaggca tgcaagcttc tagagatccg tcaacatggt ggagcacgac   5460
```

```
actctcgtct actccaagaa tatcaaagat acagtctcag aagaccaaag ggctattgag   5520
acttttcaac aaagggtaat atcgggaaac ctcctcggat tccattgccc agctatctgt   5580
cacttcatca aaaggacagt agaaaaggaa ggtggcacct acaaatgcca tcattgcgat   5640
aaaggaaagg ctatcgttca agatgcctct gccgacagtg gtcccaaaga tggaccccca   5700
cccacgagga gcatcgtgga aaaagaagac gttccaacca cgtcttcaaa gcaagtggat   5760
tgatgtgata acatggtgga gcacgacact ctcgtctact ccaagaatat caaagataca   5820
gtctcagaag accaaagggc tattgagact tttcaacaaa gggtaatatc gggaaacctc   5880
ctcggattcc attgcccagc tatctgtcac ttcatcaaaa ggacagtaga aaaggaaggt   5940
ggcacctaca aatgccatca ttgcgataaa ggaaaggcta tcgttcaaga tgcctctgcc   6000
gacagtggtc ccaaagatgg acccccaccc acgaggagca tcgtggaaaa agaagacgtt   6060
ccaaccacgt cttcaaagca agtggattga tgtgatatct ccactgacgt aagggatgac   6120
gcacaatccc actatccttc gcaagaccct tcctctatat aaggaagttc atttcatttg   6180
gagaggacga cctgcaggct gaggcttaat atggattctt ccaccgccac cgccatgaca   6240
gctccattca ttgatcctac tgatcatgtg aatctcaaaa ctgatactga tgcctcagag   6300
aatcgaagga tgggaaatta taaacccagc atttggaatt atgatttttt acaatcactt   6360
gcaactcatc acaatattgt ggaagagagg catctaaagc ttgctgagaa gctgaagggc   6420
caagtgaagt ttatgtttgg ggcaccaatg gagccgttag caaagctgga gcttgtggat   6480
gtggttcaaa ggcttgggct aaaccaccta tttgagacag agatcaagga agcgctgttt   6540
agtatttaca aggatgggag caatggatgg tggtttggcc accttcatgc gacatctctc   6600
cgatttaggc tgctacgaca gtgtgggctt tttattcccc aagatgtgtt taaaacgttc   6660
caaaacaaaa ctggggaatt tgatatgaaa ctgtgggaca acgtaaaagg gctgctgagc   6720
ttatatgaag cttcatactt gggatggaag ggtgaaaaca tcctagatga agccaaggcc   6780
ttcaccacca agtgcttgaa aagtgcatgg gaaaatatat ccgaaaagtg gttagccaaa   6840
agagtgaagc atgctttggc tttgcctttg cattggagag tccctcgaat cgaagctaga   6900
tggttcattg aggtatatga gcaagaagcg aatatgaacc caacactact caaactcgca   6960
aaattagact ttaatatggt gcaatcaatt catcagaaag agattgggga attagcaagg   7020
tggtgggtga ctactggctt ggataagtta gactttgcta ggaataattt actgcagagc   7080
tatatgtgga gctgcgcgat tgcttccgac ccgaagttca aacttgctag agaaactatt   7140
gtcgaaatcg gaagtgtact cacagttgtt gacgatggat atgacgtcta tggttcaatg   7200
gacgaacttg atctctacac aagctccgtt gaaaggtgga gctgtgtgaa aattgacaag   7260
ttgccaaaca cgttaaaatt aatttttatg tctatgttca acaagaccaa tgaggttggt   7320
cttcgagtcc agcatgagcg aggctacaat agcatcccta cttttatcaa agcgtgggtt   7380
gaacagtgta aatcatacca gaaagaagca agatggttcc acgggggaca cacgcctcca   7440
ttggaagaat atagcttgaa tggacttgtt tccataggat tccctctctt gttaatcaca   7500
ggctacgtgg caatcgctga gaacgaggct gcactggata aagtgcaccc ccttcctgat   7560
cttctgcact actcctccct ccttagtcgc ctcatcaatg atataggaac gtctccggat   7620
gagatggcaa gaggcgataa tctgaagtca atccattgtt acatgaacga aactggggct   7680
tccgaggaag ttgctcgtga gcacataaag ggagtaatcg aggagaattg gaaaatactg   7740
aatcagtgct gctttgatca atctcagttt caggagcctt ttataacctt caatttgaac   7800
tctgttcgag ggtctcattt cttctatgaa tttggggatg gctttggggt gacggatagc   7860
```

```
tggacaaagg ttgatatgaa gtccgttttg atcgacccta ttcctctcgg cgaggagtag   7920

attaaacctc agccccggga gctcgtcgac gcatgcccgc tgaaatcacc agtctctctc   7980

tacaaatcta tctctctcta taataatgtg tgagtagttc ccagataagg gaattagggt   8040

tcttataggg tttcgctcat gtgttgagca tataagaaac ccttagtatg tatttgtatt   8100

tgtaaaatac ttctatcaat aaaatttcta attcctaaaa ccaaaatcca ggggtacgat   8160

ctctagaagc ttggcactgg ccgtcgtttt acaacgtcgt gactgggaaa accctggcgt   8220

tacccaactt aatcgccttg cagcacatcc ccctttcgcc agctggcgta atagcgaaga   8280

ggcccgcacc gatcgccctt cccaacagtt gcgcagcctg aatggcgaat gctagagcag   8340

cttgagcttg gatcagattg tcgtttcccg ccttcagttt atcttgctga aaaactcgag   8400

ccatccggaa gatctggcgg ccgctctccc tatagtgagt cgtattacgc cggatggata   8460

tggtgttcag gcacaagtgt taaagcagtt gattttattc actatgatga aaaaaacaat   8520

gaatggaacc tgctccaagt taaaaataga gataataccg aaaactcatc gagtagtaag   8580

attagagata atacaacaat aaaaaaatgg tttagaactt actcacagcg tgatgctact   8640

aattgggaca attttccaga tgaagtatca tctaagaatt taaatgaaga agacttcaga   8700

gcttttgtta aaaattattt ggcaaaaata atataattcg gctgcagggg c            8751
```

<210> SEQ ID NO 11
<211> LENGTH: 11194
<212> TYPE: DNA
<213> ORGANISM: Artificial Sequence
<220> FEATURE:
<223> OTHER INFORMATION: synthetic pUNI33-TPSsa3-2A-TPS1132
<220> FEATURE:
<221> NAME/KEY: misc_feature
<222> LOCATION: (1)..(11194)

<400> SEQUENCE: 11

```
ggcctcgtga tacgcctatt tttataggtt aatgtcatga taataatggt ttcttagacg     60

tcaggtggca cttttcgggg aaatgtgcgc ggaaccccta tttgtttatt tttctaaata    120

cattcaaata tgtatccgct catgagacaa taaccctgat aaatgcttca ataatattga    180

aaaaggaaga gtatgagtat tcaacatttc cgtgtcgccc ttattccctt ttttgcggca    240

ttttgccttc ctgtttttgc tcacccagaa acgctggtga aagtaaaaga tgctgaagat    300

cagttgggtg cacgagtggg ttacatcgaa ctggatctca acagcggtaa gatccttgag    360

agttttcgcc ccgaagaacg ttttccaatg atgagcactt ttaaagttct gctatgtggc    420

gcggtattat cccgtattga cgccgggcaa gagcaactcg gtcgccgcat acactattct    480

cagaatgact tggttgagta ctcaccagtc acagaaaagc atcttacgga tggcatgaca    540

gtaagagaat tatgcagtgc tgccataacc atgagtgata acactgcggc caacttactt    600

ctgacaacga tcggaggacc gaaggagcta accgcttttt tgcacaacat gggggatcat    660

gtaactcgcc ttgatcgttg ggaaccggag ctgaatgaag ccataccaaa cgacgagcgt    720

gacaccacga tgcctgtagc aatggcaaca acgttgcgca aactattaac tggcgaacta    780

cttactctag cttcccggca acaattaata gactggatgg aggcggataa agttgcagga    840

ccacttctgc gctcggccct tccggctggc tggtttattg ctgataaatc tggagccggt    900

gagcgtgggt ctcgcggtat cattgcagca ctggggccag atggtaagcc ctcccgtatc    960

gtagttatct acacgacggg gagtcaggca actatggatg aacgaaatag acagatcgct   1020

gagataggtg cctcactgat taagcattgg taactgtcag accaagttta ctcatatata   1080
```

```
ctttagattg atttaaaact tcatttttaa tttaaaagga tctaggtgaa gatccttttt   1140
gataatctca tgaccaaaat cccttaacgt gagttttcgt tccactgagc gtcagacccc   1200
gtagaaaaga tcaaaggatc ttcttgagat cctttttttc tgcgcgtaat ctgctgcttg   1260
caaacaaaaa aaccaccgct accagcggtg gtttgtttgc cggatcaaga gctaccaact   1320
ctttttccga aggtaactgg cttcagcaga gcgcagatac caaatactgt ccttctagtg   1380
tagccgtagt taggccacca cttcaagaac tctgtagcac cgcctacata cctcgctctg   1440
ctaatcctgt taccagtggc tgctgccagt ggcgataagt cgtgtcttac cgggttggac   1500
tcaagacgat agttaccgga taaggcgcag cggtcgggct gaacgggggg ttcgtgcaca   1560
cagcccagct tggagcgaac gacctacacc gaactgagat acctacagcg tgagctatga   1620
gaaagcgcca cgcttcccga agggagaaag gcggacaggt atccggtaag cggcagggtc   1680
ggaacaggag agcgcacgag ggagcttcca gggggaaacg cctggtatct ttatagtcct   1740
gtcgggtttc gccacctctg acttgagcgt cgatttttgt gatgctcgtc aggggggcgg   1800
agcctatgga aaaacgccag caacgcggcc tttttacggt tcctggcctt ttgctggcct   1860
tttgctcaca tgttctttcc tgcgttatcc cctgattctg tggataaccg tattaccgcc   1920
tttgagtgag ctgataccgc tcgccgcagc cgaacgaccg agcgcagcga gtcagtgagc   1980
gaggaagcgg aagagcgccc aatacgcaaa ccgcctctcc ccgcgcgttg gccgattcat   2040
taatgcagct ggcacgacag gtttcccgac tggaaagcaa ttggcagtga gcgcaacgca   2100
attaatgtga gttagctcac tcattaggca ccccaggctt tacactttat gcttccggct   2160
cgtataatgt gtggaattgt gagcggataa caatttcaca caggaggttt aaactttaaa   2220
catgtcaaaa gagacgtctt ttgttaagaa tgctgaggaa cttgcaaagc aaaaaatgga   2280
tgctattaac cctgaacttt cttcaaaatt taaattttta ataaaattcc tgtctcagtt   2340
tcctgaagct tgctctaaac ctcgttcaaa aaaaatgcag aataaagttg gtcaagagga   2400
acatattgaa tatttagctc gtagttttca tgagagtcga ttgccaagaa aacccacgcc   2460
acctacaacg gttcctgatg aggtggttag catagttctt aatataagtt ttaatataca   2520
gcctgaaaat cttgagagaa taaaagaaga acatcgattt tccatggcag ctgagaatat   2580
tgtaggagat cttctagaaa gattaacaag acgaactcca attcactgtt ccttgcattc   2640
taaaacctta aataccagaa aacagctttt tcaaagttgt tttcaaagtt ggcgtataac   2700
atagtatcga cggagccgat tttgaaaccg cggtgatcac aggcagcaac gctctgtcat   2760
cgttacaatc aacatgctac cctccgcgag atcatccgtg tttcaaaccc ggcagcttag   2820
ttgccgttct tccgaatagc atcggtaaca tgagcaaagt ctgccgcctt acaacggctc   2880
tcccgctgac gccgtcccgg actgatgggc tgcctgtatc gagtggtgat tttgtgccga   2940
gctgccggtc ggggagctgt tggctggctg gtggcaggat atattgtggt gtaaacaaat   3000
tgacgcttag acaacttaat aacacattgc ggacgttttt aatgtactga attaacgccg   3060
aattaattcg ggggatctgg attttagtac tggattttgg ttttaggaat tagaaatttt   3120
attgatagaa gtattttaca aatacaaata catactaagg gtttcttata tgctcaacac   3180
atgagcgaaa ccctatagga accctaattc ccttatctgg gaactactca cacattatta   3240
tggagaaact cgagcttgtc gatcgacaga tccggtcggc atctactcta tttctttgcc   3300
ctcggacgag tgctggggcg tcggtttcca ctatcggcga gtacttctac acagccatcg   3360
gtccagacgg ccgcgcttct gcgggcgatt tgtgtacgcc cgacagtccc ggctccggat   3420
```

```
cggacgattg cgtcgcatcg accctgcgcc caagctgcat catcgaaatt gccgtcaacc   3480
aagctctgat agagttggtc aagaccaatg cggagcatat acgcccggag tcgtggcgat   3540
cctgcaagct ccggatgcct ccgctcgaag tagcgcgtct gctgctccat acaagccaac   3600
cacggcctcc agaagaagat gttggcgacc tcgtattggg aatccccgaa catcgcctcg   3660
ctccagtcaa tgaccgctgt tatgcggcca ttgtccgtca ggacattgtt ggagccgaaa   3720
tccgcgtgca cgaggtgccg gacttcgggg cagtcctcgg cccaaagcat cagctcatcg   3780
agagcctgcg cgacggacgc actgacggtg tcgtccatca cagtttgcca gtgatacaca   3840
tggggatcag caatcgcgca tatgaaatca cgccatgtag tgtattgacc gattccttgc   3900
ggtccgaatg ggccgaaccc gctcgtctgg ctaagatcgg ccgcagcgat cgcatccata   3960
gcctccgcga ccggttgtag aacagcgggc agttcggttt caggcaggtc ttgcaacgtg   4020
acaccctgtg cacggcggga gatgcaatag gtcaggctct cgctaaactc cccaatgtca   4080
agcacttccg gaatcgggag cgcggccgat gcaaagtgcc gataaacata acgatctttg   4140
tagaaaccat cggcgcagct atttacccgc aggacatatc cacgccctcc tacatcgaag   4200
ctgaaagcac gagattcttc gccctccgag agctgcatca ggtcggagac gctgtcgaac   4260
ttttcgatca gaaacttctc gacagacgtc gcggtgagtt caggcttttt catatctcat   4320
tgcccccggg gatctgcgaa agctcgagag agatagattt gtagagagag actggtgatt   4380
tcagcgtgtc ctctccaaat gaaatgaact tccttatata gaggaaggtc ttgcgaagga   4440
tagtgggatt gtgcgtcatc ccttacgtca gtggagatat cacatcaatc cacttgcttt   4500
gaagacgtgg ttggaacgtc ttcttttttcc acgatgctcc tcgtgggtgg gggtccatct   4560
ttgggaccac tgtcggcaga ggcatcttga acgatagcct ttcctttatc gcaatgatgg   4620
catttgtagg tgccaccttc cttttctact gtccttttga tgaagtgaca gatagctggg   4680
caatggaatc cgaggaggtt tcccgatatt accctttgtt gaaaagtctc aatagccctt   4740
tggtcttctg agactgtatc tttgatattc ttggagtaga cgagagtgtc gtgctccacc   4800
atgttatcac atcaatccac ttgctttgaa gacgtggttg gaacgtcttc tttttccacg   4860
atgctcctcg tgggtggggg tccatctttg ggaccactgt cggcagaggc atcttgaacg   4920
atagcctttc ctttatcgca atgatggcat ttgtaggtgc caccttcctt ttctactgtc   4980
cttttgatga agtgacagat agctgggcaa tggaatccga ggaggtttcc cgatattacc   5040
ctttgttgaa aagtctcaat agccctttgg tcttctgaga ctgtatcttt gatattcttg   5100
gagtagacga gagtgtcgtg ctccaccatg ttggcaagct gctctagcca atacgcaaac   5160
cgcctctccc cgcgcgttgg ccgattcatt aatgcagctg gcacgacagg tttcccgact   5220
ggaaagcggg cagtgagcgc aacgcaatta atgtgagtta gctcactcat taggcacccc   5280
aggctttaca ctttatgctt ccggctcgta tgttgtgtgg aattgtgagc ggataacaat   5340
ttcacacagg aaacagctat gaccatgatt acgaattcga gctcggtacc cggggatcct   5400
ctagagtcga cctgcaggca tgcaagcttc tagagatccg tcaacatggt ggagcacgac   5460
actctcgtct actccaagaa tatcaaagat acagtctcag aagaccaaag ggctattgag   5520
acttttcaac aaagggtaat atcgggaaac ctcctcggat tccattgccc agctatctgt   5580
cacttcatca aaaggacagt agaaaaggaa ggtggcacct acaaatgcca tcattgcgat   5640
aaaggaaagg ctatcgttca agatgcctct gccgacagtg gtcccaaaga tggaccccca   5700
cccacgagga gcatcgtgga aaaagaagac gttccaacca cgtcttcaaa gcaagtggat   5760
tgatgtgata acatggtgga gcacgacact ctcgtctact ccaagaatat caaagataca   5820
```

```
gtctcagaag accaaagggc tattgagact tttcaacaaa gggtaatatc gggaaacctc   5880

ctcggattcc attgcccagc tatctgtcac ttcatcaaaa ggacagtaga aaaggaaggt   5940

ggcacctaca aatgccatca ttgcgataaa ggaaaggcta tcgttcaaga tgcctctgcc   6000

gacagtggtc ccaaagatgg acccccaccc acgaggagca tcgtggaaaa agaagacgtt   6060

ccaaccacgt cttcaaagca agtggattga tgtgatatct ccactgacgt aagggatgac   6120

gcacaatccc actatccttc gcaagaccct tcctctatat aaggaagttc atttcatttg   6180

gagaggacga cctgcaggct gaggcttaat attcgccctt atgacttctg taaatttgag   6240

cagagcacca gcagcgatta cccggcgcag gctgcagcta cagccggaat ttcatgccga   6300

gtgttcatgg ctgaaaagca gcagcaaaca cgcgcccttg accttgagtt gccaaatccg   6360

tcctaagcaa ctctcccaaa tagctgaatt gagagtaaca agcctggatg cgtcgcaagc   6420

gagtgaaaaa gacatttccc ttgttcaaac tccgcataag gttgaggtta atgaaaagat   6480

cgaggagtca atcgagtacg tccaaaatct gttgatgacg tcgggcgacg ggcgaataag   6540

cgtgtcaccc tatgacacgg cagtgatcgc cctgatcaag gacttgaaag ggcgcgacgc   6600

cccgcagttt ccgtcatgtc tcgagtggat cgcgcaccac caactggctg atggctcatg   6660

gggcgacgaa ttcttctgta tttatgatcg gattctaaat acattggcat gtgtcgtagc   6720

cttgaaatca tggaaccttc actctgatat tattgaaaaa ggagtgacgt acatcaagga   6780

gaatgtgcat aaacttaaag gtgcaaatgt tgagcacagg acagcggggt tcgaacttgt   6840

ggttcctact tttatgcaaa tggccacaga tttgggcatc caagatctgc cctatgatca   6900

tcccctcatc aaggagattg ctgacacaaa acaacaaaga ttgaaagaga tacccaagga   6960

tttggtttac caaatgccaa cgaatttact gtacagttta gaagggttag gagatttgga   7020

gtgggaaagg ctactgaaac tgcagtcggg caatggctcc ttcctcactt cgccgtcgtc   7080

caccgccgcc gtcttgatgc ataccaaaga tgaaaaatgt ttgaaataca tcgaaaacgc   7140

cctcaagaat tgcgacggag gagcaccaca tacttatcca gtcgatatct tctcaagact   7200

ttgggcaatc gataggctac aacgcctagg aatttctcgt ttcttccagc acgagatcaa   7260

gtatttctta gatcacatcg aaagcgtttg ggaggagacc ggagttttca gtggaagata   7320

tacgaaattt agcgatattg atgacacgtc catgggcgtt aggcttctca aaatgcacgg   7380

atacgacgtc gatccaaatg tactaaaaca tttcaagcaa caagatggta aattttcctg   7440

ctacattggt caatcggtcg agtctgcatc tccaatgtac aatctttata gggctgctca   7500

actaagattt ccaggagaag aagttcttga agaagccact aaatttgcct ttaacttctt   7560

gcaagaaatg ctagtcaaag atcgacttca agaaagatgg gtgatatccg accacttatt   7620

tgatgagata aagctggggt tgaagatgcc atggtacgcc actctacccc gagtcgaggc   7680

tgcatattat ctagaccatt atgctggttc tggtgatgta tggattggca agagtttcta   7740

caggatgcca gaaatcagca atgatacata caaggagctt gcgatattgg atttcaacag   7800

atgccaaaca caacatcagt tggagtggat ccacatgcag gaatggtacg acagatgcag   7860

ccttagcgaa ttcgggataa gcaaaagaga gttgcttcgc tcttactttc tggccgcagc   7920

aaccatattc gaaccggaga gaactcaaga gaggcttctg tgggccaaaa ccagaattct   7980

ttctaagatg atcacttcat ttgtcaacat tagtggaaca acactatctt tggactacaa   8040

tttcaatggc ctcgatgaaa taattagtag tgccaatgaa gatcaaggac tggctgggac   8100

tctgctggca accttccatc aacttctaga cggattcgat atatacactc tccatcaact   8160
```

```
caaacatgtt tggagccaat ggttcatgaa agtgcagcaa ggagagggaa gcggcgggga   8220
agacgcggtg ctcctagcga acacgctcaa catctgcgcc ggcctcaacg aagacgtgtt   8280
gtccaacaat gaatacacgg ctctgtccac cctcacaaat aaaatctgca atcgcctcgc   8340
ccaaattcaa gacaataaga ttctccaagt tgtggatggg agcataaagg ataaggagct   8400
agaacaggat atgcaggcgt tggtgaagtt agtgcttcaa gaaaatggcg gcgccgtaga   8460
cagaaacatc agacacacgt ttttgtcggt ttccaagact ttctactacg atgcctacca   8520
cgacgatgag acgaccgatc ttcatatctt caaagtactc tttcgaccgg ttgtacaaac   8580
tttgaatttt gatttgctta agttggcagg agatgtggaa tctaacccag gacctatgtc   8640
gctcgccttc aacgtcggag ttacgccttt ctccggccaa agagttggga gcaggaaaga   8700
aaaatttcca gtccaaggat ttcctgtgac cacccccaat aggtcacgtc tcatcgttaa   8760
ctgcagcctt actacaatag atttcatggc gaaaatgaaa gagaatttca agagggaaga   8820
cgataaattt ccaacgacaa cgactcttcg atccgaagat ataccctcta atttgtgtat   8880
aatcgacacc cttcaaaggt tgggggtcga tcaattcttc caatatgaaa tcaacactat   8940
tctagataac acattcaggt tgtggcaaga aaaacacaaa gttatatatg gcaatgttac   9000
tactcatgca atggcattta ggcttttgcg agtgaaagga tacgaagttt catcagagga   9060
gttggctcca tatggtaacc aagaggctgt tagccagcaa acaaatgacc tgccgatgat   9120
tattgagctt tatagagcag caaatgagag aatatatgaa gaagagagga gtcttgaaaa   9180
aattcttgct tggactacca tctttctcaa taagcaagtg caagataact caattcccga   9240
caaaaaactg cacaaactgg tggaattcta cttgaggaat tacaaaggca taaccataag   9300
attgggagct agacgaaacc tcgagctata tgacatgacc tactatcaag ctctgaaatc   9360
tacaaacagg ttctctaatt tatgcaacga agattttcta gttttcgcaa agcaagattt   9420
cgatatacat gaagcccaga accagaaagg acttcaacaa ctgcaaaggt ggtatgcaga   9480
ttgtaggttg gacaccttaa actttggaag agatgtagtt attattgcta attatttggc   9540
ttcattaatt attggtgatc atgcgtttga ctatgttcgt ctcgcatttg ccaaaacatc   9600
tgtgcttgta acaattatgg atgatttttt cgactgtcat ggctctagtc aagagtgtga   9660
caagatcatt gaattagtaa aagaatggaa ggagaatccg gatgcagagt acggatctga   9720
ggagcttgag atccttttta tggcgttgta caatacagta aatgagttgg cggagagggc   9780
tcgtgttgaa caggggcgta gtgtcaaaga gtttctagtc aaactgtggg ttgaaatact   9840
ctcagctttc aagatagaat tagatacatg gagcaatggc acgcagcaaa gcttcgatga   9900
atacatttct tcgtcgtggt tgtcgaacgg ttcccggctg acaggtctcc tgacgatgca   9960
attcgtcgga gtaaaattgt ccgatgaaat gcttatgagt gaagagtgca ctgatttggc  10020
taggcatgtc tgtatggtcg gccggctgct caacgacgtg tgcagttctg agagggagcg  10080
cgaggaaaat attgcaggaa aaagttatag cattctacta gcaactgaga aagatggaag  10140
aaaagttagt gaagatgaag ccattgcaga gatcaatgaa atggttgaat atcactggag  10200
aaaagtgttg cagattgtgt ataaaaaaga aagcattttg ccaagaagat gcaaagatgt  10260
atttttggag atggctaagg gtacgtttta tgcttatggg atcaacgatg aattgacttc  10320
tcctcagcaa tccaaggaag atatgaaatc ctttgtcttt tgaattaaac ctcagccccg  10380
ggagctcgtc gacgcatgcc cgctgaaatc accagtctct ctctacaaat ctatctctct  10440
ctataataat gtgtgagtag ttcccagata agggaattag ggttcttata gggtttcgct  10500
catgtgttga gcatataaga aacccttagt atgtatttgt atttgtaaaa tacttctatc  10560
```

```
aataaaattt ctaattccta aaaccaaaat ccaggggtac gatctctaga agcttggcac  10620

tggccgtcgt tttacaacgt cgtgactggg aaaaccctgg cgttacccaa cttaatcgcc  10680

ttgcagcaca tccccctttc gccagctggc gtaatagcga agaggcccgc accgatcgcc  10740

cttcccaaca gttgcgcagc ctgaatggcg aatgctagag cagcttgagc ttggatcaga  10800

ttgtcgtttc ccgccttcag tttatcttgc tgaaaaactc gagccatccg gaagatctgg  10860

cggccgctct ccctatagtg agtcgtatta cgccggatgg atatggtgtt caggcacaag  10920

tgttaaagca gttgatttta ttcactatga tgaaaaaaac aatgaatgga acctgctcca  10980

agttaaaaat agagataata ccgaaaactc atcgagtagt aagattagag ataatacaac  11040

aataaaaaaa tggtttagaa cttactcaca gcgtgatgct actaattggg acaattttcc  11100

agatgaagta tcatctaaga atttaaatga agaagacttc agagcttttg ttaaaaatta  11160

tttggcaaaa ataatataat tcggctgcag gggc                              11194
```

<210> SEQ ID NO 12

<400> SEQUENCE: 12

000

<210> SEQ ID NO 13

<400> SEQUENCE: 13

000

<210> SEQ ID NO 14
<211> LENGTH: 7048
<212> TYPE: DNA
<213> ORGANISM: Artificial Sequence
<220> FEATURE:
<223> OTHER INFORMATION: synthetic pCL755
<220> FEATURE:
<221> NAME/KEY: misc_feature
<222> LOCATION: (1)..(7048)

<400> SEQUENCE: 14

```
ctttcctgcg ttatcccctg attctgtgga taaccgtatt accgctagcc aggaagagtt     60

tgtagaaacg caaaaaggcc atccgtcagg atggccttct gcttagtttg atgcctggca    120

gtttatggcg ggcgtcctgc ccgccaccct ccgggccgtt gcttcacaac gttcaaatcc    180

gctcccggcg gatttgtcct actcaggaga gcgttcaccg acaaacaaca gataaaacga    240

aaggcccagt cttccgactg agcctttcgt tttatttgat gcctggcagt tccctactct    300

cgcgttaacg ctagcatgga tctcgggccc caaataatga ttttattttg actgatagtg    360

acctgttcgt tgcaacaaat tgatgagcaa tgctttttta taatgccaag tttgtacaaa    420

aaagcaggct ctccaacata cttgctcttc cgttcacaca ttaagacact gtttccacag    480

ctctgaacta tcttgggctt ggaatctgtc caggaatcca gtttctgcaa tctaacatct    540

acaaaatgga ggaagatgac gccaatcata tgccgattgg atttgagatt gtcttcccag    600

cgatgatgga agatgccaag gcactgggac tggatttacc atacgatgcc actatcttgc    660

aacaaatctc ggctgaaaga gagaagaaaa tgaaaaagtg agctatcttg cctcatcaac    720

tcctcactct tgaaatgtca tcacagaatt agcgttaatg tccaggcctc tacagaagca    780

ctgctgaatg ggccaatctg cgaaaacgtg ttctcatttg cattcaatga actggaagca    840

gtaaattgtt ttgtgattga ttagagcagg attcctatgg cgatggtgta caagtacccc    900
```

```
actactttgc tgcattctct ggaaggcctg caccgggaag tggactggaa caagctcctc    960
cagctacagt ccgagaatgg ctcctttctg tattcacccg catccactgc atgcgcactt   1020
atgtacacaa aagatgtgaa gtgcttcgac tacttgaacc agctcctcat caagttcgac   1080
cacgcttgtc caaacgtgta ccccgttgat ctcttcgagc gtttgtggat ggtagaccgc   1140
ctacaaaggc tgggaatatc ccgctacttc gagcgagaaa tcagagactg tctacaatat   1200
gtataccggt atgccttcta tccatgagag acttgatttg gagtatatca caagacgtat   1260
tcaatttgtg atgttcggac tccacgattg gaaatttgcc ttgaacttat tctttgtcac   1320
gaatctttct gcttgcagat actggaagga ttgtggtatt ggctgggcaa gcaattcgtc   1380
cgtgcaggac gtggacgaca cggccatggc cttccgcctt ctccgcacac acggattcga   1440
cgtcaaggag gactgcttca gacagttttt caaagatggt gagttcttct gcttcgccgg   1500
ccagtccagc caagccgtca cgggaatgtt caacctcagc agagcatcgc aaacgctctt   1560
cccaggggaa tcactcctaa aaaaggccag aacctttttcc agaaactttt tgagaaccaa   1620
gcatgaaaac aatgaatgct tcgacaagtg gataatcacg aaggatctag cgggcgaggt   1680
ggaatacaat ctcacattcc cctggtatgc tagccttcct cgtcttgagc atcgcaccta   1740
cttggaccaa tatgggattg atgatatctg gattggcaag tcgctctaca aaatgccggc   1800
cgtcaccaac gaagtgtttc tcaaattggc caaagccgac ttcaacatgt gccaagctct   1860
tcacaagaag gaactcgagg gggggcccgg taccccctact ccaaaaaatgt caaagataca   1920
gtctcagaag accaaagggc tattgagact tttcaacaaa gggtaatttc gggaaacctc   1980
ctcggattcc attgcccagc tatctgtcac ttcatcgaaa ggacagtaga aaaggaaggt   2040
ggctcctaca aatgccatca ttgcgataaa ggaaaggcta tcattcaaga tgcctctgcc   2100
gacagtggtc ccaaagatgg acccccaccc acgaggagca tcgtggaaaa agaagacgtt   2160
ccaaccacgt cttcaaagca agtggattga tgtgacatct ccactgacgt aagggatgac   2220
gcacaatccc actatccttc gcaagaccct tcctctatat aaggaagttc atttcatttg   2280
gagaggacag cccaagcatg gagaaccgac ctgcaggcat gattgaacaa gatggattgc   2340
acgcaggttc tccggccgct tgggtggaga ggctattcgg ctatgactgg gcacaacaga   2400
caatcggctg ctctgatgcc gccgtgttcc ggctgtcagc gcaggggcgc ccggttcttt   2460
ttgtcaagac cgacctgtcc ggtgccctga atgaactcca agacgaggca gcgcggctat   2520
cgtggctggc cacgacgggc gttccttgcg cagctgtgct cgacgttgtc actgaagcgg   2580
gaagggactg gctgctattg ggcgaagtgc cggggcagga tctcctgtca tctcaccttg   2640
ctcctgccga gaaagtatcc atcatggctg atgcaatgcg gcggctgcat acgcttgatc   2700
cggctacctg cccattcgac caccaagcga aacatcgcat cgagcgagca cgtactcgga   2760
tggaagccgg tcttgtcgat caggatgatc tggacgaaga gcatcagggg ctcgcgccag   2820
ccgaactgtt cgccaggctc aaggcgcgga tgcccgacgg cgaggatctc gtcgtgaccc   2880
atggcgatgc ctgcttgccg aatatcatgg tggaaaatgg ccgcttttct ggattcatcg   2940
actgtggccg gctgggtgtg gcggaccgct atcaggacat agcgttggct acccgtgata   3000
ttgctgaaga gcttggcggc gaatgggctg accgcttcct cgtgctttac ggtatcgccg   3060
ctcccgattc gcagcgcatc gccttctatc gccttcttga cgagttcttc tgagcgggac   3120
tctggggttc ggacggtacg ctgaaatcac cagtctcttc tacaaatcta tctctctcta   3180
ttttctccat aaataatgtg tgagtagttt cccgataagg gaaattaggg ttcttatagg   3240
```

```
gtttcgctca tgtgttgagc atataagaaa cccttagtat gtatttgtat ttgtaaaata   3300
cttctatcaa taaaatttct aattcctaaa accaaaatcc agtactaaaa tccagatctc   3360
ctaaagtccc tatagatctt tgtcgtgaat ataaaccaga cacgagacga ctaaacctgg   3420
agcccagacg ccgttcgaag ctagaagtac cgcttaggca ggaggccgtt agggaaaaga   3480
tgctaaggca gggttggtta cgttgactcc cccgtaggtt tggtttaaat atgatgaagt   3540
ggacggaagg aaggaggaag acaaggaagg ataaggttgc aggccctgtg caaggtaaga   3600
agatggaaat ttgatagagg tacgctacta tacttatact atacgctaag ggaatgcttg   3660
tatttatacc ctataccccc taataacccc ttatcaattt aagaaataat ccgcataagc   3720
ccccgcttaa aaattggtat cagagccatg aataggtcta tgaccaaaac tcaagaggat   3780
aacgggcccc ccctcgagtt tgctagacag aaatccgtgg agtgctactt cgcaggcgct   3840
gcaaccatgt ttgagcccga aatggtgcag gcgaggctcg tttgggcacg ctgttgcgtg   3900
ctcaccaccg ttctagacga ttacttcgat cacggtacac ctgtggaaga gcttcgggtt   3960
tttgtgcagg ccgtaaggac ttggaatccc gagctcatca acggactacc tgagcaagcc   4020
aagattctct ttatgggact gtacaagact gtgaacacta tcgccgagga ggcattcatg   4080
gcacagaaac gagacgtaca tcatcatctc aagcattacg tgagtctttg tgcctacacc   4140
tctcttcagt gtaaacgtgt ttgatctgtg ccttaatcaa ttgaacaagg ttgggataga   4200
ctcgtctaac gtgattttcc tgtgctttga cttgtttgct gcagtgggac aaattgatca   4260
cttcagcttt gaaagaagcc gaatgggcag agtccggcta cgtccccacc ttcgacgagt   4320
atatggaagt cgctgaaatc tccgtcgcac tagagcccat tgtatgtagc actctcttct   4380
tcgccggcca taggctcgat gaggatgtgc ttgacagtta tgactaccat ctcgtcatgc   4440
atctcgtcaa ccgcgtaggt cgcatcctca acgacatcca aggaatgaag gtaatcgact   4500
cgctccacaa cccctacaac ctgagatcct atcttcgaaa cgttaaaccc tcaaaagagt   4560
cgcattgcta agtttcaatc atgaactgac aaggaaatat caatgccaca tatcgtattt   4620
cagagggaag ccagccaagg gaagatatcg agcgtgcaga tctacatgga ggagcatcca   4680
agtgtgcctt cagaggccat ggccatcgct catctgcagg aattggtcga caactccatg   4740
caacagctga catacgaagt gctgcgcttc actgcagtcc cgaagtcctg taagagaatc   4800
catttaaaca tggcgaagat catgcacgct ttctacaagg acactgatgg gttttcgtca   4860
ctgacagcca tgacagggtt tgtgaagaag gtgctcttcg agccagtacc tgaatagaat   4920
tctatcgcat aatccactta ctcgacatgc ataccaaagc gaaacatttg ccaattgcaa   4980
acgggtcctt ctagtgggta agcatcatgt aacataacca attagtccag aaatgtaaat   5040
gccgtaacgc aaatgtgcaa ttagctcctg tcaccgtcta ctatcagatc tgatagaatt   5100
gatgttgctc agactgtagc atcgtatcaa tctacgttgc catgtaagcc catttcatcc   5160
gatctattca agttataagg cttgctacat tttgcatctc cttccttgca gttattgatc   5220
tcaacccagc tttcttgtac aaagtgggca ttataagaaa gcattgctta tcaatttgtt   5280
gcaacgaaca ggtcactatc agtcaaaata aaatcattat ttgccatcca gctgcagctc   5340
tggcccgtgt ctcaaaatct ctgatgttac attgcacaag ataaaaatat atcatcatga   5400
acaataaaac tgtctgctta cataaacagt aatacaaggg gtgttatgag ccatattcaa   5460
cgggaaacgt cgaggccgcg attaaattcc aacatggatg ctgatttata tgggtataaa   5520
tgggctcgcg ataatgtcgg gcaatcaggt gcgacaatct atcgcttgta tgggaagccc   5580
gatgcgccag agttgtttct gaaacatggc aaaggtagcg ttgccaatga tgttacagat   5640
```

```
gagatggtca gactaaactg gctgacggaa tttatgcctc ttccgaccat caagcatttt   5700

atccgtactc ctgatgatgc atggttactc accactgcga tccccggaaa aacagcattc   5760

caggtattag aagaatatcc tgattcaggt gaaaatattg ttgatgcgct ggcagtgttc   5820

ctgcgccggt tgcattcgat tcctgtttgt aattgtcctt ttaacagcga tcgcgtattt   5880

cgtctcgctc aggcgcaatc acgaatgaat aacggtttgg ttgatgcgag tgattttgat   5940

gacgagcgta atggctggcc tgttgaacaa gtctggaaag aaatgcataa acttttgcca   6000

ttctcaccgg attcagtcgt cactcatggt gatttctcac ttgataacct tatttttgac   6060

gaggggaaat taataggttg tattgatgtt ggacgagtcg gaatcgcaga ccgataccag   6120

gatcttgcca tcctatggaa ctgcctcggt gagttttctc cttcattaca gaaacggctt   6180

tttcaaaaat atggtattga taatcctgat atgaataaat tgcagtttca tttgatgctc   6240

gatgagtttt tctaatcaga attggttaat tggttgtaac actggcagag cattacgctg   6300

acttgacggg acggcgcaag ctcatgacca aaatccctta acgtgagttt tcgttccact   6360

gagcgtcaga ccccgtagaa aagatcaaag gatcttcttg agatcctttt tttctgcgcg   6420

taatctgctg cttgcaaaca aaaaaaccac cgctaccagc ggtggtttgt ttgccggatc   6480

aagagctacc aactcttttt ccgaaggtaa ctggcttcag cagagcgcag ataccaaata   6540

ctgtccttct agtgtagccg tagttaggcc accacttcaa gaactctgta gcaccgccta   6600

catacctcgc tctgctaatc ctgttaccag tggctgctgc cagtggcgat aagtcgtgtc   6660

ttaccgggtt ggactcaaga cgatagttac cggataaggc gcagcggtcg ggctgaacgg   6720

ggggttcgtg cacacagccc agcttggagc gaacgaccta caccgaactg agatacctac   6780

agcgtgagct atgagaaagc gccacgcttc ccgaagggag aaaggcggac aggtatccgg   6840

taagcggcag ggtcggaaca ggagagcgca cgagggagct tccaggggga aacgcctggt   6900

atctttatag tcctgtcggg tttcgccacc tctgacttga gcgtcgattt ttgtgatgct   6960

cgtcaggggg gcggagccta tggaaaaacg ccagcaacgc ggccttttta cggttcctgg   7020

ccttttgctg gccttttgct cacatgtt                                       7048
```

<210> SEQ ID NO 15
<211> LENGTH: 8886
<212> TYPE: DNA
<213> ORGANISM: Artificial Sequence
<220> FEATURE:
<223> OTHER INFORMATION: synthetic pUNI33 tpPTS
<220> FEATURE:
<221> NAME/KEY: misc_feature
<222> LOCATION: (1)..(8886)

<400> SEQUENCE: 15

```
ggcctcgtga tacgcctatt tttataggtt aatgtcatga taataatggt ttcttagacg     60

tcaggtggca cttttcgggg aaatgtgcgc ggaaccccta tttgtttatt tttctaaata    120

cattcaaata tgtatccgct catgagacaa taaccctgat aaatgcttca ataatattga    180

aaaaggaaga gtatgagtat tcaacatttc cgtgtcgccc ttattccctt ttttgcggca    240

ttttgccttc ctgtttttgc tcacccagaa acgctggtga aagtaaaaga tgctgaagat    300

cagttgggtg cacgagtggg ttacatcgaa ctggatctca acagcggtaa gatccttgag    360

agttttcgcc ccgaagaacg ttttccaatg atgagcactt ttaaagttct gctatgtggc    420

gcggtattat cccgtattga cgccgggcaa gagcaactcg gtcgccgcat acactattct    480

cagaatgact tggttgagta ctcaccagtc acagaaaagc atcttacgga tggcatgaca    540
```

```
gtaagagaat tatgcagtgc tgccataacc atgagtgata acactgcggc caacttactt    600
ctgacaacga tcggaggacc gaaggagcta accgcttttt tgcacaacat gggggatcat    660
gtaactcgcc ttgatcgttg ggaaccggag ctgaatgaag ccataccaaa cgacgagcgt    720
gacaccacga tgcctgtagc aatggcaaca acgttgcgca aactattaac tggcgaacta    780
cttactctag cttcccggca acaattaata gactggatgg aggcggataa agttgcagga    840
ccacttctgc gctcggccct tccggctggc tggtttattg ctgataaatc tggagccggt    900
gagcgtgggt ctcgcggtat cattgcagca ctggggccag atggtaagcc ctcccgtatc    960
gtagttatct acacgacggg gagtcaggca actatggatg aacgaaatag acagatcgct   1020
gagataggtg cctcactgat taagcattgg taactgtcag accaagttta ctcatatata   1080
ctttagattg atttaaaact tcatttttaa tttaaaagga tctaggtgaa gatccttttt   1140
gataatctca tgaccaaaat cccttaacgt gagttttcgt tccactgagc gtcagacccc   1200
gtagaaaaga tcaaaggatc ttcttgagat cctttttttc tgcgcgtaat ctgctgcttg   1260
caaacaaaaa aaccaccgct accagcggtg gtttgtttgc cggatcaaga gctaccaact   1320
ctttttccga aggtaactgg cttcagcaga gcgcagatac caaatactgt ccttctagtg   1380
tagccgtagt taggccacca cttcaagaac tctgtagcac cgcctacata cctcgctctg   1440
ctaatcctgt taccagtggc tgctgccagt ggcgataagt cgtgtcttac cgggttggac   1500
tcaagacgat agttaccgga taaggcgcag cggtcgggct gaacgggggg ttcgtgcaca   1560
cagcccagct tggagcgaac gacctacacc gaactgagat acctacagcg tgagctatga   1620
gaaagcgcca cgcttcccga agggagaaag gcggacaggt atccggtaag cggcagggtc   1680
ggaacaggag agcgcacgag ggagcttcca gggggaaacg cctggtatct ttatagtcct   1740
gtcgggtttc gccacctctg acttgagcgt cgatttttgt gatgctcgtc aggggggcgg   1800
agcctatgga aaaacgccag caacgcggcc tttttacggt tcctggcctt ttgctggcct   1860
tttgctcaca tgttctttcc tgcgttatcc cctgattctg tggataaccg tattaccgcc   1920
tttgagtgag ctgataccgc tcgccgcagc cgaacgaccg agcgcagcga gtcagtgagc   1980
gaggaagcgg aagagcgccc aatacgcaaa ccgcctctcc ccgcgcgttg gccgattcat   2040
taatgcagct ggcacgacag gtttcccgac tggaaagcaa ttggcagtga gcgcaacgca   2100
attaatgtga gttagctcac tcattaggca ccccaggctt tacactttat gcttccggct   2160
cgtataatgt gtggaattgt gagcggataa caatttcaca caggaggttt aaactttaaa   2220
catgtcaaaa gagacgtctt ttgttaagaa tgctgaggaa cttgcaaagc aaaaaaatgga   2280
tgctattaac cctgaacttt cttcaaaatt taaattttta ataaaattcc tgtctcagtt   2340
tcctgaagct tgctctaaac ctcgttcaaa aaaaatgcag aataaagttg gtcaagagga   2400
acatattgaa tatttagctc gtagttttca tgagagtcga ttgccaagaa aacccacgcc   2460
acctacaacg gttcctgatg aggtggttag catagttctt aatataagtt ttaatataca   2520
gcctgaaaat cttgagagaa taaaagaaga acatcgattt tccatggcag ctgagaatat   2580
tgtaggagat cttctagaaa gattaacaag acgaactcca attcactgtt ccttgcattc   2640
taaaacctta aataccagaa aacagctttt tcaaagttgt tttcaaagtt ggcgtataac   2700
atagtatcga cggagccgat tttgaaaccg cggtgatcac aggcagcaac gctctgtcat   2760
cgttacaatc aacatgctac cctccgcgag atcatccgtg tttcaaaccc ggcagcttag   2820
ttgccgttct tccgaatagc atcggtaaca tgagcaaagt ctgccgcctt acaacggctc   2880
```

```
tcccgctgac gccgtcccgg actgatgggc tgcctgtatc gagtggtgat tttgtgccga   2940
gctgccggtc ggggagctgt tggctggctg gtggcaggat atattgtggt gtaaacaaat   3000
tgacgcttag acaacttaat aacacattgc ggacgttttt aatgtactga attaacgccg   3060
aattaattcg ggggatctgg attttagtac tggattttgg ttttaggaat tagaaatttt   3120
attgatagaa gtattttaca aatacaaata catactaagg gtttcttata tgctcaacac   3180
atgagcgaaa ccctatagga accctaattc ccttatctgg gaactactca cacattatta   3240
tggagaaact cgagcttgtc gatcgacaga tccggtcggc atctactcta tttctttgcc   3300
ctcggacgag tgctggggcg tcggtttcca ctatcggcga gtacttctac acagccatcg   3360
gtccagacgg ccgcgcttct gcgggcgatt tgtgtacgcc cgacagtccc ggctccggat   3420
cggacgattg cgtcgcatcg accctgcgcc caagctgcat catcgaaatt gccgtcaacc   3480
aagctctgat agagttggtc aagaccaatg cggagcatat acgcccggag tcgtggcgat   3540
cctgcaagct ccggatgcct ccgctcgaag tagcgcgtct gctgctccat acaagccaac   3600
cacggcctcc agaagaagat gttggcgacc tcgtattggg aatccccgaa catcgcctcg   3660
ctccagtcaa tgaccgctgt tatgcggcca ttgtccgtca ggacattgtt ggagccgaaa   3720
tccgcgtgca cgaggtgccg gacttcgggg cagtcctcgg cccaaagcat cagctcatcg   3780
agagcctgcg cgacggacgc actgacggtg tcgtccatca cagtttgcca gtgatacaca   3840
tggggatcag caatcgcgca tatgaaatca cgccatgtag tgtattgacc gattccttgc   3900
ggtccgaatg ggccgaaccc gctcgtctgg ctaagatcgg ccgcagcgat cgcatccata   3960
gcctccgcga ccggttgtag aacagcgggc agttcggttt caggcaggtc ttgcaacgtg   4020
acaccctgtg cacggcggga gatgcaatag gtcaggctct cgctaaactc cccaatgtca   4080
agcacttccg gaatcgggag cgcggccgat gcaaagtgcc gataaacata acgatctttg   4140
tagaaaccat cggcgcagct atttacccgc aggacatatc cacgccctcc tacatcgaag   4200
ctgaaagcac gagattcttc gccctccgag agctgcatca ggtcggagac gctgtcgaac   4260
ttttcgatca gaaacttctc gacagacgtc gcggtgagtt caggcttttt catatctcat   4320
tgcccccggg gatctgcgaa agctcgagag agatagattt gtagagagag actggtgatt   4380
tcagcgtgtc ctctccaaat gaaatgaact tccttatata gaggaaggtc ttgcgaagga   4440
tagtgggatt gtgcgtcatc ccttacgtca gtggagatat cacatcaatc cacttgcttt   4500
gaagacgtgg ttggaacgtc ttcttttttcc acgatgctcc tcgtgggtgg gggtccatct   4560
ttgggaccac tgtcggcaga ggcatcttga acgatagcct ttcctttatc gcaatgatgg   4620
catttgtagg tgccaccttc cttttctact gtccttttga tgaagtgaca gatagctggg   4680
caatggaatc cgaggaggtt tcccgatatt accctttgtt gaaaagtctc aatagccctt   4740
tggtcttctg agactgtatc tttgatattc ttggagtaga cgagagtgtc gtgctccacc   4800
atgttatcac atcaatccac ttgctttgaa gacgtggttg gaacgtcttc tttttccacg   4860
atgctcctcg tgggtggggg tccatctttg ggaccactgt cggcagaggc atcttgaacg   4920
atagcctttc ctttatcgca atgatggcat ttgtaggtgc caccttcctt ttctactgtc   4980
cttttgatga agtgacagat agctgggcaa tggaatccga ggaggtttcc cgatattacc   5040
ctttgttgaa aagtctcaat agccctttgg tcttctgaga ctgtatcttt gatattcttg   5100
gagtagacga gagtgtcgtg ctccaccatg ttggcaagct gctctagcca atacgcaaac   5160
cgcctctccc cgcgcgttgg ccgattcatt aatgcagctg gcacgacagg tttcccgact   5220
ggaaagcggg cagtgagcgc aacgcaatta atgtgagtta gctcactcat taggcacccc   5280
```

```
aggctttaca ctttatgctt ccggctcgta tgttgtgtgg aattgtgagc ggataacaat   5340
ttcacacagg aaacagctat gaccatgatt acgaattcga gctcggtacc cggggatcct   5400
ctagagtcga cctgcaggca tgcaagcttc tagagatccg tcaacatggt ggagcacgac   5460
actctcgtct actccaagaa tatcaaagat acagtctcag aagaccaaag ggctattgag   5520
acttttcaac aaagggtaat atcgggaaac ctcctcggat tccattgccc agctatctgt   5580
cacttcatca aaaggacagt agaaaaggaa ggtggcacct acaaatgcca tcattgcgat   5640
aaaggaaagg ctatcgttca agatgcctct gccgacagtg gtcccaaaga tggaccccca   5700
cccacgagga gcatcgtgga aaaagaagac gttccaacca cgtcttcaaa gcaagtggat   5760
tgatgtgata acatggtgga gcacgacact ctcgtctact ccaagaatat caaagataca   5820
gtctcagaag accaaagggc tattgagact tttcaacaaa gggtaatatc gggaaacctc   5880
ctcggattcc attgcccagc tatctgtcac ttcatcaaaa ggacagtaga aaaggaaggt   5940
ggcacctaca aatgccatca ttgcgataaa ggaaaggcta tcgttcaaga tgcctctgcc   6000
gacagtggtc ccaaagatgg acccccaccc acgaggagca tcgtggaaaa agaagacgtt   6060
ccaaccacgt cttcaaagca agtggattga tgtgatatct ccactgacgt aagggatgac   6120
gcacaatccc actatccttc gcaagaccct tcctctatat aaggaagttc atttcatttg   6180
gagaggacga cctgcaggct gaggcttaat atggcttcct ctatgctctc ctccgccgct   6240
gtggttacat ccccggctca ggccaccatg gtcgctccat tcaccggctt gaagtcatcc   6300
gctgcattcc cggtcacccg caagaccaac aaggacatca cttccatcgc aagcaacggg   6360
ggaagatcta gctgcatgaa ggagctcggc gcgcctatgg agttgtatgc ccaaagtgtt   6420
ggagtgggtg ctgcttctcg tcctcttgcg aattttcatc catgtgtgtg gggagacaaa   6480
ttcattgtct acaacccaca atcatgccag gctggagaga gagaagaggc tgaggagctg   6540
aaagtggagc tgaaaagaga gctgaaggaa gcatcagaca actacatgcg gcaactgaaa   6600
atggtggatg caatacaacg attaggcatt gactatcttt ttgtggaaga tgttgatgaa   6660
gctttgaaga atctgtttga aatgtttgat gctttctgca agaataatca tgacatgcac   6720
gccactgctc tcagctttcg ccttctcaga caacatggat acagagtttc atgtgaagtt   6780
tttgaaaagt ttaaggatgg caaagatgga tttaaggttc caaatgagga tggagcggtt   6840
gcagtccttg aattcttcga agccacgcat ctcagagtcc atggagaaga cgtccttgat   6900
aatgcttttg acttcactag gaactacttg gaatcagtct atgcaacttt gaacgatcca   6960
accgcgaaac aagtccacaa cgcattgaat gagttctctt ttcgaagagg attgccacgc   7020
gtggaagcaa ggaagtacat atcaatctac gagcaatacg catctcatca caaaggcttg   7080
ctcaaacttg ctaagctgga tttcaacttg gtacaagctt tgcacagaag ggagctgagt   7140
gaagattcta ggtggtggaa gactttacaa gtgcccacaa agctatcatt cgttagagat   7200
cgattggtgg agtcctactt ctgggcttcg ggatcttatt tcgaaccgaa ttattcggta   7260
gctaggatga ttttagcaaa agggctggct gtattatctc ttatggatga tgtgtatgat   7320
gcatatggta cttttgagga attacaaatg ttcacagatg caatcgaaag gtgggatgct   7380
tcatgtttag ataaacttcc agattacatg aaaatagtat acaaggccct tttggatgtg   7440
tttgaggaag ttgacgagga gttgatcaag ctaggcgcac catatcgagc ctactatgga   7500
aaagaagcca tgaaatacgc cgcgagagct tacatggaag aggcccaatg gagggagcaa   7560
aagcacaaac ccacaaccaa ggagtatatg aagctggcaa ccaagacatg tggctacata   7620
```

```
actctaataa tattatcatg tcttggagtg gaagagggca ttgtgaccaa agaagccttc   7680

gattgggtgt tctcccgacc tcctttcatc gaggctacat taatcattgc caggctcgtc   7740

aatgatatta caggacacga gtttgagaaa aaacgagagc acgttcgcac tgcagtagaa   7800

tgctacatgg aagagcacaa agtggggaag caagaggtgg tgtctgaatt ctacaaccaa   7860

atggagtcag catggaagga cattaatgag gggttcctca gaccagttga atttccaatc   7920

cctctacttt atcttattct caattcagtc cgaacacttg aggttattta caaagagggc   7980

gattcgtata cacacgtggg tcctgcaatg caaaacatca tcaagcagtt gtaccttcac   8040

cctgttccat attaaattaa acctcagccc cgggagctcg tcgacgcatg cccgctgaaa   8100

tcaccagtct ctctctacaa atctatctct ctctataata atgtgtgagt agttcccaga   8160

taagggaatt agggttctta tagggtttcg ctcatgtgtt gagcatataa gaaaccctta   8220

gtatgtattt gtatttgtaa aatacttcta tcaataaaat ttctaattcc taaaaccaaa   8280

atccaggggt acgatctcta gaagcttggc actggccgtc gttttacaac gtcgtgactg   8340

ggaaaaccct ggcgttaccc aacttaatcg ccttgcagca catcccccctt tcgccagctg   8400

gcgtaatagc gaagaggccc gcaccgatcg cccttcccaa cagttgcgca gcctgaatgg   8460

cgaatgctag agcagcttga gcttggatca gattgtcgtt tcccgccttc agtttatctt   8520

gctgaaaaac tcgagccatc cggaagatct ggcggccgct ctccctatag tgagtcgtat   8580

tacgccggat ggatatggtg ttcaggcaca agtgttaaag cagttgattt tattcactat   8640

gatgaaaaaa acaatgaatg gaacctgctc caagttaaaa atagagataa taccgaaaac   8700

tcatcgagta gtaagattag agataataca acaataaaaa aatggtttag aacttactca   8760

cagcgtgatg ctactaattg ggacaatttt ccagatgaag tatcatctaa gaatttaaat   8820

gaagaagact tcagagcttt tgttaaaaat tatttggcaa aaataatata attcggctgc   8880

aggggc                                                              8886
```

<210> SEQ ID NO 16
<211> LENGTH: 8937
<212> TYPE: DNA
<213> ORGANISM: Artificial Sequence
<220> FEATURE:
<223> OTHER INFORMATION: synthetic pUNI33 tpSTS
<220> FEATURE:
<221> NAME/KEY: misc_feature
<222> LOCATION: (1)..(8757)

<400> SEQUENCE: 16

```
ggcctcgtga tacgcctatt tttataggtt aatgtcatga taataatggt ttcttagacg     60

tcaggtggca cttttcgggg aaatgtgcgc ggaaccccta tttgtttatt tttctaaata    120

cattcaaata tgtatccgct catgagacaa taaccctgat aaatgcttca ataatattga    180

aaaaggaaga gtatgagtat tcaacatttc cgtgtcgccc ttattccctt ttttgcggca    240

ttttgccttc ctgtttttgc tcacccagaa acgctggtga aagtaaaaga tgctgaagat    300

cagttgggtg cacgagtggg ttacatcgaa ctggatctca acagcggtaa gatccttgag    360

agttttcgcc ccgaagaacg ttttccaatg atgagcactt ttaaagttct gctatgtggc    420

gcggtattat cccgtattga cgccgggcaa gagcaactcg gtcgccgcat acactattct    480

cagaatgact tggttgagta ctcaccagtc acagaaaagc atcttacgga tggcatgaca    540

gtaagagaat tatgcagtgc tgccataacc atgagtgata acactgcggc caacttactt    600

ctgacaacga tcggaggacc gaaggagcta accgcttttt tgcacaacat gggggatcat    660
```

```
gtaactcgcc ttgatcgttg ggaaccggag ctgaatgaag ccataccaaa cgacgagcgt    720
gacaccacga tgcctgtagc aatggcaaca acgttgcgca aactattaac tggcgaacta    780
cttactctag cttcccggca acaattaata gactggatgg aggcggataa agttgcagga    840
ccacttctgc gctcggccct tccggctggc tggtttattg ctgataaatc tggagccggt    900
gagcgtgggt ctcgcggtat cattgcagca ctggggccag atggtaagcc ctcccgtatc    960
gtagttatct acacgacggg gagtcaggca actatggatg aacgaaatag acagatcgct   1020
gagataggtg cctcactgat taagcattgg taactgtcag accaagttta ctcatatata   1080
ctttagattg atttaaaact tcatttttaa tttaaaagga tctaggtgaa gatccttttt   1140
gataatctca tgaccaaaat cccttaacgt gagttttcgt tccactgagc gtcagacccc   1200
gtagaaaaga tcaaaggatc ttcttgagat cctttttttc tgcgcgtaat ctgctgcttg   1260
caaacaaaaa aaccaccgct accagcggtg gtttgtttgc cggatcaaga gctaccaact   1320
ctttttccga aggtaactgg cttcagcaga gcgcagatac caaatactgt ccttctagtg   1380
tagccgtagt taggccacca cttcaagaac tctgtagcac cgcctacata cctcgctctg   1440
ctaatcctgt taccagtggc tgctgccagt ggcgataagt cgtgtcttac cgggttggac   1500
tcaagacgat agttaccgga taaggcgcag cggtcgggct gaacgggggg ttcgtgcaca   1560
cagcccagct tggagcgaac gacctacacc gaactgagat acctacagcg tgagctatga   1620
gaaagcgcca cgcttcccga agggagaaag gcggacaggt atccggtaag cggcagggtc   1680
ggaacaggag agcgcacgag ggagcttcca gggggaaacg cctggtatct ttatagtcct   1740
gtcgggtttc gccacctctg acttgagcgt cgatttttgt gatgctcgtc aggggggcgg   1800
agcctatgga aaaacgccag caacgcggcc tttttacggt tcctggcctt ttgctggcct   1860
tttgctcaca tgttctttcc tgcgttatcc cctgattctg tggataaccg tattaccgcc   1920
tttgagtgag ctgataccgc tcgccgcagc cgaacgaccg agcgcagcga gtcagtgagc   1980
gaggaagcgg aagagcgccc aatacgcaaa ccgcctctcc ccgcgcgttg gccgattcat   2040
taatgcagct ggcacgacag gtttcccgac tggaaagcaa ttggcagtga gcgcaacgca   2100
attaatgtga gttagctcac tcattaggca ccccaggctt tacactttat gcttccggct   2160
cgtataatgt gtggaattgt gagcggataa caatttcaca caggaggttt aaactttaaa   2220
catgtcaaaa gagacgtctt ttgttaagaa tgctgaggaa cttgcaaagc aaaaaatgga   2280
tgctattaac cctgaacttt cttcaaaatt taaattttta ataaaattcc tgtctcagtt   2340
tcctgaagct tgctctaaac ctcgttcaaa aaaaatgcag aataaagttg gtcaagagga   2400
acatattgaa tatttagctc gtagttttca tgagagtcga ttgccaagaa aacccacgcc   2460
acctacaacg gttcctgatg aggtggttag catagttctt aatataagtt ttaatataca   2520
gcctgaaaat cttgagagaa taaaagaaga acatcgattt tccatggcag ctgagaatat   2580
tgtaggagat cttctagaaa gattaacaag acgaactcca attcactgtt ccttgcattc   2640
taaaacctta aataccagaa aacagctttt tcaaagttgt tttcaaagtt ggcgtataac   2700
atagtatcga cggagccgat tttgaaaccg cggtgatcac aggcagcaac gctctgtcat   2760
cgttacaatc aacatgctac cctccgcgag atcatccgtg tttcaaaccc ggcagcttag   2820
ttgccgttct tccgaatagc atcggtaaca tgagcaaagt ctgccgcctt acaacggctc   2880
tcccgctgac gccgtcccgg actgatgggc tgcctgtatc gagtggtgat tttgtgccga   2940
gctgccggtc ggggagctgt tggctggctg gtggcaggat atattgtggt gtaaacaaat   3000
tgacgcttag acaacttaat aacacattgc ggacgttttt aatgtactga attaacgccg   3060
```

```
aattaattcg ggggatctgg attttagtac tggattttgg ttttaggaat tagaaatttt   3120
attgatagaa gtattttaca aatacaaata catactaagg gtttcttata tgctcaacac   3180
atgagcgaaa ccctatagga accctaattc ccttatctgg gaactactca cacattatta   3240
tggagaaact cgagcttgtc gatcgacaga tccggtcggc atctactcta tttctttgcc   3300
ctcggacgag tgctggggcg tcggtttcca ctatcggcga gtacttctac acagccatcg   3360
gtccagacgg ccgcgcttct gcgggcgatt tgtgtacgcc cgacagtccc ggctccggat   3420
cggacgattg cgtcgcatcg accctgcgcc caagctgcat catcgaaatt gccgtcaacc   3480
aagctctgat agagttggtc aagaccaatg cggagcatat acgcccggag tcgtggcgat   3540
cctgcaagct ccggatgcct ccgctcgaag tagcgcgtct gctgctccat acaagccaac   3600
cacggcctcc agaagaagat gttggcgacc tcgtattggg aatccccgaa catcgcctcg   3660
ctccagtcaa tgaccgctgt tatgcggcca ttgtccgtca ggacattgtt ggagccgaaa   3720
tccgcgtgca cgaggtgccg gacttcgggg cagtcctcgg cccaaagcat cagctcatcg   3780
agagcctgcg cgacggacgc actgacggtg tcgtccatca cagtttgcca gtgatacaca   3840
tggggatcag caatcgcgca tatgaaatca cgccatgtag tgtattgacc gattccttgc   3900
ggtccgaatg ggccgaaccc gctcgtctgg ctaagatcgg ccgcagcgat cgcatccata   3960
gcctccgcga ccggttgtag aacagcgggc agttcggttt caggcaggtc ttgcaacgtg   4020
acaccctgtg cacggcggga gatgcaatag gtcaggctct cgctaaactc cccaatgtca   4080
agcacttccg gaatcgggag cgcggccgat gcaaagtgcc gataaacata acgatctttg   4140
tagaaaccat cggcgcagct atttacccgc aggacatatc cacgccctcc tacatcgaag   4200
ctgaaagcac gagattcttc gccctccgag agctgcatca ggtcggagac gctgtcgaac   4260
ttttcgatca gaaacttctc gacagacgtc gcggtgagtt caggcttttt catatctcat   4320
tgccccccgg gatctgcgaa agctcgagag agatagattt gtagagagag actggtgatt   4380
tcagcgtgtc ctctccaaat gaaatgaact tccttatata gaggaaggtc ttgcgaagga   4440
tagtgggatt gtgcgtcatc ccttacgtca gtggagatat cacatcaatc cacttgcttt   4500
gaagacgtgg ttggaacgtc ttcttttttcc acgatgctcc tcgtgggtgg gggtccatct   4560
ttgggaccac tgtcggcaga ggcatcttga acgatagcct ttcctttatc gcaatgatgg   4620
catttgtagg tgccaccttc cttttctact gtccttttga tgaagtgaca gatagctggg   4680
caatggaatc cgaggaggtt tcccgatatt accctttgtt gaaaagtctc aatagccctt   4740
tggtcttctg agactgtatc tttgatattc ttggagtaga cgagagtgtc gtgctccacc   4800
atgttatcac atcaatccac ttgctttgaa gacgtggttg gaacgtcttc tttttccacg   4860
atgctcctcg tgggtggggg tccatctttg ggaccactgt cggcagaggc atcttgaacg   4920
atagcctttc ctttatcgca atgatggcat ttgtaggtgc caccttcctt ttctactgtc   4980
cttttgatga agtgacagat agctgggcaa tggaatccga ggaggtttcc cgatattacc   5040
ctttgttgaa aagtctcaat agccctttgg tcttctgaga ctgtatcttt gatattcttg   5100
gagtagacga gagtgtcgtg ctccaccatg ttggcaagct gctctagcca atacgcaaac   5160
cgcctctccc cgcgcgttgg ccgattcatt aatgcagctg gcacgacagg tttcccgact   5220
ggaaagcggg cagtgagcgc aacgcaatta atgtgagtta gctcactcat taggcacccc   5280
aggctttaca ctttatgctt ccggctcgta tgttgtgtgg aattgtgagc ggataacaat   5340
ttcacacagg aaacagctat gaccatgatt acgaattcga gctcggtacc cggggatcct   5400
```

```
ctagagtcga cctgcaggca tgcaagcttc tagagatccg tcaacatggt ggagcacgac   5460
actctcgtct actccaagaa tatcaaagat acagtctcag aagaccaaag ggctattgag   5520
acttttcaac aaagggtaat atcgggaaac ctcctcggat tccattgccc agctatctgt   5580
cacttcatca aaaggacagt agaaaaggaa ggtggcacct acaaatgcca tcattgcgat   5640
aaaggaaagg ctatcgttca agatgcctct gccgacagtg gtcccaaaga tggaccccca   5700
cccacgagga gcatcgtgga aaaagaagac gttccaacca cgtcttcaaa gcaagtggat   5760
tgatgtgata acatggtgga gcacgacact ctcgtctact ccaagaatat caaagataca   5820
gtctcagaag accaaagggc tattgagact tttcaacaaa gggtaatatc gggaaacctc   5880
ctcggattcc attgcccagc tatctgtcac ttcatcaaaa ggacagtaga aaaggaaggt   5940
ggcacctaca aatgccatca ttgcgataaa ggaaaggcta tcgttcaaga tgcctctgcc   6000
gacagtggtc ccaaagatgg acccccaccc acgaggagca tcgtggaaaa agaagacgtt   6060
ccaaccacgt cttcaaagca agtggattga tgtgatatct ccactgacgt aagggatgac   6120
gcacaatccc actatccttc gcaagaccct tcctctatat aaggaagttc atttcatttg   6180
gagaggacga cctgcaggct gaggcttaat atggcttcct ctatgctctc ctccgccgct   6240
gtggttacat ccccggctca ggccaccatg gtcgctccat tcaccggctt gaagtcatcc   6300
gctgcattcc cggtcacccg caagaccaac aaggacatca cttccatcgc aagcaacggg   6360
ggaagatcta gctgcatgaa ggagctcggc gcgcctatgg attcttccac cgccaccgcc   6420
atgacagctc cattcattga tcctactgat catgtgaatc tcaaaactga tactgatgcc   6480
tcagagaatc gaaggatggg aaattataaa cccagcattt ggaattatga tttttacaa   6540
tcacttgcaa ctcatcacaa tattgtggaa gagaggcatc taaagcttgc tgagaagctg   6600
aagggccaag tgaagtttat gtttggggca ccaatggagc cgttagcaaa gctggagctt   6660
gtggatgtgg ttcaaaggct tgggctaaac cacctatttg agacagagat caaggaagcg   6720
ctgtttagta tttacaagga tgggagcaat ggatggtggt ttggccacct tcatgcgaca   6780
tctctccgat ttaggctgct acgacagtgt gggcttttta ttccccaaga tgtgtttaaa   6840
acgttccaaa acaaaactgg ggaatttgat atgaaactgt gggacaacgt aaaagggctg   6900
ctgagcttat atgaagcttc atacttggga tggaagggtg aaaacatcct agatgaagcc   6960
aaggccttca ccaccaagtg cttgaaaagt gcatgggaaa atatatccga aaagtggtta   7020
gccaaaagag tgaagcatgc tttggctttg cctttgcatt ggagagtccc tcgaatcgaa   7080
gctagatggt tcattgaggt atatgagcaa gaagcgaata tgaacccaac actactcaaa   7140
ctcgcaaaat tagactttaa tatggtgcaa tcaattcatc agaaagagat tggggaatta   7200
gcaaggtggt gggtgactac tggcttggat aagttagact ttgctaggaa taatttactg   7260
cagagctata tgtggagctg cgcgattgct tccgacccga agttcaaact tgctagagaa   7320
actattgtcg aaatcggaag tgtactcaca gttgttgacg atggatatga cgtctatggt   7380
tcaatggacg aacttgatct ctacacaagc tccgttgaaa ggtggagctg tgtgaaaatt   7440
gacaagttgc caaacacgtt aaaattaatt tttatgtcta tgttcaacaa gaccaatgag   7500
gttggtcttc gagtccagca tgagcgaggc tacaatagca tccctacttt tatcaaagcg   7560
tgggttgaac agtgtaaatc ataccagaaa gaagcaagat ggttccacgg gggacacacg   7620
cctccattgg aagaatatag cttgaatgga cttgtttcca taggattccc tctcttgtta   7680
atcacaggct acgtggcaat cgctgagaac gaggctgcac tggataaagt gcaccccctt   7740
cctgatcttc tgcactactc ctccctcctt agtcgcctca tcaatgatat aggaacgtct   7800
```

```
ccggatgaga tggcaagagg cgataatctg aagtcaatcc attgttacat gaacgaaact   7860

ggggcttccg aggaagttgc tcgtgagcac ataaagggag taatcgagga gaattggaaa   7920

atactgaatc agtgctgctt tgatcaatct cagtttcagg agccttttat aaccttcaat   7980

ttgaactctg ttcgagggtc tcatttcttc tatgaatttg gggatggctt tggggtgacg   8040

gatagctgga caaaggttga tatgaagtcc gttttgatcg accctattcc tctcggcgag   8100

gagtagatta aacctcagcc ccgggagctc gtcgacgcat gcccgctgaa atcaccagtc   8160

tctctctaca aatctatctc tctctataat aatgtgtgag tagttcccag ataagggaat   8220

tagggttctt atagggtttc gctcatgtgt tgagcatata agaaaccctt agtatgtatt   8280

tgtatttgta aaatacttct atcaataaaa tttctaattc ctaaaaccaa aatccagggg   8340

tacgatctct agaagcttgg cactggccgt cgttttacaa cgtcgtgact gggaaaaccc   8400

tggcgttacc caacttaatc gccttgcagc acatccccct ttcgccagct ggcgtaatag   8460

cgaagaggcc cgcaccgatc gcccttccca acagttgcgc agcctgaatg gcgaatgcta   8520

gagcagcttg agcttggatc agattgtcgt ttcccgcctt cagtttatct tgctgaaaaa   8580

ctcgagccat ccggaagatc tggcggccgc tctccctata gtgagtcgta ttacgccgga   8640

tggatatggt gttcaggcac aagtgttaaa gcagttgatt ttattcacta tgatgaaaaa   8700

aacaatgaat ggaacctgct ccaagttaaa aatagagata ataccgaaaa ctcatcgagt   8760

agtaagatta gagataatac aacaataaaa aaatggttta gaacttactc acagcgtgat   8820

gctactaatt gggacaattt tccagatgaa gtatcatcta agaatttaaa tgaagaagac   8880

ttcagagctt ttgttaaaaa ttatttggca aaaataatat aattcggctg caggggc      8937
```

<210> SEQ ID NO 17
<211> LENGTH: 552
<212> TYPE: PRT
<213> ORGANISM: Pogostemon cablin

<400> SEQUENCE: 17

```
Met Glu Leu Tyr Ala Gln Ser Val Gly Val Gly Ala Ala Ser Arg Pro
1               5                   10                  15

Leu Ala Asn Phe His Pro Cys Val Trp Gly Asp Lys Phe Ile Val Tyr
            20                  25                  30

Asn Pro Gln Ser Cys Gln Ala Gly Glu Arg Glu Glu Ala Glu Glu Leu
        35                  40                  45

Lys Val Glu Leu Lys Arg Glu Leu Lys Glu Ala Ser Asp Asn Tyr Met
    50                  55                  60

Arg Gln Leu Lys Met Val Asp Ala Ile Gln Arg Leu Gly Ile Asp Tyr
65                  70                  75                  80

Leu Phe Val Glu Asp Val Asp Glu Ala Leu Lys Asn Leu Phe Glu Met
                85                  90                  95

Phe Asp Ala Phe Cys Lys Asn Asn His Asp Met His Ala Thr Ala Leu
            100                 105                 110

Ser Phe Arg Leu Leu Arg Gln His Gly Tyr Arg Val Ser Cys Glu Val
        115                 120                 125

Phe Glu Lys Phe Lys Asp Gly Lys Asp Gly Phe Lys Val Pro Asn Glu
    130                 135                 140

Asp Gly Ala Val Ala Val Leu Glu Phe Phe Glu Ala Thr His Leu Arg
145                 150                 155                 160

Val His Gly Glu Asp Val Leu Asp Asn Ala Phe Asp Phe Thr Arg Asn
                165                 170                 175
```

-continued

```
Tyr Leu Glu Ser Val Tyr Ala Thr Leu Asn Asp Pro Thr Ala Lys Gln
            180                 185                 190

Val His Asn Ala Leu Asn Glu Phe Ser Phe Arg Arg Gly Leu Pro Arg
        195                 200                 205

Val Glu Ala Arg Lys Tyr Ile Ser Ile Tyr Glu Gln Tyr Ala Ser His
    210                 215                 220

His Lys Gly Leu Leu Lys Leu Ala Lys Leu Asp Phe Asn Leu Val Gln
225                 230                 235                 240

Ala Leu His Arg Arg Glu Leu Ser Glu Asp Ser Arg Trp Trp Lys Thr
                245                 250                 255

Leu Gln Val Pro Thr Lys Leu Ser Phe Val Arg Asp Arg Leu Val Glu
            260                 265                 270

Ser Tyr Phe Trp Ala Ser Gly Ser Tyr Phe Glu Pro Asn Tyr Ser Val
        275                 280                 285

Ala Arg Met Ile Leu Ala Lys Gly Leu Ala Val Leu Ser Leu Met Asp
    290                 295                 300

Asp Val Tyr Asp Ala Tyr Gly Thr Phe Glu Glu Leu Gln Met Phe Thr
305                 310                 315                 320

Asp Ala Ile Glu Arg Trp Asp Ala Ser Cys Leu Asp Lys Leu Pro Asp
                325                 330                 335

Tyr Met Lys Ile Val Tyr Lys Ala Leu Leu Asp Val Phe Glu Glu Val
            340                 345                 350

Asp Glu Glu Leu Ile Lys Leu Gly Ala Pro Tyr Arg Ala Tyr Tyr Gly
        355                 360                 365

Lys Glu Ala Met Lys Tyr Ala Ala Arg Ala Tyr Met Glu Glu Ala Gln
    370                 375                 380

Trp Arg Glu Gln Lys His Lys Pro Thr Thr Lys Glu Tyr Met Lys Leu
385                 390                 395                 400

Ala Thr Lys Thr Cys Gly Tyr Ile Thr Leu Ile Ile Leu Ser Cys Leu
                405                 410                 415

Gly Val Glu Glu Gly Ile Val Thr Lys Glu Ala Phe Asp Trp Val Phe
            420                 425                 430

Ser Arg Pro Pro Phe Ile Glu Ala Thr Leu Ile Ile Ala Arg Leu Val
        435                 440                 445

Asn Asp Ile Thr Gly His Glu Phe Glu Lys Lys Arg Glu His Val Arg
    450                 455                 460

Thr Ala Val Glu Cys Tyr Met Glu Glu His Lys Val Gly Lys Gln Glu
465                 470                 475                 480

Val Val Ser Glu Phe Tyr Asn Gln Met Glu Ser Ala Trp Lys Asp Ile
                485                 490                 495

Asn Glu Gly Phe Leu Arg Pro Val Glu Phe Pro Ile Pro Leu Leu Tyr
            500                 505                 510

Leu Ile Leu Asn Ser Val Arg Thr Leu Glu Val Ile Tyr Lys Glu Gly
        515                 520                 525

Asp Ser Tyr Thr His Val Gly Pro Ala Met Gln Asn Ile Ile Lys Gln
    530                 535                 540

Leu Tyr Leu His Pro Val Pro Tyr
545                 550
```